US009353371B2

(12) United States Patent
Hastings et al.

(10) Patent No.: US 9,353,371 B2
(45) Date of Patent: May 31, 2016

(54) ANTISENSE COMPOUNDS TARGETING GENES ASSOCIATED WITH USHER SYNDROME

(75) Inventors: Michelle L. Hastings, North Chicago, IL (US); Frank Rigo, Carlsbad, CA (US); C. Frank Bennett, Carlsbad, CA (US)

(73) Assignees: Ionis Pharmaceuticals, Inc., Carlsbad, CA (US); Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 14/009,782

(22) PCT Filed: May 2, 2012

(86) PCT No.: PCT/US2012/036189
§ 371 (c)(1), (2), (4) Date: Dec. 16, 2013

(87) PCT Pub. No.: WO2012/151324
PCT Pub. Date: Nov. 8, 2012

(65) Prior Publication Data

US 2014/0114057 A1 Apr. 24, 2014

Related U.S. Application Data

(60) Provisional application No. 61/587,074, filed on Jan. 16, 2012, provisional application No. 61/481,654, filed on May 2, 2011.

(51) Int. Cl.
*C12N 15/113* (2010.01)

(52) U.S. Cl.
CPC .......... *C12N 15/113* (2013.01); *C12N 2310/11* (2013.01); *C12N 2310/315* (2013.01);

(Continued)

(58) Field of Classification Search
USPC .......................................................... 536/24.5
See application file for complete search history.

(56) References Cited

U.S. PATENT DOCUMENTS 3,687,808 A 8/1972 Merigan et al.
4,845,205 A 7/1989 Huynh Dinh et al.

(Continued)

FOREIGN PATENT DOCUMENTS

WO WO 99/14226 3/1999
WO WO03000707 A2 * 1/2003

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Terra C Gibbs
(74) *Attorney, Agent, or Firm* — Knobbe Martens Olson & Bear LLP

(57) ABSTRACT

The present invention provides compounds comprising oligonucleotides complementary to an Usher transcript. Certain such compounds are useful for hybridizing to an Usher transcript, including but not limited, to an Usher transcript in a cell. In certain embodiments, such hybridization results in modulation of splicing of the Usher transcript. In certain such embodiments, the Usher transcript includes a mutation that results in cryptic splicing and hybridization of the oligonucleotide results in a decrease in the amount of cryptic splicing. In certain embodiments, such compounds are used to treat Usher Syndrome.

15 Claims, 29 Drawing Sheets

(52) U.S. Cl.
CPC ... *C12N2310/321* (2013.01); *C12N 2310/3341* (2013.01); *C12N 2310/346* (2013.01); *C12N 2320/33* (2013.01)

(56) References Cited

U.S. PATENT DOCUMENTS

| | | | | |
|---|---|---|---|---|
| 5,034,506 | A | 7/1991 | Summerton et al. | |
| 5,130,302 | A | 7/1992 | Spielvogel et al. | |
| 5,134,066 | A | 7/1992 | Rogers et al. | |
| 5,166,315 | A | 11/1992 | Summerton et al. | |
| 5,175,273 | A | 12/1992 | Bischofberger et al. | |
| 5,185,444 | A | 2/1993 | Summerton et al. | |
| 5,367,066 | A | 11/1994 | Urdea et al. | |
| 5,432,272 | A | 7/1995 | Benner | |
| 5,457,187 | A | 10/1995 | Gmelner et al. | |
| 5,459,255 | A | 10/1995 | Cook et al. | |
| 5,484,908 | A | 1/1996 | Froehler et al. | |
| 5,502,177 | A | 3/1996 | Matteucci et al. | |
| 5,525,711 | A | 6/1996 | Hawkins et al. | |
| 5,552,540 | A | 9/1996 | Haralambidis | |
| 5,587,469 | A | 12/1996 | Cook et al. | |
| 5,594,121 | A | 1/1997 | Froehler et al. | |
| 5,596,091 | A | 1/1997 | Switzer | |
| 5,614,617 | A | 3/1997 | Cook et al. | |
| 5,645,985 | A | 7/1997 | Froehler et al. | |
| 5,681,941 | A | 10/1997 | Cook et al. | |
| 5,698,685 | A | 12/1997 | Summerton et al. | |
| 5,750,692 | A | 5/1998 | Cook et al. | |
| 5,763,588 | A | 6/1998 | Matteucci et al. | |
| 5,830,653 | A | 11/1998 | Froehler et al. | |
| 6,005,096 | A | 12/1999 | Matteucci et al. | |
| 6,268,490 | B1 | 7/2001 | Imanishi et al. | |
| 6,444,465 | B1 * | 9/2002 | Wyatt et al. | 435/375 |
| 6,525,191 | B1 | 2/2003 | Ramasamy | |
| 6,670,461 | B1 | 12/2003 | Wengel et al. | |
| 6,770,748 | B2 | 8/2004 | Imanishi et al. | |
| 6,794,499 | B2 | 9/2004 | Wengel et al. | |
| 7,034,133 | B2 | 4/2006 | Wengel et al. | |
| 7,053,207 | B2 | 5/2006 | Wengel | |
| 7,176,304 | B2 * | 2/2007 | McSwiggen | C12N 15/111 435/325 |
| 7,399,845 | B2 | 7/2008 | Seth et al. | |
| 7,427,672 | B2 | 9/2008 | Imanishi et al. | |
| 7,741,457 | B2 | 6/2010 | Swayze et al. | |
| 8,501,805 | B2 | 8/2013 | Seth et al. | |
| 8,530,640 | B2 | 9/2013 | Seth et al. | |
| 8,546,556 | B2 | 10/2013 | Seth et al. | |
| 8,648,053 | B2 | 2/2014 | Hastings et al. | |
| 2004/0171570 | A1 | 9/2004 | Allerson et al. | |
| 2005/0009771 | A1 | 1/2005 | Levanon et al. | |
| 2005/0130923 | A1 | 6/2005 | Bhat et al. | |
| 2007/0287831 | A1 | 12/2007 | Seth et al. | |
| 2008/0039618 | A1 | 2/2008 | Allerson et al. | |
| 2008/0194503 | A1 * | 8/2008 | Monia et al. | 514/44 |
| 2009/0088721 | A1 | 4/2009 | de Bizemont et al. | |
| 2009/0163435 | A1 | 6/2009 | Bader et al. | |
| 2010/0190841 | A1 | 7/2010 | Farrar et al. | |
| 2010/0203076 | A1 | 8/2010 | Fotin-Mleczek et al. | |
| 2011/0021605 | A1 | 1/2011 | Schulte et al. | |
| 2012/0149757 | A1 | 6/2012 | Krainer et al. | |
| 2013/0035367 | A1 * | 2/2013 | Hastings | 514/44 A |
| 2014/0243388 | A1 | 8/2014 | Hastings et al. | |

FOREIGN PATENT DOCUMENTS

| | | |
|---|---|---|
| WO | WO 2004/106356 | 12/2004 |
| WO | WO 2005/021570 | 3/2005 |
| WO | WO 2007/134181 | 11/2007 |
| WO | WO 2008/049085 | 4/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2012/151324 | 11/2012 |

OTHER PUBLICATIONS

Ayuso et al., "Retinitis pigmentosa and allied conditions today: a paradigm of translational research" Genome Med. (2010) 2(5):34.
Braasch et al., "Novel Antisense and Peptide Nucleic Acid Strategies for Controlling Gene Expression" Biochemistry (2002) 41(14): 4503-4510.
Braasch et al., "Locked nucleic acid (LNA): fine-tuning the recognition of DNA and RNA" Chem. Biol. (2001) 8:1-7.
Crooke et al., "Pharmacokinetic Properties of Several Novel Oligonucleotide Analogs in mice" J. Pharmacol. Exp. Ther. (1996) 277(2):923-937.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gibbs et al., "Function of MYO7A in the Human RPE and the Validity of Shaker1 Mice as a Model for Usher Syndrome 1B" Investigative Ophthalmology & Visual Science (2010) 51(2):1130-1135.
Goldmann et al. "Beneficial read-through of a USH1C nonsense mutation by designed aminoglycoside NB30 in the retina." Invest Ophthalmol Vis Sci. (2010) 51(12):6671-6680.
Jodelka et al., "Antisense oligonucleotide correction of splicing in a mouse model of Usher 1-5 syndrome." 2010 Rustbelt RNA Meeting. RRM, retrieved from the Internet Jan. 29, 2014: <http://www.rustbeltrna.org/2010/talks.php?all>]; Abstract.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Lentz et al., "Ush1c216A knock-in mouse survives Katrina." Mutat Res. (2007) 616(1-2):139-144.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Lopez et al., "Mutational frequencies in usherin(USH2A gene) in 26 Colombian individuals with Usher syndrome type II" Biomedica. (2011) 31(1 ):82-90. [Article in Spanish].
Manoharan et al., "Chemical Modifications to Improve Uptake and Bioavailability of Antisense Oligonucleotides" Ann. N.Y. Acad. Sci. (1992) 660:306.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
McCaffrey et al., "Blocking Cryptic Splicing in Usher syndrome using antisense oligonucleotides." The Association for Research in

(56) References Cited

OTHER PUBLICATIONS

Vision and Opthalmology, Abstract, May 3, 2011, Ft. Lauderdale, FL.
Millan et al., "An Update on the Genetics of Usher Syndrome" Journal of Ophthalmology (2011) , Article ID 417217, 1-8.
Mishra et al., "Improved leishmanicidal effect of phosphorotioate antisense oligonucleotides by LDL-mediated delivery" Biochim. Biophys. Acta (1995) 1264:229-237.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3(3):239-243.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Vache et al., "Usher syndrome type 2 caused by activation of an USH2A pseudoexon: implications for diagnosis and therapy." Hum Mutat. (2012) 33(1):104-108.
Verpy et al., "A defect in harmonin, a PDZ domain-containing protein expressed in the inner ear sensory hair cells, underlies Usher syndrome type 1C" Nat. enet. (2000) 26(1):51-55.
Wahlestedt et al., "Potent and nontoxic antisense oligonucleotide containing locked nucleic acids" Proc. Natl. Acad. Sci. USA (2000) 97: 5633-5638.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US12/36189 daed Oct. 5, 2012.
El-Amraoui et al., "Usher I Syndrome: Unraveling the Mechanisms that Underlie the Cohesion of the Growing Hair Bundle in Inner Ear Sensory Cells" Journal of Cell Science, (2005) 118: 4593-4603.
Goemans et al., "Systemic Administration of PRO051 in Duchenne's Muscular Dystrophy" New Engl J. of Med. (2011) 364: 1513-1522.
Hastings et al., "Control of Pre-mRNA Splicing by the General Splicing Factors PUF60 and U2AF65" PloS ONE (2007) 6: e538.
Hastings et al., "Tetracyclines That Promote SMN2 Exon 7 Splicing as Therapeutics for Spinal Muscular Atrophy", Sci. Transl Med. (2009) 1(5): 5ra12, 1-10.
Hua et al., "Antisense Correction of SMN2 splicing in the CNS Rescues Necrosis in a Type III SMA Mouse Model" Genes Dev. (2010) 24: 1634-1644.
Kral et al., "Profound Deafness in Childhood" The New England Journal of Medicine (2010) 365(15): 1438-1450.
Morton et al., "New Hearing Screening—A Silent Revolution" Massachusetts Medical Society (2006) 354: 2151-2164.
U.S. Appl. No. 61/694,973, filed Oct. 20, 2010, Hastings et al.
U.S. Appl. No. 61/481,613, filed May 2, 2011, Hastings et al.

* cited by examiner

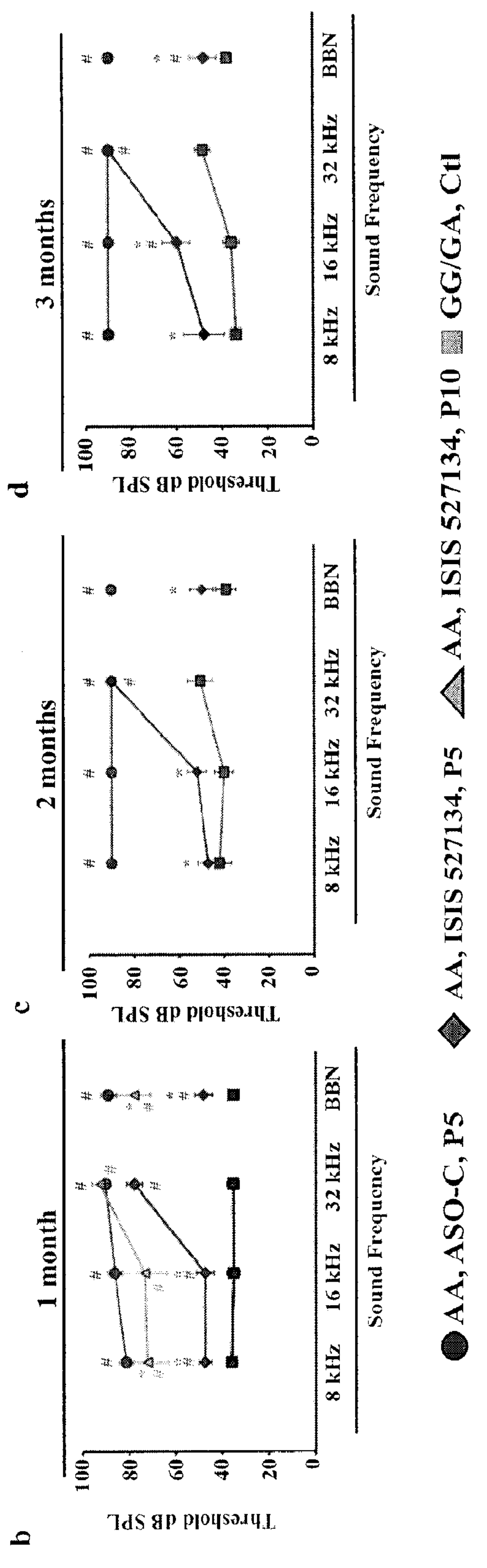
Figure 3 b-d

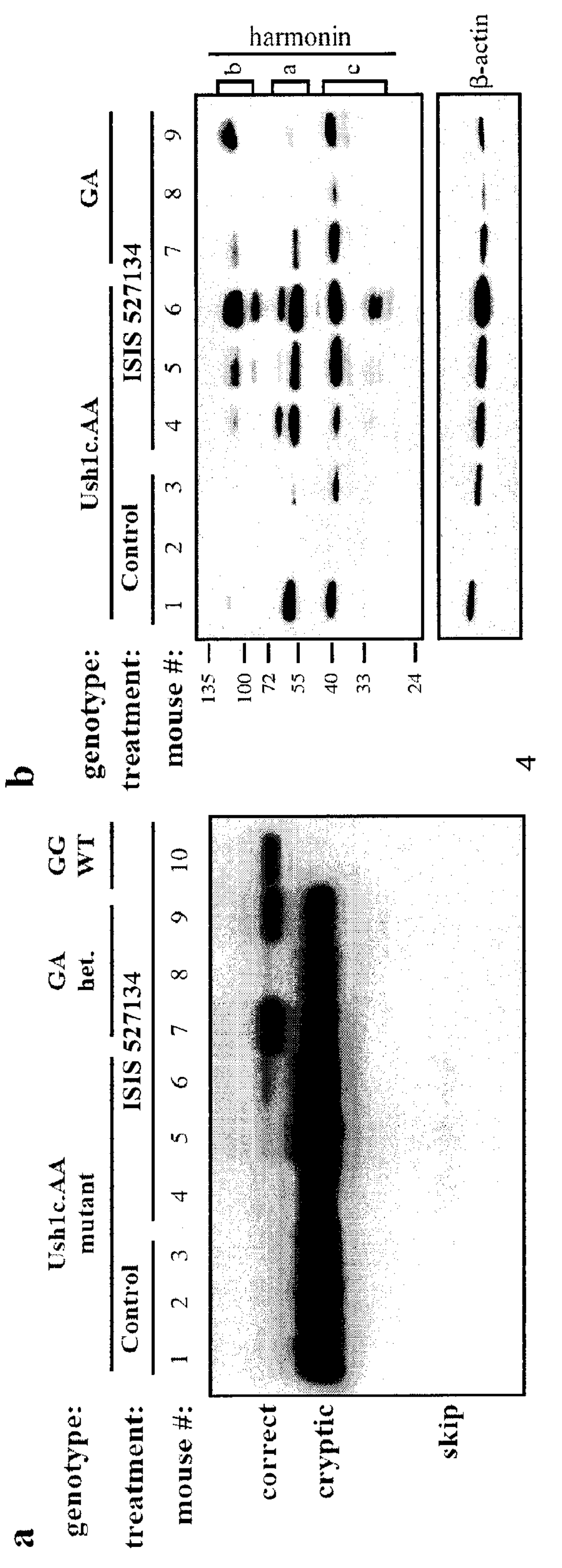
Figure 12 a-b

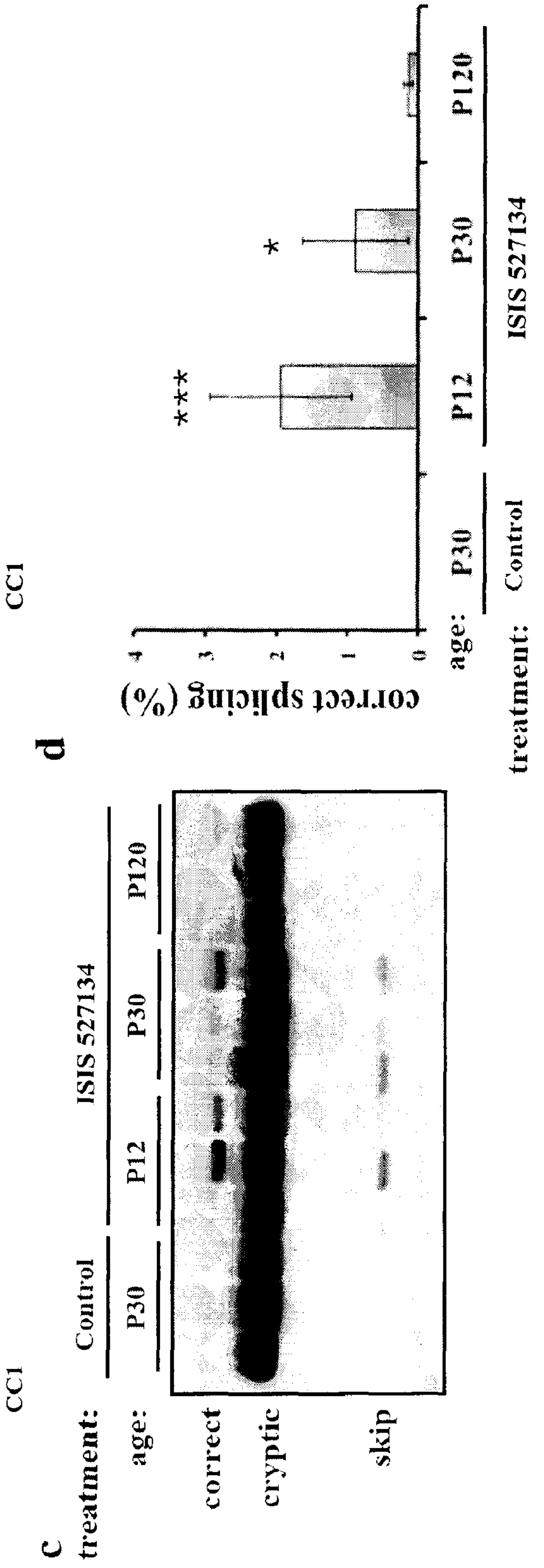
Figure 12 c-d

SEQUENCE LISTING

```
<160> NUMBER OF SEQ ID NOS: 59

<210> SEQ ID NO 1
<211> LENGTH: 51722
<212> TYPE: DNA
<213> ORGANISM: Homo sapiens

<400> SEQUENCE: 1

ctttgggagg ccgaggtggg cagatcacga ggtcaggaga tcgagacctt cctggcgaac     60

acggtgaaac cccgtctcta ctaaaaatac aaaaaaaaaa aattagccgg gcgtggtggc    120

gggcgcctgt agtcccagct actcgggagg ctgaggcagg agaatggcgt gaacccggga    180

ggcggagctt gcagtgagcc aagatcatgc cactgcactg tagcctgggc gacagagcga    240

gactccgtct cggggggggaa aaaaaaagaa tatccagaga aaacggacta gattgccccg    300

ccccccgccc gtgtaaatag tttccgtatc tctctattcc ggtccccaca aaaaagtccc    360

aaacctcctc cctacgtctc cacgatcttc ttcctcaaac gcatgtgttc aggtaccact    420

tccagagaaa taccagcttg aagcccagct actgccacct caggcccata ggcacactgg    480

ggcccatttg ctcccaggct tcagtgggag gcgacgactc agcaccttcg actccagcct    540

cgcagcggcc ccgccccaca gaggcctggc cccgccccctc cgcgctcagg ccccgccccc    600

agctccgagg gcggctggcc cggtcgcggt cgcggctctt tccagctcct ggcagccggg    660

cacccgaagg aacgggtcgt gcaacgacgc agctggacct ggcccagcca tggaccgaaa    720

agtggcccga gaattccggc ataaggtcag agctgcaggg cgccccaggc ttctgggact    780

ccggagtcct gggcgcggtg ggtagggggt ggacaccccg gcactgcccc tccctttttcc    840

ggccccacct gatggctctg gttgggctgg gacacccgag ggtcgtctgg ctggcagcag    900

ggatccccag taaagtgagg gagggaatgc ggggactccc ggctcaagga ctgctaaacg    960

agtcgatctt ctgccagcct ttctccctct gccttccagg ggcagggacg tctctggggt   1020

ttgaattcct tccagtcttg gccgcttttc tgaggtgccc cctttgtggg caagcccctc   1080

tccttcctag tgcccccagc tcagggctgt tgaggcatgt ggagacagtc tggggcagta   1140

tctgagaggt gagggttggg agaagggaaa ctagacgtct ctctctctgc cttttgacct   1200

cagaacatga gttagaagca tttcagccct gcctgcctaa gggcgtttct tagggtctga   1260

gaagtagctg aggagctggt gctgacccgg gtgcggtggg gaggaaggga ggaggtactg   1320

agggcgtcgg agctgggctc tggccggcca gatccttcag gcagagccgg gtccaccctg   1380

gtgtgtccca gtgaggggcc tcactggtgg tctgggattc tcaaggacca tctctggaag   1440

tggccaggtt tcacacaggg catttcgaga atgattcaca aagctgtgca gaatctgctg   1500

aggccctgag accagagagg gccatcaaag agatccagcc tacttcccca ccaagtctta   1560
```

```
ggatgcctct gagtctgggg atgaagccgc ttgggggggg tgggtggtat ctggagctcc   1620
ccacaggccc tgcctgaggg gcaggtaact attgataact taactattga taactgtgtg   1680
acccaaggct ctcccaaaga ccccaggggc agtgtcttta gaccaagcca aacctcttcc   1740
tggtttgaga gctgagctca ggtagggcag gtcagggtgc ttaactcctt ccttcccata   1800
aagaggccca taggagccca aggagctagc cagtgtaggg gccacagggg cttggggcca   1860
agggcccggg gtcagttatt catttaataa gcatgttttg agcatcctct cagccatacc   1920
cagtctgtgc cctttgctgg tggtgtaggt gggaggcaga ccctaccctg gtaattaccc   1980
atgtctgagt gctgcgtgtt gaggccaagc ttttgtaggg gcacaaaggg acagctcaaa   2040
ctggcagaag gctcctgaaa acaaggtctt gggcatttct ggtcctgctc ccaggggtgg   2100
gtgatagctg gaagttcagc aggaatttag gggctggcga ataccaaggg gagcttgaga   2160
gagcattcac tgttacatcc tgttgcaaag agacatgtcg gaagaaattt cagccactaa   2220
ggacattttg tgagtgtaga tttcaggcaa cccagtttga aggagctcag ccttccatcc   2280
cccaacccaa gactcagggt tgaatttcag tttcctgccc ctggcctgaa ataacatcag   2340
gtcttctgcc ttcactctgt ggggtacctg ctctctcttt tttgtgagaa tcatctccag   2400
ggtccctggt gtctgatgca gatcctgggt ttgccctgtt cctcttcccc aggtcccaca   2460
ggctccaaag ggcctcagac ctccacgttt cctctgccct actcttcctc atcgcaacag   2520
tcattactta ttaatatccc tgtgtgcagg cagggcaggc gccatgcgct aggcaaggcc   2580
caggctggac tttgtgccct gctgccttgg agacagccac agccttcccc tcccaggttg   2640
gggatcatcc aggaactggg gagagaggat gaagcacaga ggatagaaag gaggcacaca   2700
gacatgctgg gagaaattta cagcttgctg ttgtttgctt tgtaggggtc ccttccttag   2760
tgttttggaa gaaatggttt gtgatctaaa tccttagttg ttggaagtaa tatttaaggt   2820
agtgtgttat aatggaaagt gctctgtgac cttgagcaag ttacttaatc tctctgtgcc   2880
tcagtgctct tacttgtgaa aagagataac aatatttaac gaataaggtt accatgaatg   2940
ctgaatgaga cctacatgtg tgtggggagc ttaaatagac cctggcactt agggagctct   3000
caagaaatgt ccatgttgat tattatctgg agttagcaga actgggacca aatcttagcc   3060
ctgtcactgt caggaagacc ttgaccaagc cacccactct ccctgagttt tagtttcttc   3120
agctatgaga tggagtttgt agaacttacc tcacaagaca gtcaaaacta actagcaatt   3180
aaagtactgg ctgctctggg cccacagtaa ccacactgtt tccagctgat acctgcagag   3240
tgtccagtgg gagccaacag gctccaggca tcgactccct ttgatttgtg aagttacccc   3300
aaggccgcca ggagcacttg catacccttc cagtaactag tagcaacctt gggccaggat   3360
gtgggggagc agggcttggt cagagactgt tttctccctc agagaaccag ctttcaaagg   3420
gagactgctc ttctgttcgc agcaccagca cagggtagga acttggttac tcattggctt   3480
aaaagtattt attgcctctt cagcaatcat gcatttatga gcatagctgt gtattctgcc   3540
tgaggccagg catctgacaa ccggttggga tgaataagat cagaaagagc caccactctc   3600
taggaatttg ttaatcattc atttattcac ataggcaata aatattgact gagcccttaa   3660
tatatgccag gcagtactct aagcatcaaa aaacaaaata aagcccttgc tgtcttagac   3720
agtacattcc agtagggaag acaggtagtt aaaaggaaat caacaaaagt atcatacaat   3780
gccagatagt gataaattct atgaaaaaat aaactaagat ggggagagag agatagtaag   3840
tgacaaggta ggcagtcacg aaggcctctc tgaagaggtg acatctgagc agagacctag   3900
```

-continued

```
aagaagtgag gagaaggagc cacagagata catgtagaag agcattccct aaagtggaag   3960
caacaagtgt gaaggccctg aggcaagcag atgcccgcct gtatggaaca gcaagtagga   4020
cagtgtgtcc cagaggaatc gtgagtggag aatggtgaga aatgggtcgg aggggtggta   4080
ggggcctggt aggccatggt caggtcagga ttttcttgta agtgtgaatg atttacattt   4140
aaaaggaatt gttctggctg ctctgtagag aatccactga ggggcccaag agtagaaggg   4200
gacctcagtc aggaggctcc tgcaggagcc caggccagag gcaggggctc ggactcgggt   4260
gagaatgggt cggattcagg atacatgtta aaggaaaaac tgacaggctt tgctgatgga   4320
ttggctgcga gcgtagaaag agaggcatca agggtgaatc cacatttggt ggagacggag   4380
caggttggtg gagacggagc aggaggtggt ggaaacctag cgttccactt cgaatgctgt   4440
aagtttgaga cgcctgctag aggtgactga gaaggctgta ggtctggcct ggagataagc   4500
atcggtaggt ccttgggggt gtgagtggta tttaaacccc tgagatgaat gaggtcactt   4560
agagagacag tgcagatgga gaggagacct aggacagagc ccggggtacc tcaacttttg   4620
gaggagaagg agcagcaagc gaggaaggaa agcaaggaga agcagggcgt gattgctgtg   4680
ccaggcacag ggtgaaatac tacaaactag ctgacatgtc aagagcctct gaaaagatga   4740
agggcactgt ctatgtcctt gatggtggtg atgctttcac acgtgcacat ttatccccaa   4800
actcatcagg ttgtatacac taaatatata cagcgcttta catgtcaggc atacctcaat   4860
aaagtggttc cagaaaaaga aaagaagtca ggtgtggcgg ctcacgcctg aaatcccagc   4920
attttgggag gctgaggtgg gagaatcact tgagtccatg agtttgagac cagcctgggc   4980
aacatagcga gaccccatct ctacaaaaaa tacaaaaatt agccaggtgt ggtgttgtgc   5040
acctgtagtc ccagctactt gagaggttga ggcaggagaa tcaattgagc ctggaggttg   5100
aggctgcagt gagctgtggt cacaccactg cactccagct tgggtgacag agtaagacct   5160
ggtctcaaaa aaaaaaaaaa aaagaaaaag aaagaaacag aaacagaaag aaaagaaaga   5220
gagagagaca gagacagaga cagagagaac cctagacaag aaagaaagaa agcaaaagaa   5280
aaagaaaaga tggatgataa gaaaatgaga gtcaaataaa gcctggtacc actgggatgc   5340
acactctaaa ggcctgggaa gaagtgtggc tggatctatt catcccacta acatctacag   5400
agggccactc gctgcccact gctgtggata tagaatttat gtccacttat tgtcacttag   5460
ttttatgtaa caaacacagg acttactacc tgccaggcac tgttctgaac tcttcataat   5520
tattaactca ttaaattaat actaaaaaac aatgattaat ctctcatagt gattaaatcc   5580
cattttaaaa agagatgtta gtcctcattt tacagataag gaaactgagg cacagagagg   5640
agcagaccca gttggggaag gggttctttg gctctaccac cacactcaca agccaggcct   5700
gtgtctgggc cacacacagg cttgtgggga gacaggaggg taaagggaga aagttcagca   5760
cagcttggtg agtcccatgg cagagttggg gacaaagtgc tgttgtgtgc acagagaaag   5820
atgtggccag ctttgtgtgg gagcctaagg aaagacttgg ccaagaagag gcgacatttg   5880
aagtgagtct taaagataga ggaggagtcc acagagagga aatactgctg gtaccaccat   5940
tgctaatggc taaccagggt ggcagcaggg agcaggtggc tcgtccaagg gggaagccaa   6000
gaaagcttta tgaacaggtt ctacagaaaa gggcaggatt aaatgaccca acaagctgca   6060
ccctggggcc agatgcagga ggccagcatc cctgaagggg ccagtagagg gaaggttacc   6120
agaacaggtg agaaccaggg ctgccaaaga ggcccagaca gcagctgcag ccttgggtgg   6180
aggaacctgc ctaactgtgg cccagcagcc agcccccagg gactaggagc ctcagttcct   6240
gtctccccac gcctctcatc tcctgcttgt gcctcccgat ggctgaacac agcagaaagc   6300
```

-continued

```
cagaggggag aggagcccag gcagagccct ctggacaaag ggcagggtgg agaaggctgg   6360
aggcatgaaa ggaaaagatc tagcacacat tttggagacc ttgaaatgtc ccaggcattg   6420
tcatacgtgc tttacacata ctcactcatt taatccccgc aacagcccaa agagacttca   6480
tcaagcagaa caacatgcat tatttaattt gttctggctc tctttctccc tgtttggctg   6540
ggtgcacacc taaagttgaa tcttcctgag ttgactgtcc catggttccc ctgtgtagct   6600
atcctgaagg gccagtccat atgggggaat acagagggat gagactggag ggtaccacat   6660
ggccaaaccc agcttttgcc tccaataccc tagacaaggg gcctgaagat tgtgagggtg   6720
gagatgctcc ctgtcccctc ctccctccca cacagaccaa tagcacagtg ccagagaaac   6780
atcagtcagc aaatgctaat ctaggcaggg ctggcagcag gggcaggggg tagcagggat   6840
gataatagag atccccaaca gctatttgta gatggtgggc tcctttaggg cttctgtgct   6900
taatatcaag agggatccaa gaaaaggaaa ggctttctaa atctagtcgg agaaagaaga   6960
ctggtgtctt tcccacagta ggtgttcaat agatgtgtaa tggacaagtg gacaacaaag   7020
gagttatatt tcataagtgg ataccatgtg gtagattgaa aaaaagcaga ggttttggag   7080
ccagtaggca taggttgggg tctcaattct gtcacttctc tgagcctctg tttcctcatc   7140
tgtaaagtgg ggatgataac gttcacctca gagggttgtt aggatattaa agataataca   7200
cgtaaagttc ctcaggcagt ggacagtcag tagggagagg ctggctggga taagtgagcc   7260
agacagaaag agactcaggc tgggaggcag gtgaggaggc tccagactct agaagagggg   7320
acttgggcct catctgaaat gaaggcagga ttcagatgag aggaggaaag ctgtccattg   7380
tggatagatg gagtcgctgg gacctacttt tttgtgatga attggaagtg aactaagggg   7440
aggcagaccc agaatatatg tgctgaggac cagtggaaag gtggtgaccc aggcctgggc   7500
caacaggtca gaaagaaggc tctagactag agcaaataga gttcacgttt catcaacgga   7560
cgccactggg caccgtgcgc ttgtgtgcat gacatggttc tgggttccac agggaaatga   7620
agaacatgtt tggaaggaag ggaagaaagg agtgtgggag atttactgcg tgcctagtgc   7680
ttcgtatgta cctgagtaca gggtactggg acaatggtac aaagcaccct agagcagggg   7740
ctccccaaaa ctgatcctcg ggctagtgct aggcagaatt ccagaagaga ggaaactata   7800
taattttta atattggaaa agtaatttga tttggaccac agggaagact acaaagaaaa   7860
agtaatttaa gtgatggtgg tattgttact gcacgttcag gctttagaga aacttccatc   7920
tttctcagct ttctttcctg gtgcctttta atgcctgaag agtgaggtgt gagtgtgtgt   7980
tttcactcag gtgtggtcag agaacaaagc agtgctgttc tttctgagtc tttctgagat   8040
atttctgggt gagaatgatc cctccctttg caggatctcc tgtgtaacca gttttcaagt   8100
ttttgatgat ctatcactta gattcatatt taaagagcat tctacacaaa ccagatctat   8160
tttccctgtt agctggtatg gtctatagag aattgtttaa atagacaagt cagacatggc   8220
ggtagatgga atgttctgag tgaggacaag gagattccag tgtgtcaggg gaaggatctg   8280
ttccactgca gctgagtccc acttgggatg tggtgaagcg agcaatggca gaactgagga   8340
cagggtttga gtgacctaac cggtgacagt gggtggacat gaggccgaag agctgagctc   8400
tgcagctgtc tcaggagaca ggtaggatga gacctctggg agcagtggtc agtgctggag   8460
ggctgctgac aagggccagg agcccgggac cttcagggac aggctccttt ccaccaagac   8520
catctccaag tgatctgtgc ttggcccagg gaagggagaa aaacagaacc ctagacccta   8580
acattgcaag ttaccttact cttctacctc agttttccac ctaatgcaca ataaacatgg   8640
```

-continued

```
tctaaggagg acagttcctc actactgaaa tctaatgcta cagcaagata catttctgca   8700
aagagggata agagggaact tcagtcctaa ggcctcagtc aataagagat tctctgtccc   8760
atcttctttc ttgtgtcacc acccagggtt ataactaggc tagaagtctt tagtcagggt   8820
gtcctctctt cagccaaagc agacgtgatt tttatgctcc ccttagaaag tacaacactt   8880
gggttcaaag agtcattcaa aagatgtccc attttctcac tcattataga ccaagccaaa   8940
agtgttttct taacagtgca gaggagagag atggggctta gagataagaa aggagttctt   9000
gaaagcaaag ggttggaaat tttggcctaa agggacattg ggagttattt tcccctgcca   9060
ggcctgagtc acaatcaatg gtcatcgtgg cgtagcagaa agaacatggg ctttggagtc   9120
agacttaggt tcatatccta gctctgctta ttagctgtgg gacactgggt gagttgactt   9180
aacctctctg atcctcagtt tcctcagctg cagcattatg tgagaatatt gccccaatgt   9240
gataaacaaa tggaataaag cccatgaaaa gctcctggtg ccaccgcatg gggcattatg   9300
gggacaacat catttccctt ccccttctgt tcccatggtt acctccctcc cacctgaacc   9360
atgtgggcat accaggaggc aggcagataa attcattcaa tacttcttta ttgagagctt   9420
attatgtgtt gggcacgaga aatttagaac aaaatagatc tcatctttcc cctcatggga   9480
tttttctgtc cagcgaaggt gacagagaaa acaattcaca gagaaaacaa accttaaatt   9540
acaaattgta gtcgatctgt gaaggaattg aaacatctcc ggggtgcagg agtcggttct   9600
gtctgggtag gtgagcaggg aagacctctc tggaaaggag gtggccaggc agggaagtgg   9660
gggaagcagt ccaagcagag ggaacaagca tacgccaagg ccctgaggct ggagagcgtt   9720
cggcctgtgg gaagaactga aaggaggact ttgtagccag gaagactggt aggagaggag   9780
attgggcttt gataagtcaa agtaaggagt ttggatttag gtttggtttg gggtacaaga   9840
aactactgag caagcaagca acatatctaa tttataaaga tatttctcgc ccctgctgct   9900
aggagagttc atactcctcc atcacagccc agtgtgggca gcccaggcct gtctcaggga   9960
ggcacccctg ccccacaggc ctgagcagag ggggtgagag aatccaggct atgtggagag  10020
atgagctttc agaggtggtg ggtgcgaaag gccagcctcc caccctaaga tttagtacca  10080
cccactcaag cagatgcttc catctcctgt catctgggag ctcctttttt tttttttttt  10140
tttgagatgg agtctcgctc tgtcacccag cctggagtgc agtggtgcaa tcttggctca  10200
ctgcaacctc cgcctcccga gttcaagtga ttctcctgcc tcagcctcct aagtagctgg  10260
gattacaggg gcataccact acgcccagct aatttttgta ttttaataga gacagggttt  10320
tgccatgtta gcgaggctgg tctcaaactc ctgatctcag gtgatctgcc cacctcggcc  10380
tcccaaagtg ctgggattat aggcgtgagc caccgcaccc agccctagct gggaactcct  10440
tgcactgagg tagggagaaa gcaagggtgc ccttttggag caggtgggct gaacttctgt  10500
agcaactaaa gcccaagctg tgagtcaagc ctcccaagtt attctcacct ttaatgaaat  10560
gctcagtctg attttatagg gaaggaggta ctgtcagatc taggccagaa atctgcattc  10620
tgtacccccct gctcaggcca gaaatcccaa gggctgggcc cagcatgtcc cctctgtggt  10680
gggacggaca gactgccccg gtcttccaga acccttggga tacccacaga aagaggtaac  10740
gctgctctgg ccctcttctg aggacgagtc agtggagagc atgcagcttc cagctgcagc  10800
ctctctatga agggctgagg ccctgggccg ggaggctgga ggagagaggg acccagtgac  10860
cccccaagct tccaccttgc tctgttaccc gttcttgggc tgaagagaga cccaaaaata  10920
cagtgtagag attcacactg aggtaactca gggagtggaa ttcagggcct cccgctggga  10980
ttgaggtgct aatgacacaa ctcctgaacc tgaccttaga gtgccagcca ttgacgtcaa  11040
```

-continued caaagttgaa atgatgtaac ctgacgctcc ccctgcgggg cttgtgcagg ggcctgggga 11100
gggggaagga gtggccatga aactgactag tggacagaac ccagctaagg tcaggacaag 11160
acagagtgaa ggtcccctgg cactgatgtt acagaagaat tcggtggtaa ggggcttctg 11220
gagagtggca tgtgctatct aagcgagtgg cccaaatcct tcctgaaagc atttatccgg 11280
cactacagcc accatcaggt aagacagtgg gcttcttctg gccatggatg acacagccat 11340
gggggtgagc agcagcactg ccatggcagc gtgtcactgt cacatgggga ttcacatatg 11400
tacctatgtg tgttcatccc cgtgtgtgca catattgccc cacctgggga caaagggtgc 11460
ctggccacat ctggaggggc agcggtactc ctgtggccac gttggggtgg tctgcatagg 11520
tctgatgcat tggggtcaga ggggcagcct ggcctgtggc tcctcttctc tcctcacaac 11580
tccagccctg aaaagctgct ggggaggccc ttggggatga cctctcctcc ctgaggtctg 11640
ctatgggggc gggtgctgag cctggagctg tgattctgct attggatttt ccaggtggat 11700
tttctgattg aaaatgatgc agagaaggac tatctctatg atgtgctgcg aatgtaccac 11760
cagtaagtgt gctgggtcca gctcttgtgg gccacttggg ttcctttgtc ttcagggagc 11820
cctgggatgg gttgttctga gacagaggag ctcagagggt ggatgctcac ggctcctgga 11880
aatcaaatgg acataccatt cactcatttc agcaactatt tacacaagta ctttgtactt 11940
ggctttgtac taggggctgg gtatagttgt gagccagaca gattggtctc tgttttcagg 12000
ttgctcacag tctgatggag gaggctgtct agtagccaga tagattctat agagcatgat 12060
tgttgggaca gaacaagaaa tgccagctgg ccacagccct tgcatcagat gtctccgatc 12120
acccacttgc tttttgattc attttttcta ctttataagc tcctgccact gctgggcact 12180
gtgcagaatc tggaaatgaa ttagatccaa tttctttcct tgagtaactt gtggtctggt 12240
gaggggagat gaacatacac tgcaaacaca aagaactcta atataagtta catcaaataa 12300
ctgctaagta gaggtaaaag cagaaatgtg aagaaaggag ttttcctttc caactgcgag 12360
ggaagaggaa ggaccaggaa ggcttgagca aggctttgaa ggataagaaa gatttggggc 12420
caggcaaggt ggctcatgcc tgtaatccca gaactttgag aagctgaggc aggaggattg 12480
cttgagccta agagttagag accagcctgg gcaacatggt gaaatcccat ctctacaaaa 12540
aaatacaaaa aattagccgg gtatggtggc gcgtgcctgt agtcccagct acttaggaga 12600
ctgaggtggg aatatcacct gaacccagga ggtcaaggct gcagtgagcc atgattgcat 12660
caatgcactc cagcctgggc aagacagcaa gaccctgtct caaaaaaata ataataaaag 12720
aaaaagattt tggtaggtgg aatatctggg aagggcattc cagaatgagg gatcagcatc 12780
agccaaagtg tggaggcatg aaagcaaggg tgtgaatgga gataagtaat ctgggggagt 12840
aggacttggg agggcacgga gatcataaat agccacaagg ctggagaagc tccatgggga 12900
caggtcatgg agggccttga gcctgctgag aagagtggac tttgtcctct gggcagtaag 12960
gggccatcaa agggttttaa gccagggagt gccttacact gagaaaagat gacgtgacag 13020
tgagtacatg ggcaggcagc tgcagtcgaa ggtctgaaca gcatgaggga ggaggcatgt 13080
gaactgtggt gaggtgaaat tgacagagct tagcagcaga tacgagtgga gatgatgagt 13140
gtgtgaggaa ttgtcagcat ctcacacaga gctttcccct ctggaaagat cccaacagcc 13200
gagataggca gcgctgagtt tgaaatcctg gcttcatctc atctgcaaaa tgagtcaaca 13260
atccctagta gactggtttc ctggggatat ttatataaga gaacaaagtc ttctcaggca 13320
ctggcccggt gtgaagagct ctgggctttt caggagtggt ctactccatt cctaagcctg 13380

-continued ggcccagtgg ctgaaatggc ttcctcttgg aatccctggg tgcctgaggt catggccagg 13440
ggtgaggctc caggcattcc cggcatctcc acaggaccat ggacgtggcc gtgctcgtgg 13500
gagacctgaa gctggtcatc aatgaaccca gccgtctgcc tctgtttgat gccattcggc 13560
cgctgatccc actgaagcac caggtagaat atgatcagct gaccccccgg cgctccaggt 13620
gcagaggaag ccaccaggct ggaggcaggg ggtggagaga tcaccctggg cggggcagtg 13680
ctggcagcca agctgcacca tcaccgacct ctcctgtgtg gcaggaagct gaaggaggtg 13740
cgtctggacc gtctgcaccc cgaaggcctc ggcctgagtg tgcgtggtgg cctggagttt 13800
ggctgtgggc tcttcatctc ccacctcatc aaaggcggtc aggcagacag cgtcgggctc 13860
caggtgagca aacagagtcc gggggagggg gagcgagggc ctcggacctc ctgcctcccc 13920
ctcattcatc cactaggctg tgtggcacaa catggtcacc cacttttctg agccttcggg 13980
tgaagaagag gctggcgcat cctgatgggt gttcttaggc tcatagaaat caggccgcag 14040
gcaattgcct gttttcttga gtgaagctgg taacctggct gctgcctgct tccaactgct 14100
gcctccttcc agctgctgcc gctgcacttc cccccacctc ccctactccc caagagagga 14160
agacagtgat gctggcatat gaagttttgg acctgttgcc ttttaccagc agggggaaag 14220
aaagcctggt gcagtgtgat gccgaagagc atagactctg aagcagggtt agccgggttc 14280
aattctggct ttgctgttca ttaggctgtg tgacttggtg gaatgactta accctgtgct 14340
tcaatttcct catctataaa atgagttgcc gatagtactg tctacctcgt caggttttgt 14400
tagtaaatga attaatagta gaaagtgctt atagcagggc ctggcataca aatgctgtga 14460
gcctggtaag tgaacagaga gagggagatt taagaaacgc ctggaatgtg ccaggtcaca 14520
tgctcacaag cagtccttgc tatatgcatt gaacggatcg tgcccatttt acagaattaa 14580
tagaggctca gaggccagta agtggcagag ccaggattag aaactaactg ggtctcctga 14640
ctgccaagcc cagaaatctc tcttcagcaa cgcaggtgcc tctcctttgg ggtccccaca 14700
cctcagggcc tgagcagaga tgggcagacc tccaggtctc actcctacct gagcccaggg 14760
ctgtgttttt gtgtgttgag ataaaggagg ccctcccacc atcaccaaga gcttccagcg 14820
ggtttgttat caacatccca atccaggctg ccaagcttgg ggctttcaag gggctcgaag 14880
gctaatggta caagacactg tggcgtaagg ggtggaaaca gggagctgac agacaccgct 14940
ttgttctaaa tccctgtctc acggctccct ggtggtgtct gaaatttcag ccccttcatt 15000
atttctttcc tctgcagcac attttccagc tcagaaatgc agccagagaa aacacataat 15060
gagcgcctct cttggcgtca gctgaggccg cctttttttcc agggcgagct ctcttaggac 15120
aagcagttct caatgctgcc tcgatgactg ggggcgttgg ggtattttaa tgagacctac 15180
agttttacct tcctggctgt ttctcaggct tatgaattat cggccccttc tctagctgac 15240
gggttcatct ctcctttgtg ccgctgtccc tcagatcgtt atatcatcgt ggcccttgca 15300
caaagggccc tttgcagggc tccacacagg gcgagacggg gaggaaagtt gatcctgcaa 15360
cctgagccag gggctgtgtg ggaatcattc cgactggggt tctgggcaaa ttccctttag 15420
gaataagaca gggaacttta ctcagaggag cttcgggaaa aatggctgca tccattgacc 15480
tgtctggggt tcatgcttct ggggagatct catgcctgag ggcaactgga agaagatgct 15540
ggaaggcagg ggatgagcag gttcagatac agcccggctg ggctaaagac ctgtgctgat 15600
ttgacctgtg aggctgggtc cccagtggtg ggcttggacc ctcccacagg acctagtcct 15660
gggggtccac ccctctgccc ttgtcccctg ctggagatac ttggtttttg ttttttttc 15720
cccaagaata tcctaactta acctacatcc tctgccttgc acagggcagc ctgtgacata 15780

-continued caacttgctg tatattccag acctagaaaa ttattctgtg tgctttggtt ttccctgtca 15840
taacatggac agctgccttt gtgtgggact tgagggctct gacaggtggc aaggatccag 15900
agagggcagg atgcagggaa ttgcagctag gcttggccgg atgcccttct tttctacttc 15960
cagacaccca agagacacca cttgtcgatc agggagacct gacttcaaat cccacgacac 16020
tgtttactat tggggtaacc ttgagcaagt cactttacct ctctgagcct cagttttctc 16080
atccgattaa cagagataca aattcctgct ctgcagggtt gttgtgaaaa ataggtggaa 16140
ggagttagtc tggccgctgt ccttgaatta catgttccca gaaacctaga gagttcttta 16200
gtgggccccc accccagtgc cattttgagc ccttggccac tcctgtcagg tccctgagaa 16260
gactggggtc tgtgtcccgg agtgggaggg aagcgttcct tggaatagtg agaaggtgac 16320
tctgtgggaa tgctgtagag ggcaggagtt gccctagagg acccctcgga ggctgcatgt 16380
ccacccagcc cctacctacc tagacccaca gggagtccag cttgcatccc tcacgtgtgc 16440
cagcacgtct ccaaagggtg agcacgtgtg tttcgagtta agcccccagc tgacctgcac 16500
tggcctcaga ccggaacctc tccaggagcc agtctctgtt ttgcagctac tggctgtgtg 16560
accttggaca aaacctcact tccttgggct tcagcttcag ctgttatctg agagttcctc 16620
ctgccctgtg gttattaaat gaggagctcc agaattgatc cccagggccg gggtgcctgg 16680
aggagccggc agtatccagc agggggcaat ctcaccacgg ctctgtatcc agggctggct 16740
gcccagggcc catctcaaca atccactgtg gcctaagccc tgagaagaga gatctgagct 16800
gagtattcag ggatcaggac taactcatga taacaatagc aatcatgtat tgagtgctta 16860
ctgtgtggca ggcactagct gtctttacat gcacaagttc acttaattct cacagcaacc 16920
ttggtattcc ccattttaca gacgaggaaa acaggttcag acagttcaag agacttgctc 16980
aaggtcatat agctaataat aataaaagaa gggatttgaa cccagcacat ctgatgccaa 17040
agccctgtgc tcgttcactg ttctttgctt gctcccaaaa taggaattca gaggtcaggg 17100
ccacagcaga gttaaaatgt tcatcaagtt tccatatgat gggaaaaaaa aatcatatgt 17160
gtgtgtgtgt tggtgatgtg agcttgggtc aggagtcaca gaaggtcccc accccgactc 17220
agttacagtg ttgtagcaat taacagagat agggagccaa cttcctaggg gtgggttggg 17280
acaaagtccc ggtaagaata gcttaaagct gagtgaaatg tcaccctttg catagaatcc 17340
agaatctgat ggtgccccag tggagtgaaa ggggcactag agtgagggtg cagagagttc 17400
tgagatcttc tcccagctct gctgcacacc cgctgtgccc ctcacccctg tcttggtttc 17460
tccatctgta aaatggggcg acaagactgc ttggacatgc cacctgaacc tgggatcccc 17520
cgggctgatg gagggtgggt tggttgagat caaggcttat tccagggggt ggcacagcca 17580
cccttccctt ttccggagag cagtccggga gcatctggtg gtgagtctgc cccactgcct 17640
gatgctccct ccacctggtg ctccctgcct ctctctgtgg tcaaggtagg ggacgagatc 17700
gtccggatca atggatattc catctcctcc tgtacccatg aggaggtcat caacctcatt 17760
cgaaccaaga aaactgtgtc catcaaagtg agacgtgagt gaggccagag cagggcagta 17820
ctccataacg gtgggaggga gggagggcgg gggagcaggg cagtactcca tgacggtggg 17880
agggagggag ggcgggggag caggtcagta ctccatgacg gtgggaggga gggagggcgg 17940
gggagctgtc ctaacccctg tgcctttctc ccgcagacat cggcctgatc cccgtgaaaa 18000
ggtgagaggc ccctcctctg caggccaact cttccctgtg ggcccaggat cctggtacag 18060
ccctggggtc cggctcccac catgccagcc ctgcttctgg gccagtggag gctggaggct 18120

-continued ctagacatgg tggatctgga tgtggggcct ggttcctcaa acgtctctcg ctaaccaccc 18180
tcccatctat tttcccttcc catcagctct cctgatgagc ccctcacttg gcagtatgtg 18240
gatcagtttg tgtcggaatc tggggtaagg gccagacctc ctgtgatggg gtttgggtgg 18300
ggtcatcttc aaggaggggt ggccggtcct gaagggaggg cttgctctag agatgcaccc 18360
tcaggggctt cacacaggct cccagggcag ccagcacacc gctgtggggc agcagccctc 18420
ggccaggccc agctggtgca gacacatccc cagggacgga atgatgatct ggctggcgtg 18480
agttcagcag tgctcgccct gcagatccca caagctcaag aggccgcttg cacgcatgtg 18540
gacactccgt gattctgctt ctatctctct ttcagggcgt gcgaggcagc ctgggctccc 18600
ctggaaatcg ggaaaacaag gagaagaagg tcttcatcag cctggtaggc tcccgaggcc 18660
ttggctgcag gtgggtggca ggcatgccct ggggtcattc gtggccagtg caccccagca 18720
ggcccctatt gccctcccct tcctcactgc cacttccgag gaaaccttgc ccaccagggg 18780
tgtgactgtc catgggtgat gatacttttt ttgttagata cagggtctga ctctgttgcc 18840
caggctggag tgcagtggca tgatcatagc tcactgtagc ctcaacctcc ccagctcaag 18900
caatcctccc acctcagcct cctgagtagc tggatctaca ggaacacact gccataccca 18960
gctaactttt aatttttttg tagagatgga gttttgttat gttgcccagg ctggtctcaa 19020
actcctgggc tcaagtgatc ctcccacctc agcctcccaa agccctggga ttagaggcat 19080
gaagcaccgc acccagcctt ggtgttgaca cttcttggtg cctgatttcc cctctgaact 19140
tcatgacagg cctttagggc cagagggtca tctctaacag agcccaattt acagatgagg 19200
aaattgaggc ccagaggcag aacagtgtta ccttgtgggc ccttgagtca ctgcaaaagg 19260
agcctgtttg gctggtcatc tctgtcacag ctctcttgtc acttattaac ttgttggctt 19320
ccttaagagg cagacaggga attccgaaca gacactgggc cacacggggc ttaagcatgc 19380
aggtgccacc gttactcaga tcccagttcc agccctgctt tcccacttaa gagctctgga 19440
accttgggcc agttacttaa ccactttgag cctcagtttc tccctctata aatgggcgat 19500
aataattccc acatcacagg gtggttgtgg agaaagtaaa gtgccaaact tagtacctgc 19560
taaatagtaa gcagttggta aatattagct attattattt aagttatccc tgttctttcc 19620
tttcattcac atttattcaa tgttttgtgc caagcacaag tgataaaaag tcccaccttt 19680
ctgggagaca acagcctaat ctagaagcca accaagtaaa tagttataat atagggtgat 19740
agggactcga acgggactac attctgcgtc caggatggca aataggtgcc atctctagtc 19800
aatgagtagc agctccctgg agtgctgctt tgaaaagcat tctaaagctg tatccaggat 19860
tgtgggaaag agtgctgtga tcaatgagtg acttctgcca ccaatctagg aaggaatact 19920
aacagtacat gtaccatcct tgccgtaaat gtcataggag cactgagaac agagcggcta 19980
gtttagtctt gggatagaat aagggatctg agccaggcat ggtggtgcac acctgtagtc 20040
gcagctaggc tgaggtggga agattgcttg atcccaggag ttggaggttg cagagagcta 20100
tgatcacacc actgcactcc aacctgggtg acagagcaag accctgtctc taaaaaataa 20160
atttaaaaaa ataagaggat ctggtaaaaa ccttatagaa gggatagcat ttgagtctta 20220
atggatggac aggaaagtgc tagaaagaaa gaagaaacag catatgaggt atattaggtg 20280
agaggttggg taggaagaat tacaaggatt tttctgtggc tgttgcccag ggtagcagta 20340
gaaatcaggc tggagaggga cacagaggct gaagaggtag gcagtcaagg gccttcagtc 20400
ctcagctcat gagtgacctg tatcctgagc actggacatg ggttacctga atcccgagca 20460
cacatttccc acctcccgca gcatttccag cggccccatc cagaagcctg gcatctttat 20520

```
cagccatgtg aaacctggct ccctgtctgc tgaggtggga ttggaggtga gtgacgctgg  20580
gccggcccca gtgggggccc actggaaatt gggtcagact gtgatcccgc ggtgacaggg  20640
gcaggtgcct ttccacatgg ccctctttca gtggacactg agggagtagg agccctaccc  20700
accctgcaga gaaggcttca cagactgggg atgtttgacc cttctgcagc cttccccagc  20760
tctgatagtt gttggtcacg agcttgggaa tgtcgtaatg gtaatcaaag agcggacctt  20820
cagtgtccac ttgcatcaga cattgttcca tgccctttac acttcacaag aatgctgagg  20880
gttaagtacc accattatcc ccactttaca tatgaggaaa ctgagaccca gagaaagtat  20940
atgatttttc caaaatcgtg tacctcatat ggtagggctg ggattcaaac ctaggtggtc  21000
caatcccaaa gcaggaaccc ttaacctctt ctttggacaa gttacttcat gtctgtttgc  21060
ttacctgtaa gatggggata atacaggctt tcttccaagg ttgttgtgtg ggttaaagta  21120
attaatatgt atactagagc tgtgccaagc acattgtaag tgatcagtga atgttagcta  21180
ttctgttatg acgattcaac acagcctgtg ctaaatgaga agctcaaagg ttcccgcatc  21240
tgcaaactgt gatttttaaa gcaaatgtca tcaaatttag ccaaagaaat gaacatgtaa  21300
tggtataata tttgatagtt gataagatag ttatgaagta ggggagtgcc agggtcagct  21360
ttaagccctc ccagagctcc accagagctt tccaactgct ccattcatca ggaggagctg  21420
aggtactgcc acttgaagat ccagcatctg acccagagcc cctgggggag cctgtcctgc  21480
agatgagcga gtgtacagat agcgcaaaca cactaatctt tctccatttc cccaccagat  21540
aggggaccag attgtcgaag tcaatggcgt cgacttctct aacctggatc acaaggaggt  21600
gagatgtggg ggtcttcacc tgttggccct tgtcatctcc acaccccact tctcatcccc  21660
accaccctgg agcctggggc cttctgtgct ctctgcctgg actgctgtgg tctgtcaggc  21720
ctcggcccac tgtccttctg tccccacagg ctgtaaatgt gctgaagagt agccgcagcc  21780
tgaccatctc cattgtagct gcagctgtaa gtccagaatg agctggtggg agccccttga  21840
ccttcatccc cagcccctct gacctttgat ctctgccaca cactcccagg gtggctggtc  21900
tccttccctg aagctctgac agagcagagc gagaggactt ctgcccagca agaagtttgg  21960
gtcagggatt gcgggagccg cagtgcctga tggtgctgag aagaccacct gcatctcggc  22020
ccccaggggt gtgtcagggg atccccaggt tccccggggg ctgagcaagg ggcctctttt  22080
ctcccatgag ggccgggagc tgttcatgac agaccgggag cggctggcag aggcgcggca  22140
gcgtgagctg cagcggcagg agcttctcat gcagaagcgg ctggcgatgg agtccaacaa  22200
gatcctccag gagcagcagg agatggagcg gcagtgagtg cagccagccc tggatgccct  22260
gtcccgcctc ccaccccacc acacgacccc acctagcttg cttcctgccc gctgtgtccc  22320
cagccaactt cctcctcctc cctggaggcc agtcctcaga ccagatgagt ttggtggtag  22380
gtcagcgtat ccatccttgg cctcagacca cctggctcct tcctccttgc tgagcagagc  22440
cccctgtctt ccaacattcc aagaatatgg aaaataagca tcctactagc agtaggctct  22500
agctagctag gattagctac cagctaacat ttgtcaagta cctccataag gctggtgttg  22560
tattagggcc ttgtttatgt ttcttaattc ccacaatagc cctgggaggt agagagtatt  22620
aaccccattt tagaggtgtg gagactgaca ctcagagagg tgaagccact tgtgtctaac  22680
gtcacacgtg gccaagctgg gatcaccccc aggcaatctg gcaagtcccc acagggctgc  22740
cctgcctata gtgatgaagc tcacccttgt ccaggaggat tgaaatgatg gcctaagaga  22800
ataaatgggg tgagcaattc ataaatcaaa aactactgtc aagatccaaa tccaaatacc  22860
```

-continued

```
ttttaggcat ttaaaagtat ttcatggctg gacgcagtga ctcacgcctg ttatcccagc  22920

actttggagg tcgaggccgg cagatcatct gaggtcagga gttcgagacc agcctggcca  22980

gcatggtgaa actgtgtctc tactaaaaat acaaaaaaaa attagctggg catagtggca  23040

tgcgactgta atcccagctt ctcgggaggc tgagacatga gaatcacttg aacctgggag  23100

gcagaggttg cagtgagctg atatcgcacc actgaactcc tgggtgcaaa gtgagacttt  23160

gtctcaatca atcaatcaat taatgtattt tgaaaaggaa agaggaaagg ctgtccccat  23220

ctcccccaac acagagttag ctgggagtat tccacctggc taggagcccc tgctttgctc  23280

ctggggtcag tccaggcccc gcctgtcatc agtcacctta cctaagtgtt tggaggaggg  23340

tgcatggagt gtggccttca catggatctg cttccctcct cccacagccc agcatctctg  23400

ctcagccatg ccagacaaaa ccacgcaaga gcacagcgtc cagactttgt tagataacgt  23460

cccccaaaac caaagctggt ccaggcctcc taggaaggga gcctggagaa aaatccaact  23520

tttctccaaa tcaagaattc acagtaagga agagttcatt tctcttgcat agggccaaac  23580

atgccaatct gcatttgtgt ttcagaagga gaaaagaaat tgcccagaag gcagcagagg  23640

aaaatgagag ataccggaag gagatggaac agtgagtacc tcggctccac gcgtgtctgt  23700

gcatgaacat cagtgtgctc aggggagtgt ggccaaccag aggctgcctc cagaaccagt  23760

ttacctggtt ctctcatccc ctggtgggtc ctcctttatt tgtagtaaag cctgtcatat  23820

tatagtaact gaaacatagt ctcgtataat tgccaaggtg gggttcacac tcaatttaga  23880

atacaagctc ggggactttg cttgattcat catgactaga accatgaggc ttctccccag  23940

gctggctggg gctctccgat atgcaggaga tgggcctatg gggttctga ctccagtaac  24000

aggcatgggg gtctcatttt aggattgtag aggaggaaga gaagtttaag aagcaatggg  24060

aagaagactg gggctcaaag gaacagctac tcttgcctaa aaccatcact gctgaggtac  24120

acccagtacc ccttcgcaag ccaaagtgta agtttcatga gccgagggga gaggctaagg  24180

gaactagtca gaaatgctgg ccctccctcc cctcaccacc acctcctaga tggatagccc  24240

ttggtgctct gggctgtggt tccttcatgg aggggcagct gtgggtcaga gaccatctgc  24300

cccagcatcg aggtaggagg gatctgtctg ctccccttgt tcacgggcca gctccacata  24360

cccagctccc aggtccccca caacactgac atgggcaggc tgtcaggctg ctgaagaggg  24420

aataagggcc atagtgaaag tggattagct catgggatta ccgtcctaat gttttgggta  24480

ccatgtcctc ctcctacttg gttctgaaca ggggctgggg tgaagccagc agcagaaaag  24540

aggggaagga cctcacatca gagaagggct ctggtggtcc aaggttgatt cataactgtg  24600

ggaggagctt actaagtgtc tccagcccct atatccctgt atgtggacca aggatggagg  24660

caggaacagg acaaggaggc ctctcccaga cacccagcta tgggctgtgg ctgtgctgtc  24720

ctggggcctc agctcatact ctccttacca tctcctctct tcatccgtcc cacatcctca  24780

cctccatttt cagtctaagc ctctaccacc tgctccctga ccaccttctc aaccccagct  24840

tccatatgcc tctttaagag gcagcccaca ctgccagagg aaaacgggga ccatgacaac  24900

cacaagtcca ggattgctgg ttgggtcctt actcctgcct tccagctgtt ttgacttata  24960

gttgacacag gacaggtcct actccagctg attgtgctca gctgacctgg gaacctccag  25020

caaggggcta ttctggactc aagagcccag gttccccatc tctgctgtgg ggcagtcatt  25080

tggcatgttg tgatggggtc tggacagctc tgtccccaac tttgggtcac atatgagacc  25140

tatgggaatg tcaacctgcc aacataggcc acttgcacca aggaagaggt gcagggcatc  25200

tggatggttc catttcaccc ctccctggtg cagtcaaaca gctcccaaca catttcttcc  25260
```

```
tggcagcagg gcagtgtcat ctcctggtcc tctcagaagg acaaagcaca ctctcatcag  25320
cctcccccgt gacattcagt atcagttgag gatatggcca gagctaagat cccaatgaat  25380
gatcgctgtt ttagacagac agctaatttg ctcttacgag tgaaatagga gcttcaggag  25440
agaaatcgat tttaattgct tctcatggaa gtaatcctag tcaatttggt accttccaag  25500
aaattgggcc tcagcttcac agcaaacaca ccctctcagg agcaatagaa aataaaaacc  25560
ctttcactag ctggttattt atttagtgcc ttttaaacaa atcaagctct ttgaataaaa  25620
agaccaagaa ttttgcattt gctcaaggta aatgtgatct taggcagctc cacaaagcac  25680
aggatggatg acccccgcct gcccgctgag ctgggacagc tgctgcctct atctgtctct  25740
gtatgcacca gcaatttaat tctcatttgg acctaaggca ggaaatgcag tgaggtccct  25800
gagccagctc acctcctgcc tcactccctg ttccccgggg tctagcatgg tcagggctga  25860
gttggtccag caggcctggg ccccagccag ctcctatcca accacccttc aactcagcac  25920
ccagtttgca ataggttata cctgactcag gcttctatgc ctgcaagggg tgggccctgc  25980
ttttttttt ttcttgagac agagttttgc tcttgttgcc caggctggag tgccatggcg  26040
tgatctcagc tccccgcagc ctccgcctcc tgggttcaag caattctcct gcctcaaagc  26100
ctcccgagta gctgggacta caggcatgcg ccaccaagcc cagctaattt tgtatttttg  26160
gtagagacag ggtttcacta tgttggtcag gcaggtcttg aactcccagc ctcaggtgat  26220
ctgcccgtct ccacctccca aagtgctggg attacaggca tgagccactg tgcctggccc  26280
cgggccctgc attttttaaa ataaaagagc atggggcatc tcttacctag aaaatgaagt  26340
cactcatcct aattatgtgc ctgggactga ctgcccccca acctgcccca gggggccctt  26400
aaaattgctc ctgcccacct acccgtggct gatccagcag acccccaaca ttttgccaag  26460
ccctgaaggc caggacacca ccacagaggc tcctaacaga ccttccctta gcttaggcag  26520
gagttatgta ggtggttatg caggagttgc caggggcagc cttgactaag gatctggtag  26580
ctgaaggatt cttgaaagat ggagatgttt aaataggaca tctccaacct tctctcccta  26640
tccaaggccc catcaactat ctcccccacc tccaccacaa gagaccccac gatttggaag  26700
ttgaggttat tttcctaccg aactattaaa taatcatttg tgttccattg ttttattaag  26760
tagtccttgt tagtaaggga gcatcagggt tccactgttg ggtaaatgta atttgagcca  26820
agagccaaag aacttaacag cctttgcata ggccaatggg caagttctgt taagctttta  26880
aaatattaaa aagcagctca caagcaaacg ggtatactac cttccagagt cctagggagg  26940
ccggaggcca gagtccaagc tggaaactct ggaatggagg gtttgctctt ctctccacat  27000
tatgtcaaaa ttcaggtctt cctaactgca tgtacccctt ttaccttttg ggatgtcccc  27060
acctcctcag gaccttcagc ctccatctgc tgcccacact gttcagacat cccctagggt  27120
cccagagctc caaggcaagg gtgataagca caaggctgga gggtctgttc tcccattgca  27180
gccccttgcc ctcaaacgtg tgcgattctc agatattccc atcctcctca ctgcacttcc  27240
cagccttcag cccaataccc tacaaaatgg ttctcatgct accctcagat ctgagtttcc  27300
tgttgttagc cctttgtaca gacagaaaaa ctaaagctgc caaggttgaa aacactgtat  27360
gcaccagctc agagcaaaaa acctttgctc tgctctcctg aactctgtcc cctgcccctg  27420
acctcacagc tcccatggag gaagctgatt acaggtcccc aaactcctga gaaggttctc  27480
cggcctcttg ggctcccaag tcccttttgg ttcaccagct tcctcctctt ttccctgggt  27540
agatgatcag ggagtggaac ctgagctcga gcccgcagat gacctggatg gaggcacgga  27600
```

-continued

```
ggagcaggga gagcaggttc gcgtccccgc tttgctccct ggcctggctg ctctgcttta  27660
ccctgcccgc ctcctcctga ccgcagtgca gacacccagc ttcaggggcc cagcatgtgt  27720
gggggccaat agagtctgta aagctcctcc aagccccagc ttggcccaag cactgtacac  27780
aaagcctaga cgacaggact caatgcccag gctggtagat cagctgttgc acactggtac  27840
cactgaaccg ctggctcgaa tatttagata ttgccaaatt ccccctctgc tgctctggcc  27900
cctcccccag gaccccctag accactctca aatccagcaa ctgaggaggt agtgtctggt  27960
ccagcaggag gctttcagca tcctgttcca gcactcaggc tggtccgggg tgggtaattc  28020
agccatcgct cttggcccca gggagcttca gattgggggt attactctgt ggagctgcgg  28080
cctggggaag gaagggggct ggtgcactgg ctatctggcc tggatgagga tctgttttct  28140
gggggcacat ctcctgcccg ctcctgctgg agctgtcctt ccaagagctg tcccagccac  28200
tgccttctct ttgaatgttg aaagcggagg acttgacctg cactatgaga caagccagtt  28260
ttgttctgtc gaacaacagt tctaggcaga cacccaggct ccctttttgtc tcgagccatt  28320
ttttgtatgg agggaccaga catgggttag aaaaggcctt gttctctttc aacaaggctt  28380
tgtatgtgaa gactgtgatt tggaaaagct catccttcca caaggggttt tctctttgat  28440
gttctggccc tgacttctga aaccagtgtt ctggggagag gcatttgaga gtgacccagg  28500
gcctgggaac cggggctttt ctcggtggtc ttaggcctgt tctgcaacca aggcaaggcc  28560
aggtaagccg agttggacag agggtgcagt tttgctgtcg gatctgccaa tgctgtttat  28620
ctcacaaagt catgcattcc ttgggaaccc agctcccatc tgctgcccat ggatgctctg  28680
gctgagctga actgtgtctc atcattttgt tatctgtgtc ttatagcttt tggatggttt  28740
tatcgttacg atggcaaatt cccaaccatc cggaaggtag gacagggttg ggtgctgtgc  28800
tggtgtgctg cttagtttgc tgtgggtttt ggcttttccc aaacattcct tgtcctatca  28860
acactaaatg gtgtgacttg gcctgttcac ttggaaggct aactccatct ccatctttgt  28920
gtcaggctga catcaaatgg cagggtgctg ttgcaaaggc aacattggga gagggatcca  28980
tggtgtgaga cctatccaag taccatctgg cagtgtgtgc atcagcactg gccctgatgg  29040
gaacaggaaa ggggcaggaa gcttctcctg tgtttctctg tcaagtagaa ctagagacca  29100
aggccagaag cttggggtca gacagagcaa attatcggag tgggtgtacc tagtgcatgt  29160
tatgagacca gctgtgccag acgcagcctg gctgacgagg tggggatttg ctgcctcagg  29220
ttgggacaga gacccactcc aagcacagcc ctctcctagg aatatctctg catgtgccca  29280
ggataatgca tttttccaat ttctaggacc tttaattttc tctctaaatc ttattacaat  29340
atctccaggc cttgtaaaac tctcttgtcc ttatctttct aaatcacatt gacatttgat  29400
tgtgaaaaca ttgctgttaa tatctataat tggacattcg agatgacttg gtatttggag  29460
gtcaggcagc agcataaatc tgggtgagct aaattggatg ttatcacttg accagcgctt  29520
tctggcaaga tgtcagtccc ccagaaacca gagcactggc agctgagtga ccttgatgat  29580
atataattct ccctgcctgt aaaatgggaa tattaactgt gccaggaaaa tctacccccct  29640
tcctccagca cattgctatt aaaataacaa acagtaatat ttttcctgac agaggttaat  29700
gcctttatct aggaacatct atcaggattt gtatagcatt gaataaactt ggaacagagt  29760
tcctctggga attccttcac acattgtcct ggtctcagaa aggccttggt ctcataagac  29820
tatctgtttc ccttgacagg ctgactttgg tggcttagga tgcctcattg ggttagattt  29880
ctaattcttc tctatattct gcctctacta gaactcagct agagaggaca aaacacacac  29940
acacacacac aagcacacac acacatgcac acataggatt ttacttgaaa aaaataataa  30000
```

```
aggagacaga tatgtcaaat ctttttcagg cactaataac atgtaaatgt aaaagaacta  30060
gaatcttctc cacataccac ctcccatcag aaatcatgtc cttgaaagtg ctgttgataa  30120
agaaataggg ttgcctttcc cctattcctt aatctaatta ttccagaaac agctgtcatt  30180
ttggttttca ttttcacttc aaaaaaaaaa aaaaaaaaag aattgcttct gggtagaatc  30240
aatagcacaa tcgccccatc tgcctcacct ctcagtctgg accaaaagga atattgtaac  30300
tgacaggcca tggatgtaac tgacagctga aaggacaaca gaaccatgcc cctcatactg  30360
gctctgaaaa cccgtcatca ttttttctag agccgtgaga gactctttgt ctcccagcag  30420
ctggaacgcc aagtctccag gaaatgcaag tgggtatcca tggccatgat atctgtgcat  30480
aaattcccct tatttaaaaa tataaagatt cagctcatgt ctataatgcc agcactgtgg  30540
gaggccaaga caggcgaatc acgtgaggtt gggagttcaa gaccagcctg gccaacaggg  30600
tgaaaccctg tctctattaa aaattcaaaa attagctggg tgtggtggcg catgcctgta  30660
atcccagcta cttgggaggc tgaggcagga gaatcacttg aaccctagag gcagaggctg  30720
cagtgagccg agattgcacc actgcactcc agcctgggtg acagagcagg accctgtctc  30780
aagaaaataa taataataat ataaagattc agtgtcttct atttccacct tggcagtaaa  30840
tccctctggg gctcaaggtt cccaggcctt tggccccaca gaatttgtgc cagggcatga  30900
aggattcatg attctgacta agccctttca tcagaattgc ttgagtcact cacacagacc  30960
agccctactt gcaggagccc accgtctggc agggaaggca gattcacaca cagctaagta  31020
acctgtgtgg ggccagtctg agatcagtgg gaaatgccat ggggcaactt gccctctgca  31080
tctgtacaga tatgactttc ttgggcatga gacagaaact gtctactacc ccacccagaa  31140
gccctgactc tataatctta gcactggtag tttttttttt ctttctttct ttcttttttt  31200
aagcaacaga atggccatta ttctcgtggt ggtcctggag gaggccaggc tcttactcta  31260
gcaagctacc attaggcagt gtttctggct cctcttggga aattgctgtc tgaatctcta  31320
ctacgatggc agggattcat ctatcaactg agtctagtga acaaggtagg caaggaacca  31380
agcaggactc tgaagcagtg agaaccattt tctcgagagg ctcatacact gctctggagg  31440
tgggtcccag aggtgaccat ttccagagca cattagcagt acacagaggt gtgtgtcttt  31500
aggagaggag ctaggaagag tccctcagag gtccataatg gcccaccaag tccctccagc  31560
tgtggatgaa tgttgtgtgt ccattgctag ggagctcaat tccttattcc tggccttgga  31620
tactaagatg attcagaaaa ttcaagagca gatccccaga aggcttgttg ggggcggggg  31680
tgagctcagt gaacaggggg tttcctcctt gccccagaaa ttgcccaggg tgtgggctgt  31740
ctctgctgcc cctctcctga atgctcgctc tgtcctccac gctgtgtgtg ataggggctg  31800
accctccctc ctgccgtgtt tcccttgccc ccagctcatc agggcaccat agaaaaaacta  31860
ggacctcgaa gactcaggtc caaatcctgg tactatcagt tacaagatgt ctgacattga  31920
acaagggact ttacctctct gagcctcagc tccttcatca aagaatgagg ataaacctac  31980
ataggagatc attggtataa atcccttggc acataggcag ttcataaatg atcattctct  32040
tcctgcctta gcccctggct tccctgcaac cccatgagag aagcagccag gaatgcaggc  32100
tcggtgggtc taattcctac aggaaaaata aggagtctat ttgcctttca tgtccctccc  32160
caaatcctct agaaccctga tggtgagtgt aaagcagtta agccattctc tccatgccct  32220
gcctcccagt cctgcagttt ccagctagcc ctcggtagag gggcacaatt cagaggaaac  32280
tgtgggtcta gactctccag ggtgaaatgg tccagagctt aagcatgcgg gtaaaatctg  32340
```

-continued atgtccctgg gtctgagccc ccaggtctca gtgtgactcc tatcacttct agcttaggac 32400
gggacctcta cagatgaagc ttgccagccc tcccagattt tctctggaat ctcccaggat 32460
gcatctctga atctgaacat gagatgatgc agaaggcatg tgccagatac tggaaaatca 32520
gcacaatgcc ctttatttat atggcactta tttatttttt tattttattt tttatttata 32580
cagaactttt acaaagttct ttcatggatg ttatttcatt ggcactgggt ggcaagcctg 32640
tgggggaggt atttttacca ttttggagat gaggcaaatc aggcccagag aggttaagga 32700
acttagccaa ggccacacag ctagttagtg aactaataag ccagtctttc tggctggtaa 32760
agagaatgtg tctcccactc tgcagtaggt agcagtggcc ttcctgtcct aaacctgagg 32820
tctgatgtcc agagtggtga gagagctggg ggaggggctc accatgggat ggttgtgtta 32880
tgtgaggact ggatgccccg tgtgctgtgc tgtcgacact atttctaacc tttgtcatat 32940
aaacaatgcc acatctactc agaaaggaaa agataagaag aaagccaagt atggcagcct 33000
gcaggacttg agaaagaata agaaagaact ggagtttgag caaaagcttt acaaagagaa 33060
agaggaaatg ctggagaagg aaaagcagct aaagatcaac cggctggccc aggaggtatg 33120
tgtcctgcct gcaggccagg caagcaaccc tgggacacaa tgtggtcgtt ctccatgtgc 33180
tcccagagga ccagctggag ttgttctcct caaatggcat acaagggtgg agtgagccct 33240
ttcctgctcc ccagcctgga gagagagatc atgccacctg cccagggcca tctgaggtta 33300
gctcctggct taggaattga aactaatctc cttgcttggg ggtgtgagtc ttgctcctgg 33360
ctttggaatt gaaactagcc tccttggtcg gggggtgtga gtctgaggtt agcctttctg 33420
accagatggt aggtctcagg ttagcctttg atacacctgg cttagagatt tgagtctgtc 33480
ctcttcactc taccccacca gagtctaagg ctgggcctct ccatctcagg tgtggctctg 33540
aggctactta gagtatggtc tgcggctaac ccttctgcct tgcttgtagc tttgaagtta 33600
ggcttccact gacctgtcta cgagtctgaa tcactctggc ctcccttccc aggttattgt 33660
aagaccagac cccccccac ccaacttagc ttggctctga gaatatgggt ctgaggctaa 33720 ccccttatg caggtggtag gtgcgaggtt atctcccaat taatcaggct atcagtctaa 33780
ggctgctccc ctcaacatag ggtgtgtcta aggctagacc tcatcaacct gggaatatat 33840
ctgaggctgt ccccatgaag acatgtccaa agcaacctta caccatgaat aattcctatg 33900
ctaggtgaga tgggtaacct taactcccca gctgtaggag gtatcattgt ttctgcttct 33960
ctttaacgca tccatgaatc agaatgccaa tttgattaga ttataaaacc agagaagtcc 34020
tggaaaatgt gaaatgcatt aggtctgaca ttatgaacaa attagccaca aaattaaaaa 34080
taagattgaa cttatgcttc tgagggcaag gcagaatgga gcaggaaaaa aaagagtcaa 34140
gttaaactct tggaatgtgc tgggggaggc tacaaaaact ccattcttgg aaaatcataa 34200
gagcctcagg gttcatgggg atctgggatc cagctaatcc ctcacaatac ataagcccct 34260
tttctgattt tgcctacaag ttctgcttag tgaatttgac accccgccac tctcttctcc 34320
cttgctgctg cctccttgag ggccagttgg aacaagccca ggtctctttc tagatagctg 34380
atgcacctca cagtactctg gagtttctaa aggagtgctt tcatgctatt tctatccaca 34440
tgttattcaa atgtgccctt tgtcctctcc tttctgcgcc gatcctgggt cccaggtgtc 34500
tgagacagag cgggaagacc ttgaagaatc ggaaaagatt caatattggg tggagaggct 34560
ctgtcaaacg cgcctcgagc agatttcctc tgctgataat gagatttcag aggtaacaga 34620
gcccttcttt ccacatagac cctcctgctg tcttcagaat gacccactgt ggggacagcg 34680
ggaggtgaga tgacaactag caaacgtcac tagcctcaca gtgcccatcc actgtccagg 34740

```
cccaccccta ccaccccact cccctcttga ggaggaggga tatgtctgta tttctgggta  34800
tactcccaga gtgatctcta agtcccagct catctgcgat agtctcagtt aggcctgttg  34860
tcctggcatc atgactaaga gtccccctta cactctcaag ggcattccag tttagagaat  34920
gaactctgtg aacaccttac cacccacaga tggcataact tggggctctt ctgcatttgg  34980
gcactcccta acagcagcct agtatggcct cagctgggca tccaggtggc agaggaatgg  35040
cgccccatgg ttctgatgta agggtggtgg gtctccagta gcaagagaaa cagattagaa  35100
gagcatagtg ctcgctgtat tgtgaagtgg agctctaagc agagtgacaa ttacagaact  35160
tccttgcaac acccccagat gaccacaggg cccccgcctc ccccgccttc tgtgtctccc  35220
ctggccccac ccttgagacg cttcgcaggc ggactgcacc tgcacaccac tgacctggac  35280
gacatccctt tggacatgtt ctactatccc cccaagactc cctctgcctt gcctgtgatg  35340
ccccaccctc caccctccaa cccaccccac aaggtcccgg cgccccctgt ccttccctta  35400
tctggccatg tgagcgcctc atcctctcca tgggtgcagc gcactccacc ccccattccc  35460
atccctcccc cgccatccgt tcccacccaa gacctcactc ccacccgccc actgccctcg  35520
gcgctggaag aagcactgag caaccatccc ttccgcactg gggacacagg caatccagtg  35580
gaggactggg aggcaaagaa ccacagtggg aagcccacta actcccctgt ccctgaacag  35640
agcttcccac ccaccccaaa ggtaatgtcc ctgttctgca tgctatgttt ggaagtagga  35700
agagtgggga gaactgctgt ttcccatgtc ctccactgct cctgagagtg gagacagaaa  35760
gaaacatcat ctcaccccat tttccaggaa tgccccctcc gtgtgcatgt gtggacatcc  35820
tgcatgtata tggtggttct cactgatttt gaagtgctgt attgtatggt gaatggcctg  35880
ggacctttgg ggtaagcaac ggtgtgtcca tttgatattc attgctctct cttagctctt  35940
ctttgctagt gtaggctggt aactttcaat gtaggacttg gaagtctatg ttaatgaata  36000
gccagcactc tgtcacatcc agtcacttcc tgatattatc ccagaaagcc ttgaatatgg  36060
gaaatggctc ctgatttaac gggaaaaaaa gggaggggag gaggaagcag gggcgtattt  36120
ggctctgtaa atgaagtgat aacactgtac catcaaatgc agtattagga cattccagtg  36180
ccattttcta cagtactggc caactgcact ggcttgaagt gtaataccca gaaatttctg  36240
gccaatttcc agctatagaa aaaatgaaga tgagagagtt cctagaaata atttactatt  36300
aaaagaatag gaatgttttt cttggatgtt aggaagatga acagtgtctt tctgaaaaag  36360
acatatttct tattaattat tcgtaatcca aagactattt tgaaacatgc aatctctgag  36420
gaagacaggg agcttggatc ccatgaaggg aaaaacaaaa tattattcca ctcccgtagc  36480
catgaggcca ggcttgagtc agtgcaaagg catctcatgt cagctgaggg tagcaggggt  36540
tgctgaggga gggcatagtc aatagcacct gaccagtggt tttattaac cttccctgca  36600
tggatttgag ttcctgcgtg gagagcagga caagcatctc agagcactca ggagagctta  36660
caaggaaggt gggagtgaag aaagtgccag atgccagcaa ggctgaagct tccagcggga  36720
gactctcaga gggacccttt ctggacctct ggttggggtc gtgagccctg cagctttgac  36780
aggaagaaat ctgcctgttc tcgggacatc tttccccaga gcccagccag gagctggttt  36840
ctagagctga gttagccttg cacaacattt ttctctgtaa gtggcctcca tcaagatgag  36900
cagtagcttt tcctcaacaa atttgattcc actttgattg agtacctgcc tggggcctct  36960
ctctgtgaag gggagagggg agcagtgctg aagaggatgc agaggagatt gacatgcctg  37020
tgctttccag gactttgcca tctgaaggat gagctgctgc ccaggcaggc ttctgctata  37080
```

-continued

```
aaatatgcat aagccatgcg ctatgggagg gattcattct aactgaagat tgaagacacc  37140
tctgtagagt agagggctta cgagctgagc cttgagggat ggcaacacat ggaggatggg  37200
agcaagggca ttgcaagtgc agggaacata aagatggcaa gttggagtag cagggagttg  37260
gcctgcctgg gtttgaatcc tggctgtgcc acttactagc taggtaactg aacacatgct  37320
acttcatcta tctgagcctg ggcatccctg tccaaaaata ggaatgctaa tggcagctac  37380
ctattcgaat caaataagtt aatacatgga cacattctaa gttaagaatg gcaagagtgg  37440
caggcacatc gtggatgttc agtagacatt aactatggtt attgatagtc cagagtaaaa  37500
gaaaatttgg gtgaagctgc aaacctggga tcttagcaat ctcagtgtca gcaaaacttt  37560
gagtcaggat caagattcaa gacagagtcc agacttctca gattcttcaa ggcatcacca  37620
agttcccact gttagttcct gatcagagcc cagggaaggt taaaagcccc ccaacacaag  37680
gagcctctga agaactggac tataaatgtc acaagcgaca tcaaagccag ggttgtccca  37740
gcctcaaaag ccagggggct gttgcttggt tggcttcatt tggcccacct ctcacccttg  37800
taccacccac cctcctcctc cctgcatgcc cctggcaagc tgtcatcagt gctgcagcag  37860
gaagtgtgag tgaccacacg cccacacagt cagcccagcc accagcaggc cccaagtcat  37920
ggaaacaaac acctgtgttg gcttgacact tgtgcctgcc acaccagcac cggccatagg  37980
ggggttttca gggccagatc tatccacagg cactgtccca tgttctcacc atactattta  38040
gtcattcatt tattcattca acacatgctt attgagcacc tactatatgc caaggcacta  38100
tgcagggcac tgggaatccc tgctggatag acagctgcag tctcccttct caagacagtc  38160
tggtggggaa caaagaaaag taggcacccg ccacaccatc agcgtggaga cggaggaagc  38220
acaggtgcta taataaggaa gagggctgga gtagaggaaa agctcaaggg aggcttccag  38280
aaggcagtga cgcccaactt aagacctagg aggcaaagcg gaagaaggaa gagcacgtgc  38340
aaaggcctca aggcaagaaa gcctggcatt ttttgaggct aaagctaggc agtgtgagga  38400
gcgtggcgag gagtgagaga taaggctgaa aaggaagcta gagaagctca tgaaaggcct  38460
tgggagtcaa gccaatgagc tcagtagtca atgcggacac tggggagggt ttgggggcag  38520
ggctgtgaac tgatttgata catcttgccc aaaaagatca agtgggttag agccaagcag  38580
acaggttgcg tcagctcccc tggatgcctc tcttactggt cttcacccca tggcccctag  38640
agactatgtg cctaccaact aggaacagca gatgcttcac actgtggtcc agggactgga  38700
actgtggcca aagagacagc ccttaaagac aagggacact ggatagcacc catggccact  38760
gagagaaggg tctgaaagtg tgtctcctgg gtgacactgg ctgctggcac ccccaagcca  38820
ggctctagct caagcgtcca atttcttaga gccgctcagt agtttctgtg atctcagccc  38880
acactgtggc caatgggctt ctcatctctc tgctgaggat cacaacccca ggacctcgag  38940
cagttgaatg accaggctgg cttcacatat gcatgggtgt agatttgcat gtgtgtagaa  39000
gtagcatggc tggccttggc caccccacca tgacctcacc tgggtccctg ttaaactaac  39060
tccttagaca ttttgcccaa gcccacagcc tccacgaggc cctggcgtgt ccaccatctc  39120
caaacctgtc atggtccacc aggagcccaa tttcatctac aggccagctg tgaaatctga  39180
agttctggta agccccttgg gtcccctcca ggttgtctct agaggagcag accagggcta  39240
cctcccctgg gctctgctgt ctctggaggg caagtgaggt gggacaaaaa tgcagatcac  39300
agatgccatc tcttaacctt cttattggcc aagagatgag gccacatggg tgtaagtgga  39360
tgttgacatg accagtggaa tttctgttcc ccacttgact gaacagcctg gagctctgtc  39420
taaaagtaat aatgatcgct acgacctgtg aagagcctac tatataccag gctctgcatg  39480
```

```
gcctcaatta atcttcacag caggactgtg agatggttcc tgtggtcatc ctgtttaaca  39540
ctcgaggaaa gggaggttta gagaggttac cagaggggca ccaggttccc caggcagagc  39600
ctggacttaa tacttaccct catgcctttc atactccaaa gcccacgctg ttaccctcgt  39660
tgccatcttg ccaaaaccta cagagattcc aggtgccctg gcccctgccc taaggcctgt  39720
tgtggcctgg catgaaacac cctcagatgg gaaactggcc agagcaggtt cactcccttt  39780
ctccaactta cttctcacct ctcactgtga ctggaagtct gaggtgtggt cctggggaag  39840
tgagaaatgt ccgccagtct cagttactga cggctaaggg agctgggatt cgtgtgcacc  39900
tcccagaggt gccgaccact ggctggcctc ccatgcacag tgagaagaca gtcatgtcag  39960
aattttaact tccctttcaa ggaaactcta tccaaatgtc agggcaggac agctgagata  40020
tttattttgg gccttaactg tcccgtcagc tccccagaga gcaaagtttt tgctcctggg  40080
acagcctgcg gatgcatcca tgtcatgttc tctggctaat atcaaggggt ggtgtctgct  40140
tgacaacaac tgggtagcat ctttgggcat tgagcaggcc tttaacgtaa gccagactgc  40200
tcggggaggg acattggcac ggcagcccca gactggcagg cccgaagcct ggcaccaggg  40260
ggcagccaag acctattggt aacatccaat gtggaacttt tttttttttc ctctggcagc  40320
cacaggagat gttgaagagg atggtggttt atcagacagc attcagacaa gtaaactgat  40380
acccattgtg tgtctggagg tctccccacc acccccgtcc ctcccactct gtgccacttc  40440
tttctctctg ggagtacctg gtcaggtcca tggtggcccc atctgccacc aagcctcagg  40500
ccagagctgt gtcctccatt gcctgcgcag gggtggggga ggatatcata tcagatgggg  40560
acccagggct tattagaccc catgcatgag ctgagaaaca gcagtatccc tgggaactca  40620
cctcttctgc tgctgtttgt ccagagagga gcagggcaga aggaaccctc agaggcccac  40680
agaggccaag atgggccctc gctccagccc taggagagag ggaaggggct gcttaggtgt  40740
ctccctgtac cttcccctct tcttctccgg gcagatcaca gcttcaccaa ccctgcctga  40800
cactgaacca gcgtcaggga ggaggtggtg gctgaggtcc tccctgtgcc tagggcactc  40860
ctgtgcacag ggacgtggaa gtccttgctg gtcctctgag tggcatcagg caggcagcca  40920
cctacctccc tgcctcctgg ggtacctcca tggagccaac cattggattg gctgtttcat  40980
caccaatgaa agaaacccca ggacagagag agatcttgca gccagcccag gcttctccag  41040
cctcctcact gataacccac caacagacca caagctgatt tgactacagg cagggagcag  41100
aggggcagta tcaactgtgc agtgagacat aggtgttggc aaaagaggct gctcccagcc  41160
caaggatttg tcaatttaat ctttccagca accctgggtg gtaagtgcta ttatcatacc  41220
cattttatct atgagaaact gaggcagaga gatttgaaaa tgtgcccacg atggcacagc  41280
taatgtcaat ccctggattt gaatccagga ggtcggtctc tgcagcctgt gctcttaaac  41340
actgcaccat cctgccttaa agcactgtcg tcacacaaga ggccttccag gacctggcgg  41400
tttagggcac aaacagccct cacagggaga gaagcaggga agtgcagagt ctaggctcca  41460
gaggtggagt caaacccttg ctcccctgcc cactgactgg gtgaccttgg gcgtgaatat  41520
cacctctctg ggcctcagtt tcttcctctg ttgaatgagg ggttgggctg cctctttaag  41580
ggccaaccag ctgcagtggc ttatgagtct ctgatctaaa ttcacacaaa acacaagtac  41640
ctgccatctg gcccatccct gagagctggt tctcaggatc atggagcaag gaggccagag  41700
ccagcactgc ccagccttcc aggagaaaca gccggagtag gcagggccct caaagtcaaa  41760
gagcatcgac tccacatcct gcccaatgat ccttcttgcc tgtgcattca ctgcaccccc  41820
```

-continued

```
tcctctgtct gctgcccaca cactgacctg gatgtagctc ccaagctgag ccgagctcat  41880
ggcctcttgg ggttgagcct gggtgattga ggcaagtgag gagggatgcc aggcagatgc  41940
ttggggatct gtctgctgat atttggtgct catcttgtgc ccggaaccta gttggtgcat  42000
tctgaggata ggggaatctg tagcctcccc accacacaga ccatgggccc catgggtcac  42060
ttggtgtggt ctagggacct gcatgctgtg ggtggctcca ctcagtctgg cgaggcctgc  42120
cacggggctc tcctctgctc ccaccttcca tggggaccag ccgtggctct gctgcccttg  42180
tgcttagcat cctggcccct cagcctgggg atgcccctgg ctcccactca ctgtgtgtga  42240
ctcccgagga aggccacata gttcagggac tacctcactg tgtgttcagg tgccacctca  42300
ctgtcttgtt tctacaccct ggagccattg tccccacagc atccccccatc aagccaggtc  42360
ccctgagctg tgtgtcctcc cttctcccct agctaaaggg ccaacctgcg ctccgcagaa  42420
tctggggagg cctcttacct tctaggtaag cattacatga ggacactgcc aggctccagg  42480
ccaacactgc ttctcaacac cacctgcttt cttcttgttg tccgtgggct ccctccacca  42540
tcttgtggct gatttccagg aacagccttc tcttgagctg gatgggcccc tcctgtgggg  42600
tcagagcact gggtggagac accttgggct tcatccccca gggcctgggc ctgctccagt  42660
ggagacttgg aagagatgag gtggggccta aaggacttga ggctggggct gagactttca  42720
gcaaggcaga tgccgcctct ccagaccatc tagacgtcac tggtgcccct gcagcccctg  42780
acgcttgtgc cgctgaagca gggcagggtc aagatcctct aaagtcttcc tcagcctcct  42840
gcttgtccct gaacaggggt gccctggctg ctagggctgc cggcctcctg tctgcatccc  42900
gtaccctggc cgtgccttct cccgccctac ccctcacttc tgacccttgg attccgacca  42960
ttcatccccc tactcctcgg ctctgaccct caagaccctc tgctgtgttg ccctaaagcc  43020
ctccctttgc ttccaggatt tccggaaata tgaggaaggc tttgacccct actctatggt  43080
aagagatgac gcttctctcc tggacaagta accccaggaa cagggcagtg tgggggttag  43140
agggtttgat agtggtgcat tctgggcctt ggggtcctgg gatgaggtgg ggcacagagg  43200
agccccagtg atgccccagc tgctcttccc acgaagattc cttccaaagg gcactccagt  43260
gtgaactgta tggtgcacat gcacgtgtgt gtgtccactg tccccatggg gcctgggacc  43320
cccagttgaa gaccagtagg ggtggggctg ggcacggtcc ccttgcccat gtgctctgtg  43380
gggcccagtg tcccataggt gcctggattc cccttccagc cctaccccaa gcgccatcct  43440
tcaggccagc tcaaagcttc ccactgtctt tttctctcta gttcacccca gagcagatca  43500
tggggaagga tgtccggctc ctacgcatca agaaggtacc tgggcatgtg gaggccggtg  43560
ggccgccatc cctctctgtg cctgcccctc ctcccttggt ctcctgcctc tactctcaag  43620
gtcactcctg ggtggtctct caggtcccca ctgtcctccc ctctcccacg gagacgcccc  43680
tctgttgtag ggccgcatac ccaggcccca cttggcacca aggctgcgtt ttctccagat  43740
ggcactgccg gtgaccccat ggcttcttcc actcttactg tggctctgtc aagagactcc  43800
ttggtgccca ggtgtccaca ggctgctgtc tgcttggctc cctaaggcct gttttcctct  43860
aaccaggagg gatccttaga cctggccctg gaaggcggtg tggactcccc cattgggaag  43920
gtggtcgttt ctgctgtgta tgagcgggga gctgctgagc ggcatggtga gtggagacta  43980
gccacaccca ggtttgggga tgatacagtg gttagacggg gccctcccgg aaagcaaaca  44040
ggtgaccact tggagtgggc tgacggttgc tggagaatgc cctcccactc gggtccatcc  44100
atccgactgc ctgtccaatc cctgggggca tgggatggcg ccgggacctg tgagtacaca  44160
gccaagccag atgccaccgt gccctcaggg ggtccccagc cagggtggga gacggactca  44220
```

-continued

```
gaattgccag atactgaaag tcacagcatg gtctgctaag ggctgacggg gaactcagag  44280
tggagggaag ccatgggaac cctgaggggc ctctaaccca ccaagaggag atgggaggcc  44340
aggagtgctc ctcagagggg cgaaccctga gctgagcata gtcaatgtca gcctcgcgaa  44400
ggggagaaag ggctttcgag gaagaggagc agcacgtgga aacccccgaa accttgcctg  44460
tcctttcagt gatggtagga gccgaacgtt tggccagaac tagccatgtg ccagaagcta  44520
ttcatctggt ttgcagccct gtgtctgagc gtttcatgga tattaactca cttaatcctc  44580
acaacaaccc tgaaagcagg ttctgttatt attcttattt tacagctgag gaaactgagg  44640
ctcagagagg ttaaagtatt tgttcaagga cccacagcca ggagaaggtg gaggcaggac  44700
ttgaatccag gcagtttggt cattttgctt tactgtccgg cacaagtgcc acctctgtct  44760
gaggtcttct gcagccttgt cccttcccag agggccagag gcccccatac cctgtgtctc  44820
tcttctcatt ttgccttgtt ctttatcccc ttatctacaa aaacaccctc tgctgatgag  44880
tgaaaccttt gcagacccca ggcacagtct cttgcttcaa accatcaccc cgttcacctg  44940
tcggacagtg tctgaaaccc caccattggt gatttcttct tccatgtcaa ggaagctcct  45000
gagtcctttg tggccctttg tggagatgta ggtgcccttg gaggaggagc cccaggcctc  45060
ttaccttccc aggccagagt gggggaccct atgagcagat cccttccagg cagtcctagg  45120
ctggagccag gctgtaccat aagctggagg tggtagaatg gaggtggtaa gaggtaaggg  45180
gcaggaaaca gggatgggaa aggcccttgg gggctggcaa ccagacctct gtgggttact  45240
aaggtgaggt atgggcattg ggagccctgg atacaagtcc agctctgcac ccatgacctt  45300
ggtgacttca cactttaagc tttcatttca gccatagaag gggggacctgc ccagctgggc  45360
agctgcccca gcccatcagt gcccacccag gccccacctt cttcttctgt cttcatttct  45420
ctgtcacctg gtgacacttc tgtgatacct gcctgctgtg tctagcagag agaggggacc  45480
aggatggatg ggtgactctc ctgggtcctt cccacttaca aagccccaac ccaaccactg  45540
ccttattgcc cctgagactc tgtcatggat ttgtacaaaa tgaaaaggtg aaagtcaccc  45600
atccccagtt gcactgcaca gaggcaactg ctttctgtgg tttggtcctg cactgctttg  45660
aacataacta gtcactgatg aagcttccct aggagcacgt gtgttttaag ccaccatggc  45720
caccattgtc agtatcatac accacattcc tatgggcctt catgccacaa ggctcctggg  45780
tgatctattt caatgtaacc tggagagtgt tctgtggaca tcaggactgg gagaaattcc  45840
tccaaaaagg gctctgatgt caaagaggtg tggaaaacca cgcacaatct gtctacctct  45900
tggaaagctg cagtgcatgt tagcacattc aagactgaca aatcctgcag tgagtagctc  45960
tgttcagctt ataactcagc tttccccaaa attattagat cccaggcaac tctttcagga  46020
gcaccttatt acagcttcat ttattcaaca aatatctact gaggtcctat tttgtgtcag  46080
gcattatgtt aagtgctggg gatattatgg tgaaccaaaa agacaatccc tgcccacgtg  46140
gagctgacag tgtggtggga gagaccatca gtaaacaaac agattaatga ttacgaattg  46200
tggaaaatgc caaataagaa aagattggga tgctgtgaga gaataggcaa gatctacatt  46260
cgactgagcg ggggtcagag aagccccttc tgacatttcc tctcagacct agaagaagag  46320
aaagcaaggt agggaacagc gacatgaagc ctctgaggca ggagagagca tggcagctca  46380
gggacctgaa cagaccagca tgactggcaa cagggagggc cggctggcag aattgactca  46440
ggcctcatac tgtgctggaa atgcaggtct gtgtccctct gtaataacag aggctcatca  46500
tcaatgatat ccaggttctc ctgagctggg gtgagggggt gtggaaggga cagggactaa  46560
```

-continued

```
atgccctttg actagccact aaccaggtgg ctagtttccc ctcatgcttt ctgagtccac  46620
atgagctttc agaacccagg ctcaggtctc ttctgctgtc tggcaatgac ccccctttgc  46680
caagccctgg gccaggcacg tgtcacatac agcccagttg gccaatcagc ctcatctgcc  46740
tgcaggtggc attgtgaaag gggacgagat catggcaatc aacggcaaga ttgtgacaga  46800
ctacaccctg gctgaggctg aggctgccct gcagaaggcc tggaatcagg gcggggtaag  46860
aataaggccc ctccctcctt tcctccctca cctgcctgcc tcaaaccctg gcctctgcag  46920
ccaggtctca caataggatg cctcattcca gggtgggcat ctggagtcca ggcaacactt  46980
tggtgacacc ataccccatc cagcctgtgg tttaaatctg acaagatggg attcagaaaa  47040
atagatgtca attcctgacc ttggatccaa aaagccagtg gcttaaacag actcttgaag  47100
ccagggcatg gcaggtcacc caagaaaaag acttaaggtc ttttctaagt gcacactgaa  47160
caagaatcaa gagaattctg ggggctacca gaaagcatta acaaaagcag agaacccagg  47220
atgaaggagg ggctggtggg aatctgctct gcactcatta gacacccacc tggatcacgg  47280
ccactgcata agattgccca ggctgtgcac tacataatct gagggggtgc ccttttacag  47340
actgtagtgt gaatggtgcc tgctcatggt gtgcaatgca caacctgtgc aactgtatgc  47400
aggcagccga gcctgaggta ttaagttcag tgccgaggaa gctgaccaga tgggcctggg  47460
acccacatga agggatgtgg agaagagaag actcacgggt aacatgatga ctatctttga  47520
ttatctgaag gtctgcatta gggcagaggg agcagaagtg ttctctctga ttcttgaggg  47580
aagacctgga ttggatggag ggaagtcctg gggaaagaga gagagatttc agctcaatat  47640
taggaaccag ctcatggtag aggggcccag tgatatttcc aatacttttc aggggataca  47700
cctaagccaa ggagggagaa tgaggggcaa gtcaaggatg gcagtaaaag ggattcaggt  47760
gttaggatca aaaagctggg ccagaagtcc cccacttgat tgtgcatcag aaagtgcgtc  47820
ggaattaccc agagaggttg ttaaaagtac tatttcccag gactcaccct tgacttctgg  47880
gggccaagtc tacgagccta cacttttaag aagttccccc aagtgattct gaggttgctg  47940
cctgtccccg gtccatagat tgacatttgg gagctgagtg tcattcaagg gccttgcagc  48000
cctgtcctct atggtcccga agcctcagag actagaaacg tcctcagacc atggaagtca  48060
cagtgggccc caggtgggcc cgtgggaaga aggtgcagcc tggctgatcc taggccatgg  48120
ggcccagaaa tggggatgga gtgccggggc agatgcacca tccaactgag tgtgccccag  48180
agtcacacgg cttctcccca caggactgga tcgaccttgt ggttgccgtc tgccccccaa  48240
aggagtatga cgatgagctg taagtgtgtg caagcaccta gcctgagacc tcttcttcct  48300
tctccagaat ctcagccacc tttctccagc ccatccccag ccttctccca gcctgaagga  48360
atggcccaag cacgcagctt ctcatagcca gagctcctag aaaactcctg gactagagcc  48420
aagtcattgt ccttaagcag tgtctgagct gcctcccggg cagtcttgtc caaattcttc  48480
tctactatgg ggaattgagg catgaggtct tagaccgggt aagcagagac gttgggaaaa  48540
agactcagga ttgttaattc cccactcaga actttatccc ctgccccatt attagatggt  48600
tagaaggtgt ctgtgtccat ccttcactct ctggaaggtc ttcctgatgt ctaactgcat  48660
tcactcatac tgtgcctcta ggcagccggg accacaggct tttgtcccca cgctgtggga  48720
tctccaggga gctttggcct agactgtctc tctctgtgat tccctgtgtg tctgtctctt  48780
gtgtcctgtg ggtctctctg tcttctctcc tcctccctct ctgtctttct ttcacccttt  48840
ccttccttcc tgtcaacatc ttatctgccc ccctccttcc ccttcatccc ggtcccettt  48900
ctctctcact gtctcctatt ctttcttcct gtttctcttc atccctgtct ctgagtccct  48960
```

```
gttcctctgt ccttgtcatt ctgcatccat tcttacctct ttgtctgcct ttctctgttt  49020
ctctgcctct gtgtggtgtc tcacctccat cctcacctca tcccatcacc tccccagccc  49080
tcacccaccc accactcacc cactcactga ccatgccctg cctccctgtc gtggctgggc  49140
ctgcttgctc cccgtgccca gcagaatctg agctctacac atgtcttgga gaaaccaggg  49200
tctcgcagct cctaattctg gaacccaggg gctaggcaga acccgaggca ggagcccagt  49260
gaaaggagaa gccccatgga gctctgcctg ggagtaacca agcctgtttt gtgtttcttg  49320
ctctgctctg tatatataga gcttctcttc cctcctccgt agctgaaagc ccccaaccgg  49380
tccgaaagct ccttgaagac cgtgctgccg tgcacagaca cgggttcctc ctgcagctgg  49440
agcccacggt gaataggcag gcgggccaca gggccctgtg tgtccctgct gcttgcagtg  49500
gccatctgct gcccacgctg tcagcaggtt ctttggactg gcgtctggag ggtacacaag  49560
gcgccatccc tgaagtgctg cctggggcct gctgttggcc acagtggaat tcctcagact  49620
caaagccctc ccctcaggga agtggtgcaa agcccagtct gtagtacttg cttgggaccc  49680
aggtgtcctg actcatcacg gccctgggac ctgctttggg tcccaagcag cacccaaatg  49740
agcaggatga agccctgggc aacattctct gagggacaca gacaatgcct cgaaccaggc  49800
atgtggggct gaaggagccc acaggaagcc tggctggaat tgcccccaag agatgtcctc  49860
aacagaatgt gaaaattccc cttcctgtga atgccaacct cctgggagct cttgctccac  49920
catggccccc acacttggcc agaaccaggg ctattaagag gttttgaagg ctggtccaaa  49980
gaaccagggt tggtggatta gagttgctca tgtcctgttg tgccctgtca tggcctgagc  50040
cgtgcttaga ccaaacggtc ttctctgcct tctcccttcc ttggctctgg gctctatctg  50100
tgggatatac cgtggaaccc agctgtagga tgtgtttctc accctgtgat agggatgtgc  50160
ccgtggacag agctggcagg tggctgtgaa actggtgttt ggtgtggcct gaagccacag  50220
atggcagcat ctggggcaga cccaagcctg gacttgactt ttctgttaca actttcccaa  50280
aacattaggg cctcatgctc ccaagacact tggccgggta gaccatggct tctggggtgg  50340
cctgcatggc cctatgtttt ctgttacttg ccttttgcaa aggactcttg cccctgttcc  50400
tcccagtctc ctccttcccc catcccaggt gtccctcccg ctttctccct ggcctcctgt  50460
gtgctgtggc tgtggctggt gtgtagccac ttggggcctg cacccagagg ggtctccaaa  50520
gggtggcagg gccttgtgct gccagagtgg gtactccccc ttgtggggcc ttgctctggc  50580
tgggctgagt gtgcacccac aaagcctgta tccacctggg ctgtttccac ttccctgcag  50640
gaccttcttc tgaagtccaa aaggggaaac caaattcacc gttaggaaac agtgagctcc  50700
ggccccacct cgtgaacaca aagcctcgga tcagccttga gagaggccac actacacaca  50760
ccagatggca tccttgggac ctgaatctat cacccaggaa tctcaaactc cctttggccc  50820
tgaaccaggg ccagataagg aacagctcgg gccactcttc tgaaggccaa cgtggaggaa  50880
agggagcagc cagccatttg ggagaagatc tcaaggatcc agactctcat tcctttcctc  50940
tggcccagtg aatttggtct ctcccagctc tgggggactc cttccttgaa ccctaataag  51000
accccactgg agtctctctc tctccatccc tctcctctgc cctctgctct aattgctgcc  51060
aggattgtca ctccaaacct tactctgagc tcattaataa aatagattta ttttccagct  51120
tataggagtg agtgtggatt tgggcagcag attcaaggct gcaaatcaaa aaaccataag  51180
gtttgtggcc cctattcaag ggtgatagac agatcccagt gctgtgatct gggtctgaca  51240
tgaagggtgt gatcaaatgg ccagggctgg cttggagcag aggttgagaa agcaggagat  51300
```

```
gggctgggct gggcttcaat gtcttctcag cagagatggt aggagatgaa gtctgtgtgg  51360

cagggatttt gctcaattcc agaaagcaga gctgaaggca ggagccccga agggtcacct  51420

catgatatgg ggtgcccagc ttctttcaag aacgacacag ccaccaatgc ttctcctgag  51480

gtcaccacga cagcatgtga gggaggaaga tggcagggtc cactccctcc gtggaagcac  51540

atcccacaga agctcatggg aaatgcaagg gcttgaggca ggaaggcata actccggggg  51600

cccagcaggg ggaatgtcac agttcttctg gtgacaggga ccagggctgc tagctctgag  51660

gaagagggtg gggctgtatc agcacgactc gcctgacccc gtctctgttt ccccattcca  51720

aa                                                                 51722


<210> SEQ ID NO 2
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2

acggccacgt ccatggtc                                                   18


<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3

cgagcacggc cacgtcca                                                   18


<210> SEQ ID NO 4
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 4

tcccacgagc acggccac                                                   18


<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 5

aggtctccca cgagcacg                                                   18


<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6

gcttcaggtc tcccacga                                                   18


<210> SEQ ID NO 7
<211> LENGTH: 18
```

<212> TYPE: DNA
<213> ORGANISM: Artificial sequence
<220> FEATURE:
<223> OTHER INFORMATION: Synthetic oligonucleotide

<400> SEQUENCE: 7
gaccagcttc aggtctcc 18

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
ttgatgacca gcttcagg 18

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
gttcattgat gaccagct 18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
gctgggttca ttgatgac 18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
agacggctgg gttcattg 18

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 12
gaggcagacg gctgggtt 18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13

-continued aaacagaggc agacggct 18

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
gcatcaaaca gaggcaga 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
gaatggcatc aaacagag 18

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
cggccgaatg gcatcaaa 18

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
atcagcggcc gaatggca 18

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
gtgggatcag cggccgaa 18

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
cttcagtggg atcagcgg 18

<210> SEQ ID NO 20
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 20

tgcttcagtg ggatcagc                                                    18


<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21

tggtgcttca gtgggatc                                                    18


<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 22

acctggtgct tcagtggg                                                    18


<210> SEQ ID NO 23
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 23

atattctacc tggtgcttca gtggg                                            25


<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24

ctacctggtg cttcagtg                                                    18


<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 25

ttctacctgg tgcttcag                                                    18


<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26

atattctacc tggtgctt                                                    18
```

<210> SEQ ID NO 27
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 27
agctgatcat attctacctg gtgct 25

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
atcatattct acctggtg 18

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
tgatcatatt ctacctgg 18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
agctgatcat attctacc 18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
tcagctgatc atattcta 18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
gggtcagctg atcatatt 18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
gggggtcagc tgatcata 18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
cgccgggggg tcagctga 18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
tggagcgccg gggggtca 18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
gcacctggag cgccgggg 18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
cctctgcacc tggagcgc 18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
ggcttcctct gcacctgg 18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
ctggtggctt cctctgca 18

<210> SEQ ID NO 40

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
ccagcctggt ggcttcct 18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
tgcctccagc ctggtggc 18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
ccccctgcct ccagcctg 18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
ctccaccccc tgcctcca 18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
gatctctcca ccccctgc 18

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
agggtgatct ctccaccc 18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
cgcccagggt gatctctc 18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
tgccccgccc agggtgat 18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
agcactgccc cgcccagg 18

<210> SEQ ID NO 49
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 49
atattctacc tggtg 15

<210> SEQ ID NO 50
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 50
catattctac ctggt 15

<210> SEQ ID NO 51
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 51
tcatattcta cctgg 15

<210> SEQ ID NO 52
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 52
atcatattct acctg 15

<210> SEQ ID NO 53
<211> LENGTH: 15
<212> TYPE: DNA

-continued

```
<213> ORGANISM: Artificial sequence
<220> FEATURE:
<223> OTHER INFORMATION: Synthetic oligonucleotide

<400> SEQUENCE: 53

gatcatattc tacct                                                     15


<210> SEQ ID NO 54
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 54

tgatcatatt ctacc                                                     15


<210> SEQ ID NO 55
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 55

ctgatcatat tctac                                                     15


<210> SEQ ID NO 56
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 56

gctgatcata ttcta                                                     15


<210> SEQ ID NO 57
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 57

agctgatcat attct                                                     15


<210> SEQ ID NO 58
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 58

atcatattct ac                                                        12


<210> SEQ ID NO 59
<211> LENGTH: 57
<212> TYPE: DNA
<213> ORGANISM: Homo sapiens

<400> SEQUENCE: 59

cccactgaag caccaggtag aatatgatca gctgaccccc cggcgctcca ggtgcag       57
```

ANTISENSE COMPOUNDS TARGETING GENES ASSOCIATED WITH USHER SYNDROME

CROSS REFERENCED TO RELATED APPLICATIONS

This application is a U.S. National Phase filing under 35 U.S.C. §371 claiming priority to International Serial No. PCT/US2012/036189 filed May 2, 2012, which claims priority to U.S. Provisional Application 61/587,074, filed Jan. 16, 2012, and U.S. Provisional Application 61/481,654, filed May 2, 2011, each of which is incorporated herein by reference in its entirety.

SEQUENCE LISTING

The present application is being filed along with a Sequence Listing in electronic format. The Sequence Listing is provided as a file entitled CORE0095USASEQ.TXT, created Oct. 3, 2013, which is 76 Kb in size. The information in the electronic format of the sequence listing is incorporated herein by reference in its entirety.

BACKGROUND OF THE INVENTION

Usher Syndrome is a leading genetic cause of combined blindness and deafness. In certain instances, Usher Syndrome results from a mutation in an Usher gene. See, e.g., Millan J M et al., An Update on the Genetics of Usher Syndrome, Journal of Ophthalmology, V 2001, Article ID 417217 (2001).

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Certain antisense compounds have been described previously. See for example U.S. Pat. No. 7,399,845 and published International Patent Application No. WO 2008/049085, which are hereby incorporated by reference herein in their entirety.

SUMMARY OF THE INVENTION

In certain embodiments, the present invention provides compounds comprising oligonucleotides. In certain embodiments, such oligonucleotides are complementary to an Usher transcript. In certain such embodiments, the oligonucleotide is complementary to a target region of the Usher transcript comprising exon 2, intron 2, exon 3, and intron 3. In certain embodiments, the Usher transcript comprises a mutation that results in a cryptic splice site. In certain embodiments, oligonucleotides inhibit cryptic splicing. In certain such embodiments, normal splicing is increased. In certain embodiments, truncated, but non-cryptic splicing is increased.

The present disclosure provides the following non-limiting numbered embodiments:

Embodiment 1

A compound comprising a modified oligonucleotide consisting of 8 to 30 linked nucleosides and having a nucleobase sequence comprising a complementary region comprising at least 8 contiguous nucleobases complementary to a target region of equal length of an Usher transcript.

Embodiment 2

The compound of embodiment 1, wherein the complementary region of the modified oligonucleotide is 100% complementary to the target region.

Embodiment 3

The compound of embodiment 1 or 2, the complementary region of the modified oligonucleotide comprises at least 10 contiguous nucleobases.

Embodiment 4

The compound of embodiment 1 or 2, the complementary region of the modified oligonucleotide comprises at least 15 contiguous nucleobases.

Embodiment 5

The compound of embodiment 1 or 2, the complementary region of the modified oligonucleotide comprises at least 20 contiguous nucleobases.

Embodiment 6

The compound of any of embodiments 1-5, wherein the nucleobase sequence of the oligonucleotide is at least 80% complementary to an equal-length region of the Usher transcript, as measured over the entire length of the oligonucleotide.

Embodiment 7

The compound of any of embodiments 1-5, wherein the nucleobase sequence of the oligonucleotide is at least 90% complementary to an equal-length region of the Usher transcript, as measured over the entire length of the oligonucleotide.

Embodiment 8

The compound of any of embodiments 1-5, wherein the nucleobase sequence of the oligonucleotide is 100% complementary to an equal-length region of the Usher transcript, as measured over the entire length of the oligonucleotide.

Embodiment 9

The compound of any of embodiments 1-8, wherein the target region is within exon 3 of the Usher transcript.

Embodiment 10

The compound of any of embodiments 1-9, wherein the target region is within nucleobase 13475 and nucleobase 13660 of SEQ ID NO.: 1.

Embodiment 11

The compound of any of embodiments 1-9, wherein the target region is within nucleobase 13480 and nucleobase 13620 of SEQ ID NO.: 1.

Embodiment 12

The compound of any of embodiments 1-9, wherein the target region is within nucleobase 13550 and nucleobase 13620 of SEQ ID NO.: 1.

Embodiment 13

The compound of any of embodiments 1-9, wherein the target region is within nucleobase 13577 and nucleobase 13600 of SEQ ID NO.: 1.

Embodiment 14

The compound of any of embodiments 1-13, wherein the antisense oligonucleotide comprises SEQ ID NO: 30.

Embodiment 15

The compound of any of embodiments 1-13, wherein the antisense oligonucleotide comprises SEQ ID NO: 29.

Embodiment 16

The compound of any of embodiments 1-13, wherein the antisense oligonucleotide comprises SEQ ID NO: 27.

Embodiment 17

The compound of any of embodiments 1-13, wherein the antisense oligonucleotide comprises SEQ ID NO: 50.

Embodiment 18

The compound of any of embodiments 1-13, wherein the antisense oligonucleotide comprises SEQ ID NO: 56.

Embodiment 19

The compound of any of embodiments 1-18, wherein the modified oligonucleotide comprises at least one modified nucleoside.

Embodiment 20

The compound of embodiment 19, wherein at least one modified nucleoside comprises a modified sugar moiety.

Embodiment 21

The compound of embodiment 20, wherein at least one modified sugar moiety is a 2'-substituted sugar moiety.

Embodiment 22

The compound of embodiment 21, wherein the 2'-substituten of at least one 2'-substituted sugar moiety is selected from among: 2'-OMe, 2'-F, and 2'-MOE.

Embodiment 23

The compound of embodiment 22, wherein the 2'-substituent of at least one 2'-substituted sugar moiety is a 2'-MOE.

Embodiment 24

The compound of any of embodiments 20-23, wherein at least one modified sugar moiety is a bicyclic sugar moiety.

Embodiment 25

The compound of embodiment 24, wherein at least one bicyclic sugar moiety is LNA or cEt.

Embodiment 26

The compound of any of embodiments 20-25, wherein at least one sugar moiety is a sugar surrogate.

Embodiment 27

The compound of embodiment 26, wherein at least one sugar surrogate is a morpholino.

Embodiment 28

The compound of embodiment 26, wherein at least one sugar surrogate is a modified morpholino.

Embodiment 29

The compound of any of embodiment 1-28, wherein the modified oligonucleotide comprises at least 5 modified nucleosides, each independently comprising a modified sugar moiety.

Embodiment 30

The compound of embodiment 29, wherein the modified oligonucleotide comprises at least 10 modified nucleosides, each independently comprising a modified sugar moiety.

Embodiment 31

The compound of embodiment 29, wherein the modified oligonucleotide comprises at least 15 modified nucleosides, each independently comprising a modified sugar moiety.

Embodiment 32

The compound of embodiment 29, wherein each nucleoside of the modified oligonucleotide is a modified nucleoside, each independently comprising a modified sugar moiety Embodiment 33

The compound of any of embodiments 1-32, wherein the modified oligonucleotide comprises at least two modified nucleosides comprising modified sugar moieties that are the same as one another.

Embodiment 34

The compound of any of embodiments 1-33, wherein the modified oligonucleotide comprises at least two modified nucleosides comprising modified sugar moieties that are different from one another.

Embodiment 35

The compound of any of embodiments 1-34, wherein the modified oligonucleotide comprises a modified region of at least 5 contiguous modified nucleosides.

Embodiment 36

The compound of embodiment 35, wherein the modified oligonucleotide comprises a modified region of at least 10 contiguous modified nucleosides.

Embodiment 37

The compound of embodiment 35, wherein the modified oligonucleotide comprises a modified region of at least 15 contiguous modified nucleosides.

Embodiment 38

The compound of embodiment 35, wherein the modified oligonucleotide comprises a modified region of at least 20 contiguous modified nucleosides.

Embodiment 39

The compound of any of embodiments 34-38, wherein each modified nucleoside of the modified region has a modified sugar moiety independently selected from among: 2'-F, 2'-OMe, 2'-MOE, cEt, LNA, morpholino, and modified morpholino.

Embodiment 40

The compound of any of embodiments 35-39, wherein the modified nucleosides of the modified region each comprise the same modification as one another.

Embodiment 41

The compound of embodiment 40, wherein the modified nucleosides of the modified region each comprise the same 2'-substituted sugar moiety.

Embodiment 42

The compound of embodiment 40, wherein the 2'-substituted sugar moiety of the modified nucleosides of the region of modified nucleosides is selected from 2'-F, 2'-OMe, and 2'-MOE.

Embodiment 43

The compound of embodiment 41, wherein the 2'-substituted sugar moiety of the modified nucleosides of the region of modified nucleosides is 2'-MOE.

Embodiment 44

The compound of embodiment 40, wherein the modified nucleosides of the region of modified nucleosides each comprise the same bicyclic sugar moiety.

Embodiment 45

The compound of embodiment 44, wherein the bicyclic sugar moiety of the modified nucleosides of the region of modified nucleosides is selected from LNA and cEt.

Embodiment 46

The compound of embodiment 40, wherein the modified nucleosides of the region of modified nucleosides each comprises a sugar surrogate.

Embodiment 47

The compound of embodiment 46, wherein the sugar surrogate of the modified nucleosides of the region of modified nucleosides is a morpholino.

Embodiment 48

The compound of embodiment 46, wherein the sugar surrogate of the modified nucleosides of the region of modified nucleosides is a modified morpholino.

Embodiment 49

The compound of any of embodiments 1-48, wherein the modified nucleotide comprises no more than 4 contiguous naturally occurring nucleosides.

Embodiment 50

The compound of any of embodiments 1-48, wherein each nucleoside of the modified oligonucleotide is a modified nucleoside.

Embodiment 51

The compound of embodiment 50 wherein each modified nucleoside comprises a modified sugar moiety.

Embodiment 52

The compound of embodiment 51, wherein the modified nucleosides of the modified oligonucleotide comprise the same modification as one another.

Embodiment 53

The compound of embodiment 52, wherein the modified nucleosides of the modified oligonucleotide each comprise the same 2'-substituted sugar moiety.

Embodiment 54

The compound of embodiment 53, wherein the 2'-substituted sugar moiety of the modified oligonucleotide is selected from 2'-F, 2'-OMe, and 2'-MOE.

Embodiment 55

The compound of embodiment 54, wherein the 2'-substituted sugar moiety of the modified oligonucleotide is 2'-MOE.

Embodiment 56

The compound of embodiment 52, wherein the modified nucleosides of the modified oligonucleotide each comprise the same bicyclic sugar moiety.

Embodiment 57

The compound of embodiment 56, wherein the bicyclic sugar moiety of the modified oligonucleotide is selected from LNA and cEt.

Embodiment 58

The compound of embodiment 52, wherein the modified nucleosides of the modified oligonucleotide each comprises a sugar surrogate.

Embodiment 59

The compound of embodiment 58, wherein the sugar surrogate of the modified oligonucleotide is a morpholino.

Embodiment 60

The compound of embodiment 58, wherein the sugar surrogate of the modified oligonucleotide is a modified morpholino.

Embodiment 61

The compound of any of embodiments 1-60, wherein the modified oligonucleotide comprises at least one modified internucleoside linkage.

Embodiment 62

The compound of embodiment 61, wherein each internucleoside linkage is a modified internucleoside linkage.

Embodiment 63

The compound of embodiment 61 or 62, comprising at least one phosphorothioate internucleoside linkage.

Embodiment 64

The compound of embodiment 62, wherein each internucleoside linkage is a modified internucleoside linkage and wherein each internucleoside linkage comprises the same modification.

Embodiment 65

The compound of embodiment 64, wherein each internucleoside linkage is a phosphorothioate internucleoside linkage.

Embodiment 66

The compound of any of embodiments 1-65 comprising at least one conjugate.

Embodiment 67

The compound of any of embodiments 1-66 consisting of the modified oligonucleotide.

Embodiment 68

The compound of any of embodiments 1-67, wherein the compound modulates splicing of the Usher transcript.

Embodiment 69

The compound of any of embodiments 1-68, having a nucleobase sequence comprising any of the sequences as set forth in SEQ ID NOs. 2-57.

Embodiment 70

The compound of any of embodiments 1-68, having a nucleobase sequence comprising any of the sequences as set forth in SEQ ID NOs. 2-31 or 49-57.

Embodiment 71

The compound of any of embodiments 1-68, having a nucleobase sequence comprising any of the sequences as set forth in SEQ ID NOs. 2-31.

Embodiment 72

The compound of any of embodiments 1-68, having a nucleobase sequence comprising any of the sequences as set forth in SEQ ID NOs. 49-57.

Embodiment 73

A method of modulating splicing an Usher transcript in a cell comprising contacting the cell with a compound according to any of embodiments 1-72.

Embodiment 74

The method of embodiment 73, wherein the cell is in vitro.

Embodiment 75

The method of embodiment 73, wherein the cell is in an animal.

Embodiment 76

A method of modulating the expression of harmonin in a cell, comprising contacting the cell with a compound according to any of embodiments 1-72.

Embodiment 77

The method of embodiment 76, wherein harmonin expression is increased.

Embodiment 78

The method of embodiment 76, wherein the cell is in vitro.

Embodiment 79

The method of embodiment 76, wherein the cell is in an animal.

Embodiment 80

A method of increasing the total number of correctly shaped stereocilia bundles in the ear, comprising contacting a cell with a compound according to any of embodiments 1-72.

Embodiment 81

The method of embodiment 80, wherein the cell is in an animal.

Embodiment 82

A pharmaceutical composition comprising a compound according to any of embodiments 1-72 and a pharmaceutically acceptable carrier or diluent.

Embodiment 83

The pharmaceutical composition of embodiment 82, wherein the pharmaceutically acceptable carrier or diluent is sterile saline.

Embodiment 84

A method comprising administering the pharmaceutical composition of embodiments 82 or 83 to an animal.

Embodiment 85

The method of embodiment 84, wherein the administration is by injection.

Embodiment 86

The method of embodiment 84 or 85, wherein the administration is systemic.

Embodiment 87

The method of embodiment 84 or 85 wherein the administration is local.

Embodiment 88

The method of embodiment 87, wherein the administration is to the eye of the animal.

Embodiment 89

The method of embodiment 87, wherein the administration is to the ear of an animal.

Embodiment 90

The method of any of embodiments 84-89, wherein the animal has one or more symptom of Usher Syndrome.

Embodiment 91

The method of embodiment 90, wherein the administration results in amelioration of at least one symptom of Usher Syndrome.

Embodiment 92

The method of embodiment 91, wherein the symptom is deafness.

Embodiment 93

The method of embodiment 91, wherein the symptom is blindness.

Embodiment 94

The method of any of embodiments 84-93, wherein the animal is a mouse.

Embodiment 95

The method of any of embodiments 84-93, wherein the animal is a human.

Embodiment 96

The method of any of embodiments 84-93, wherein the first administration occurs within 1-15 days after birth.

Embodiment 97

The method of any of embodiments 84-93, wherein the first administration occurs within 1-10 days after birth.

Embodiment 98

The method of any of embodiments 84-93, wherein the first administration occurs within 1-5 days after birth.

Embodiment 99

The method of any of embodiments 84-93, wherein the first administration occurs within 3-5 days after birth.

Embodiment 100

The method of any of embodiments 84-93, wherein the first administration is in utero.

Embodiment 101

Use of the compound of any of embodiments 1 to 72 or the composition of embodiments 82-83 for the preparation of a medicament for use in the treatment of Usher syndrome.

Embodiment 102

Use of the compound of any of embodiments 1 to 72 or the composition of embodiments 82-83 for the preparation of a medicament for use in the amelioration of one or more symptoms of Usher syndrome.

In certain embodiments, including, but not limited to any of the above numbered embodiments, the Usher transcript is in a human having Usher Syndrome. In certain such embodiments, the Usher gene of the human comprises a 216 mutation. In certain such embodiments, the Usher gene of the human comprises a 216AA mutation.

BRIEF DESCRIPTION OF THE FIGURES

FIG. 2*b* shows the number of rotations of Ush1c.2166AA mice treated with a mismatched control, Ush1c.2166AA mice treated with Isis No. 527134, and heterozygous mice in an open-field pathway trace.

FIGS. 3*a-d* show auditory-evoked brainstem response (ABR) analysis at 8 kHz, 16 kHz, and 32 kHz and BBN, for Ush1c.2166AA mice treated with a mismatched control, Ush1c.2166AA mice treated with Isis No. 527134, wild-typ mice, and heterozygous mice.

FIG. 8 shows audiograms of broad-band noise and pure-tone stimuli at 8 kHz, 16 kHz, 32 kHz at two months of age for Ush1c.216AA mutant mice treated with Isis No. 527134, Ush1c.216AA mutant mice treated with a mismatched control, and heterozygous mice.

FIG. 12*a* shows RT-PCR analysis of RNA isolated from the retina of Ush1c.216AA mice treated with Isis No. 527134.

FIG. 12*b* shows Western Blot analysis of harmonin protein isolated from the retina of Ush1c.216AA mice treated with Isis No. 527134, Ush1c.216AA mutant mice treated with a mismatched control, and heterozygous mice.

FIG. 12*c* shows RT-PCR analysis of RNA isolated from the retina of Ush1c.216AA mice treated with Isis No. 527134 at P12, P30, and P120.

FIG. 12*d* shows quantification of the RT-PCR analysis of RNA isolated from the retina of Ush1c.216AA mice treated with Isis No. 527134 at P12, P30, and P120.

DETAILED DESCRIPTION OF THE INVENTION

Figure 1A:
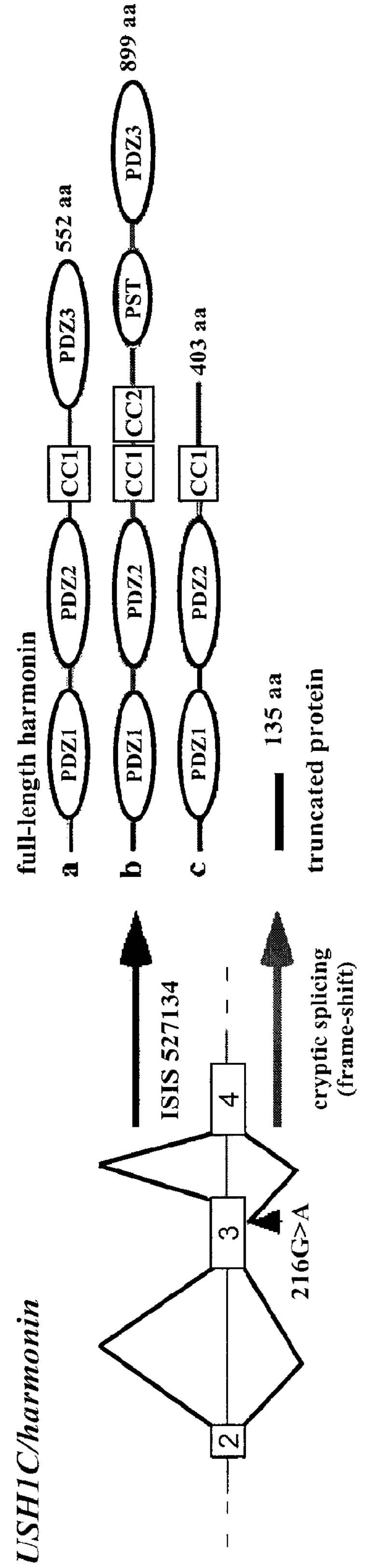
FIG. 1*a* shows a schematic of Ush1c splicing and protein products encoded by expressed mRNAs. A portion of the Ush1c gene is shown. Exons are represented as boxes and lines are introns. Diagonal lines indicate splicing pathways. The location of the 216A mutation and the cryptic splice site are shown. Hatched lines indicate the cryptic splicing pathway activated by the 216A mutation. The three PDZ1 domains and the coiled-coil domain (CC1) of the harmonin protein are shown. Exon skipping removes the first 12 amino acids of the first PDZ domain. The truncated protein terminates within the PDZ1 domain.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means $-OCH_2CH_2OCH_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$—O-2'bridge.

As used herein, "locked nucleic acid nucleoside" or "LNA" means a nucleoside comprising a bicyclic sugar moiety comprising a 4'-$CH_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "Usher Transcript" means a transcript transcribed from an Usher Gene. As used herein, "Usher gene" means a gene as described in Verpy, E, Leibovici, M, Zwaenepoel, I, Liu, X Z, Gal, A, Salem, N, Mansour, A, Blanchard, S, Kobayashi, I, Keats, B J, Slim, R, Petit, C. 2000, *A defect in harmonin, a PDZ domain-containing protein expressed in the inner ear sensory hair cells, underlies Usher syndrome type 1C*. Nat. Genet. 26:51-55 and having a sequence Accession Number ENSG00000006611, provided herein as SEQ ID NO. 1, or a variant thereof. In certain embodiments, an Usher gene is at least 90% identical to Accession Number ENSG00000006611, set forth as SEQ ID NO 1. In certain embodiments, an Usher gene is at least 95% identical to Accession Number ENSG00000006611, set forth as SEQ ID NO 1. In certain embodiments, an Usher gene is 100% identical to Accession Number ENSG00000006611, set forth as SEQ ID NO 1.

As used herein, "Ush1c" means an Usher transcript transcribed from the Usher gene.

As used herein, "harmonin" means Ush1c or a protein encoded therefrom.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)—($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substitued sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, $O(CH_2)_2SCH_3$, $O(CH_2)_2$—O—N(Rm)(Rn), and O—$CH_2$—C(═O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, 5-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)_2SCH_3$, O—$(CH_2)_2$—O—N($R_m$)($R_a$), $O(CH_2)_2O(CH_2)_2N(CH_3)_2$, and N-substituted acetamide (O—$CH_2$—C(═O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, O—$(CH_2)_2$—O—$N(CH_3)_2$, —$O(CH_2)_2O(CH_2)_2N(CH_3)_2$, and O—$CH_2$—C(═O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —$[C(R_a)(R_b)]_n$—, —$[C(R_a)(R_b)]_n$—O—, —C($R_aR_b$)—N(R)—O— or, —C($R_aR_b$)—O—N(R)—; 4'-$CH_2$-2', 4'-$(CH_2)_2$-2', 4'-$(CH_2)_3$-2', 4'-($CH_2$)—O-2' (LNA); 4'-($CH_2$)—S-2; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*, 2009, 74, 118-134); and 4'-$CH_2$—C(═$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —$[C(R_a)(R_b)]_n$—, —C($R_a$)═C($R_b$)—, —C($R_a$)═N—, —C(═N$R_a$)—, —C(═O)—, —C(═S)—, —O—, —Si$(R_a)_2$—, —S$(═O)_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl $(S(═O)_2$-$J_1)$, or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

(A)

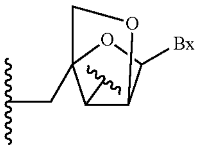

(B)

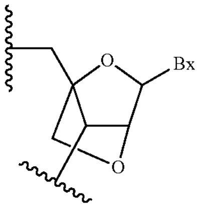

(C)

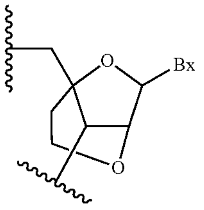

(D)

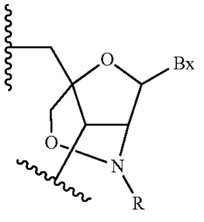

(E)

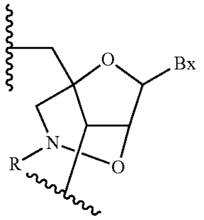

-continued (F)

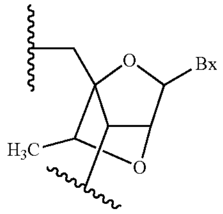

(G)

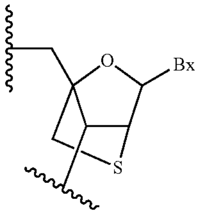

(H)

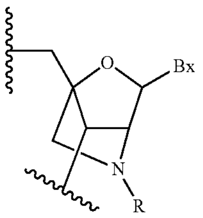

(I)

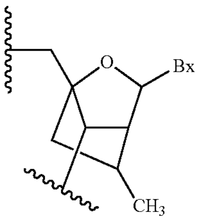

(J)

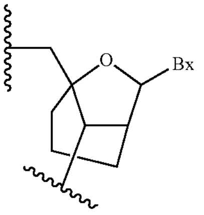

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

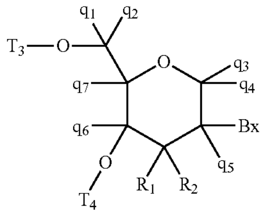

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

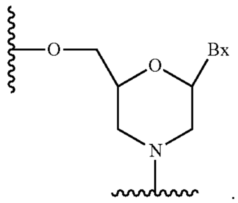

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino ($-CH_2-N(CH_3)-O-CH_2-$), thiodiester ($-O-C(O)-S-$), thionocarbamate ($-O-C(O)(NH)-S-$); siloxane ($-O-Si(H)_2-O-$); and N,N'-dimethylhydrazine ($-CH_2-N(CH_3)-N(CH_3)-$). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2-N(CH_3)-O$-5'), amide-3 (3'-$CH_2-C(=O)-N(H)$-5'), amide-4 (3'-$CH_2-N(H)-C(=O)$-5'), formacetal (3'-O-$CH_2$-O-5'), and thioformacetal (3'-S-$CH_2$-O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is an Usher transcript. In certain embodiments, the target RNA is an Usher pre-mRNA.

In certain embodiments, an antisense compound is complementary to a region of an Usher pre-mRNA. In certain embodiments, an antisense compound is complementary within a region of an Usher pre-mRNA comprising exon 2, intron 2, exon 3, and intron 3. In certain embodiments, an antisense compound is complementary to a region of an Usher pre-mRNA consisting of exon 2, intron 2, exon 3, and intron 3. In certain embodiments, an antisense compound is complementary to a region of an Usher pre-mRNA consisting of intron 2, exon 3, and intron 3. In certain embodiments, an antisense compound is complementary to a region of an Usher pre-mRNA consisting of exon 3 and intron 3. In certain embodiments, an antisense compound is complementary to a region of an Usher pre-mRNA consisting of exon 3.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equel length of an Usher transcript. In certain embodiments, the target region is within nucleobase 13475 and nucleobase 13660 of SEQ ID NO.: 1. In certain embodiments, the target region is within nucleobase 13480 and nucleobase 13500 of SEQ ID NO.: 1. In certain embodiments, the target region is within nucleobase 13515 and nucleobase 13535 of SEQ ID NO.: 1. In certain embodiments, the target region is within nucleobase 13550 and nucleobase 13575 of SEQ ID NO.: 1. In certain embodiments, the target region is within nucleobase 13577 and nucleobase 13597 of SEQ ID NO.: 1.

In certain embodiments, an antisense oligonucleotide modulates splicing of a pre-mRNA. In certain embodiments, an antisense oligonucleotide modulates splicing an Usher pre-mRNA. In certain such embodiments, the Usher pre-mRNA is transcribed from a mutant variant of Usher. In certain embodiments, the mutant variant comprises a cryptic splice site. In certain embodiments, an antisense oligonucleotide reduces cryptic splicing of an Usher pre-mRNA. In certain embodiments, an antisense oligonucleotide increases that amount of normally spliced Usher mRNA. In certain embodiments, an antisense oligonucleotide increases that amount of exon 3 skipped Usher mRNA.

In certain embodiments, an antisense oligonucleotide alters the amount of harmonin mRNA. In certain embodiments, an antisense oligonucleotide alters the amount of harmonin RNA. In certain embodiments, an antisense oligonucleotide alters the amount of harmonin protein. In certain embodiments, an antisense oligonucleotide alters the amount of harmonin mRNA in the ear. In certain embodiments, an antisense oligonucleotide alters the amount of harmonin RNA in the ear. In certain embodiments, an antisense oligonucleotide alters the amount of harmonin protein in the ear. In certain embodiments, an antisense oligonucleotide alters the amount of harmonin mRNA in the cochlea. In certain embodiments, an antisense oligonucleotide alters the amount of harmonin RNA in the cochlea. In certain embodiments, an antisense oligonucleotide alters the amount of harmonin protein in the cochlea. In certain embodiments, an antisense oligonucleotide alters the amount of harmonin mRNA in the retina. In certain embodiments, an antisense oligonucleotide alters the amount of harmonin RNA in the retina. In certain embodiments, an antisense oligonucleotide alters the amount of harmonin protein in the retina.

In certain embodiments, an antisense oligonucleotide increases the amount of harmonin mRNA. In certain embodiments, an antisense oligonucleotide increases the amount of harmonin RNA. In certain embodiments, an antisense oligonucleotide increases the amount of harmonin protein. In certain embodiments, an antisense oligonucleotide increases the amount of harmonin mRNA in the ear. In certain embodiments, an antisense oligonucleotide increases the amount of harmonin RNA in the ear. In certain embodiments, an antisense oligonucleotide increases the amount of harmonin protein in the ear. In certain embodiments, an antisense oligonucleotide increases the amount of harmonin mRNA in the cochlea. In certain embodiments, an antisense oligonucleotide increases the amount of harmonin RNA in the cochlea. In certain embodiments, an antisense oligonucleotide increases the amount of harmonin protein in the cochlea. In certain embodiments, an antisense oligonucleotide increases the amount of harmonin mRNA in the retina. In certain embodiments, an antisense oligonucleotide increases the amount of harmonin RNA in the retina. In certain embodiments, an antisense oligonucleotide increases the amount of harmonin protein in the retina.

In certain embodiments, an antisense oligonucleotide increases the amount of correctly shaped stereocilia in the ear of an animal with Usher syndrome.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one symptom associated with Usher Syndrome. In certain embodiments, such administration results in amelioration of at least one symptom. In certain embodiments, administration of a pharmaceutical composition to an animal results in a decrease of cryptic spliced Usher mRNA in a cell of the animal. In certain embodiments, such administration results in an increase in normally spliced Usher mRNA and/or an increase in exon 3 skipped mRNA. In certain embodiments, such administration results in a decrease in cryptic Usher protein and an increase in normal Usher protein and/or truncated Usher protein lacking exon 3 amino acids. In certain embodiments, an Usher protein lacking exon 3 amino acids is preferred over cryptic Usher protein. In certain embodiments, administration of a pharmaceutical composition results in amelioration of auditory and/or visual defects. In certain embodiments, such amelioration is the reduction in severity of such defects. In certain embodiments, amelioration is the delayed onset of such defects. In certain embodiments, amelioration is the slowed progression of such defects. In certain embodiments, amelioration is the prevention of such defects. In certain embodiments, amelioration is the slowed progression of such defects. In certain embodiments, amelioration is the reversal of such defects.

In certain embodiments, one tests an animal for defects in the Usher gene. In certain embodiments, one identifies an animal having one or more splicing defects in the Usher gene. In certain embodiments, a pharmaceutical composition is administered to an animal identified as having a defect in the Usher gene. In certain embodiments, the animal is tested following administration.

In certain embodiments, a pharmaceutical composition comprising an antisense oligonucleotide is administered while the subject is in utero or very young. In certain embodiments, a pharmaceutical composition comprising an antisense oligonucleotide is administered while the subject is in utero or very young. In certain embodiments, a pharmaceutical composition comprising an antisense oligonucleotide is administered to the subject in utero. In certain embodiments, a pharmaceutical composition comprising an antisense oligonucleotide is administered to the subject from 0-15 days after birth. In certain embodiments, a pharmaceutical composition comprising an antisense oligonucleotide is administered to the subject from 0-12 days after birth. In certain embodiments, a pharmaceutical composition comprising an antisense oligonucleotide is administered to the subject from 0-10 days after birth. In certain embodiments, a pharmaceutical composition comprising an antisense oligonucleotide is administered to the subject from 0-9 days after birth. In certain embodiments, a pharmaceutical composition comprising an antisense oligonucleotide is administered to the subject from 0-8 days after birth. In certain embodiments, a pharmaceutical composition comprising an antisense oligonucleotide is administered to the subject from 0-7 days after birth. In certain embodiments, a pharmaceutical composition comprising an antisense oligonucleotide is administered to the subject from 0-6 days after birth. In certain embodiments, a pharmaceutical composition comprising an antisense oligonucleotide is administered to the subject from 0-5 days after birth. In certain embodiments, a pharmaceutical composition comprising an antisense oligonucleotide is administered to the subject from 0-4 days after birth. In certain embodiments, a pharmaceutical composition comprising an antisense oligonucleotide is administered to the subject from 0-3 days after birth. In certain embodiments, a pharmaceutical composition comprising an antisense oligonucleotide is administered to the subject from 0-2 days after birth. In certain embodiments, a pharmaceutical composition comprising an antisense oligonucleotide is administered to the subject from 0-1 days after birth. In certain embodiments, a pharmaceutical composition comprising an antisense oligonucleotide is administered to the subject from 2-5 days after birth. In certain embodiments, a pharmaceutical composition comprising an antisense oligonucleotide is administered to the subject from 3-5 days after birth.

In certain embodiments, a pharmaceutical composition comprising an antisense oligonucleotide is first administered while the subject is in utero or very young. In certain embodiments, a pharmaceutical composition comprising an antisense oligonucleotide is first administered while the subject is in utero or very young. In certain embodiments, a pharmaceutical composition comprising an antisense oligonucleotide is first administered to the subject in utero. In certain embodiments, a pharmaceutical composition comprising an antisense oligonucleotide is first administered to the subject from 0-15 days after birth. In certain embodiments, a pharmaceutical composition comprising an antisense oligonucleotide is first administered to the subject from 0-12 days after birth. In certain embodiments, a pharmaceutical composition comprising an antisense oligonucleotide is first administered to the subject from 0-10 days after birth. In certain embodiments, a pharmaceutical composition comprising an antisense oligonucleotide is first administered to the subject from 0-9 days after birth. In certain embodiments, a pharmaceutical composition comprising an antisense oligonucleotide is first administered to the subject from 0-8 days after birth. In certain embodiments, a pharmaceutical composition comprising an antisense oligonucleotide is first administered to the subject from 0-7 days after birth. In certain embodiments, a pharmaceutical composition comprising an antisense oligonucleotide is first administered to the subject from 0-6 days after birth. In certain embodiments, a pharmaceutical composition comprising an antisense oligonucleotide is first administered to the subject from 0-5 days after birth. In certain embodiments, a pharmaceutical composition comprising an antisense oligonucleotide is first administered to the subject from 0-4 days after birth. In certain embodiments, a pharmaceutical composition comprising an antisense oligonucleotide is first administered to the subject from 0-3 days after birth. In certain embodiments, a pharmaceutical composition comprising an antisense oligonucleotide is first administered to the subject from 0-2 days after birth. In certain embodiments, a pharmaceutical composition comprising an antisense oligonucleotide is first administered to the subject from 0-1 days after birth. In certain embodiments, a pharmaceutical composition comprising an antisense oligonucleotide is first administered to the subject from 2-5 days after birth. In certain embodiments, a pharmaceutical composition comprising an antisense oligonucleotide is first administered to the subject from 3-5 days after birth.

NONLIMITING DISCLOSURE AND INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT'CGAUCG," wherein $^{me}C$ indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1

Ush1c.216a Minigene

A plasmid comprising an Usher 1C mini-gene having a 216A mutation (Ush1c.216a) was prepared using standard molecular biology techniques. The Ush1c.216a plasmid comprised exons 2, 3, and 4, and introns 2 and 3. The mini-gene was under control of the CMV promoter. A schematic of the Ush1c.216a plasmid appears in FIG. 1*a*.

Example 2

Antisense Modulation of Usher Transcript

Figure 1B:
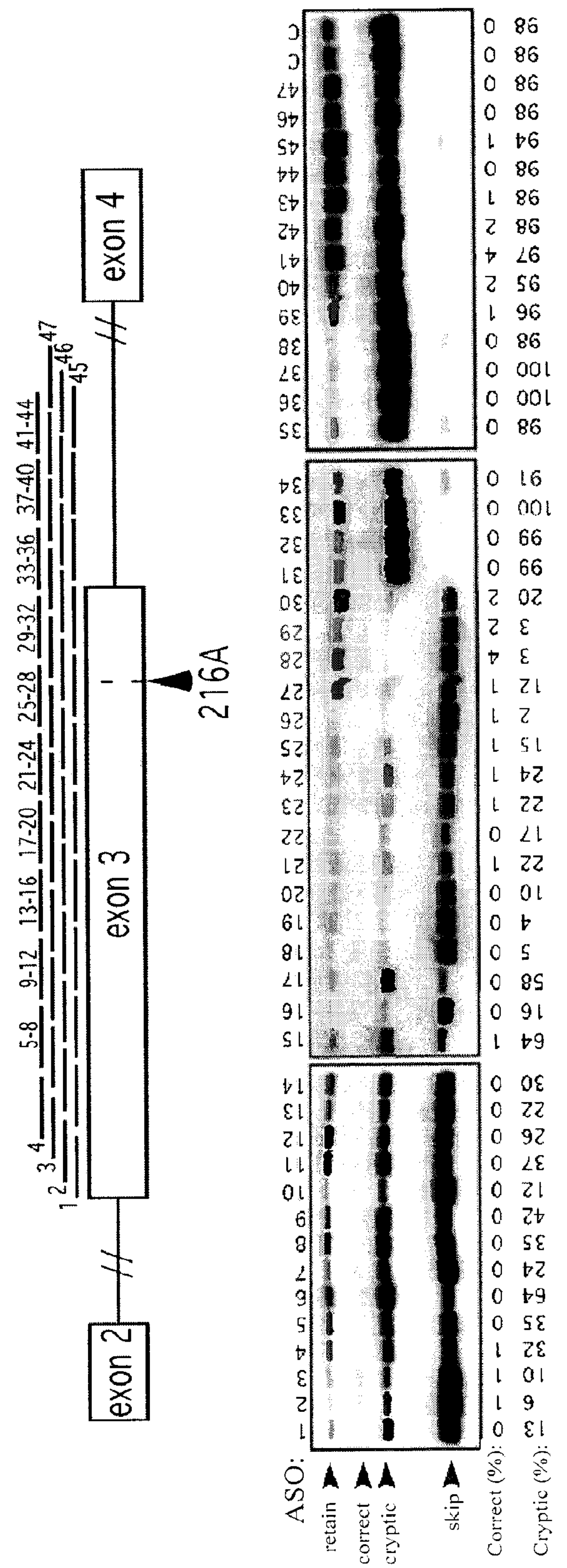
FIG. 1*b* shows a model of the minigene expression system (top) discussed in Example 1 and location of ASO targets on Ush1c exon 3 (bottom) discussed in Example 2.
Figure 1C:
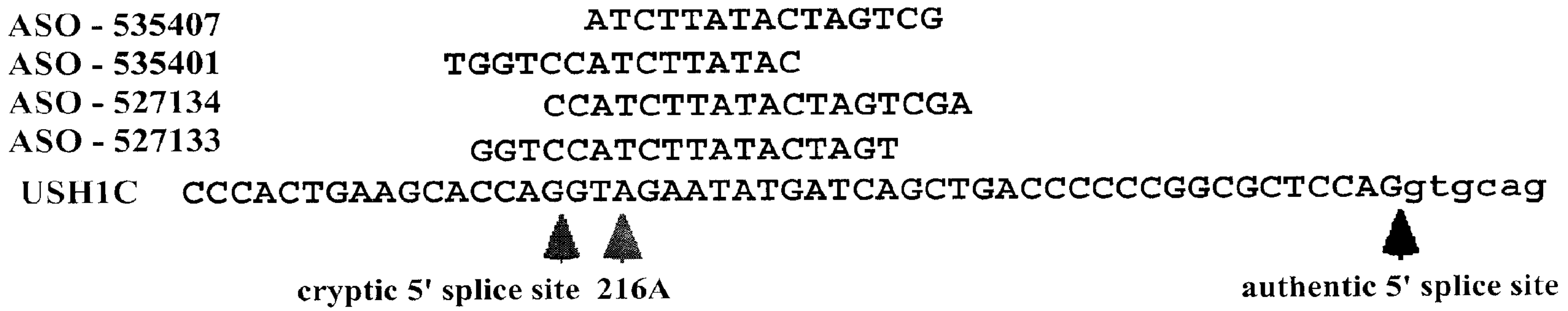
FIG. 1*c* shows a schematic of how each of Isis No. 527133 (SEQ ID NO: 29), 527134 (SEQ ID NO: 30), 535401 (SEQ ID NO: 50), and 535407 (SEQ ID NO: 56) target the cryptic splice site of the Ush1c gene having the 216A mutation (nucleotides 13568-13624 of SEQ ID NO: 1, SEQ ID NO: 59).

Antisense oligonucleotides complementary to different regions the Usher transcript were synthesized and tested for their ability to modulate splicing of the Usher mini-gene. Position on the Usher transcript is represented in FIG. 1*b*. Each nucleoside of the oligonucleotides was a 2'-MOE modified nucleoside (i.e., uniform 2'-MOE oligonucleotides). All internucleoside linkages were phosphorothioate linkages (i.e., uniform PS). All of the nucleobases were unmodified and cytosine bases were 5-meC.

To test the ability of the antisense oligonucleotides to modulate splicing, HeLa cells were co-transfected with the Ush1c.216a plasmid from Example 1 and an antisense oligonucleotide (or no antisense oligonucleotide in the case of the untreated control). RNA was collected from the cells and RT-PCR was used to identify Usher transcripts. The results are summarized in Table 1 below and in FIG. 1*b*. Start site is the position relative to SEQ ID NO 1.

TABLE 1

Modulation of splicing of USH1C pre-mRNA levels by modified oligonucleotides

| ISIS NO | 5'-Start Site | Sequence | Region | % cryptic splicing | SEQ ID NO |
|---|---|---|---|---|---|
| N/A | N/A | N/A | Untreated Control | 100 | N/A |
| 527106 | 138475 | ACGGCCACGTCCATGGTC | USH1C exon 3 | 13.39 | 2 |
| 527107 | 138480 | CGAGCACGGCCACGTCCA | USH1C exon 3 | 6.29 | 3 |
| 527108 | 138485 | TCCCACGAGCACGGCCAC | USH1C exon 3 | 9.93 | 4 |
| 527109 | 138490 | AGGTCTCCCACGAGCACG | USH1C exon 3 | 32.49 | 5 |
| 527110 | 138495 | GCTTCAGGTCTCCCACGA | USH1C exon 3 | 34.79 | 6 |
| 527111 | 138500 | GACCAGCTTCAGGTCTCC | USH1C exon 3 | 64.21 | 7 |
| 527112 | 138505 | TTGATGACCAGCTTCAGG | USH1C exon 3 | 23.89 | 8 |
| 527113 | 138510 | GTTCATTGATGACCAGCT | USH1C exon 3 | 34.68 | 9 |

TABLE 1-continued

Modulation of splicing of USH1C pre-mRNA levels by modified oligonucleotides

| ISIS NO | 5'-Start Site | Sequence | Region | % cryptic splicing | SEQ ID NO |
|---|---|---|---|---|---|
| 527114 | 138515 | GCTGGGTTCATTGATGAC | USH1C exon 3 | 41.71 | 10 |
| 527115 | 138520 | AGACGGCTGGGTTCATTG | USH1C exon 3 | 12.15 | 11 |
| 527116 | 138525 | GAGGCAGACGGCTGGGTT | USH1C exon 3 | 36.97 | 12 |
| 527117 | 138530 | AAACAGAGGCAGACGGCT | USH1C exon 3 | 26.32 | 13 |
| 527118 | 138535 | GCATCAAACAGAGGCAGA | USH1C exon 3 | 22.23 | 14 |
| 527119 | 138540 | GAATGGCATCAAACAGAG | USH1C exon 3 | 29.63 | 15 |
| 527120 | 138545 | CGGCCGAATGGCATCAAA | USH1C exon 3 | 63.65 | 16 |
| 527121 | 138550 | ATCAGCGGCCGAATGGCA | USH1C exon 3 | 15.79 | 17 |
| 527122 | 138555 | GTGGGATCAGCGGCCGAA | USH1C exon 3 | 57.54 | 18 |
| 527123 | 138560 | CTTCAGTGGGATCAGCGG | USH1C exon 3 | 5.27 | 19 |
| 527124 | 138563 | TGCTTCAGTGGGATCAGC | USH1C exon 3 | 3.61 | 20 |
| 527125 | 138566 | TGGTGCTTCAGTGGGATC | USH1C exon 3 | 9.68 | 21 |
| 527126 | 138569 | ACCTGGTGCTTCAGTGGG | USH1C exon 3 | 21.75 | 22 |
| 527127 | 138569 | ATATTCTACCTGGTGCTTCAGTGGG | USH1C exon 3 (G to A mt) | 16.77 | 23 |
| 527128 | 138571 | CTACCTGGTGCTTCAGTG | USH1C exon 3 (G to A mt) | 22.39 | 24 |
| 527129 | 138573 | TTCTACCTGGTGCTTCAG | USH1C exon 3 (G to A mt) | 24.45 | 25 |
| 527130 | 138576 | ATATTCTACCTGGTGCTT | USH1C exon 3 (G to A mt) | 14.89 | 26 |
| 527131 | 138577 | AGCTGATCATATTCTACCTGGTGCT | USH1C exon 3 (G to A mt) | 2.35 | 27 |
| 527132 | 138579 | ATCATATTCTACCTGGTG | USH1C exon 3 (G to A mt) | 12.13 | 28 |
| 527133 | 138581 | TGATCATATTCTACCTGG | USH1C exon 3 (G to A mt) | 2.85 | 29 |
| 527134 | 138584 | AGCTGATCATATTCTACC | USH1C exon 3 (G to A mt) | 2.70 | 30 |

TABLE 1-continued

Modulation of splicing of USH1C pre-mRNA levels by modified oligonucleotides

| ISIS NO | 5'-Start Site | Sequence | Region | % cryptic splicing | SEQ ID NO |
|---|---|---|---|---|---|
| 527135 | 138586 | TCAGCTGATCATATTCTA | USH1C exon 3 (G to A mt) | 19.98 | 31 |
| 527136 | 138589 | GGGTCAGCTGATCATATT | USH1C exon 3 | 98.82 | 32 |
| 527137 | 138591 | GGGGGTCAGCTGATCATA | USH1C exon 3 | 99.28 | 33 |
| 527138 | 138593 | CGCCGGGGGGTCAGCTGA | USH1C exon 3 | 99.60 | 34 |
| 527139 | 138598 | TGGAGCGCCGGGGGGTCA | USH1C exon 3 | 90.93 | 35 |
| 527140 | 138603 | GCACCTGGAGCGCCGGGG | USH1C exon 3/intron3 | 97.59 | 36 |
| 527141 | 138608 | CCTCTGCACCTGGAGCGC | USH1C exon 3/intron3 | 99.81 | 37 |
| 527142 | 138613 | GGCTTCCTCTGCACCTGG | USH1C exon 3/intron3 | 99.54 | 38 |
| 527143 | 138618 | CTGGTGGCTTCCTCTGCA | USH1C intron 3 | 97.64 | 39 |
| 527144 | 138623 | CCAGCCTGGTGGCTTCCT | USH1C intron 3 | 96.34 | 40 |
| 527145 | 138628 | TGCCTCCAGCCTGGTGGC | USH1C intron 3 | 94.86 | 41 |
| 527146 | 138633 | CCCCCTGCCTCCAGCCTG | USH1C intron 3 | 96.78 | 42 |
| 527147 | 138638 | CTCCACCCCCTGCCTCCA | USH1C intron 3 | 98.2 | 43 |
| 527148 | 138643 | GATCTCTCCACCCCCTGC | USH1C intron 3 | 97.94 | 44 |
| 527149 | 138648 | AGGGTGATCTCTCCACCC | USH1C intron 3 | 97.82 | 45 |
| 527150 | 138653 | CGCCCAGGGTGATCTCTC | USH1C intron 3 | 94.03 | 46 |
| 527151 | 138658 | TGCCCCGCCCAGGGTGAT | USH1C intron 3 | 97.74 | 47 |
| 527152 | 138663 | AGCACTGCCCCGCCCAGG | USH1C intron 3 | 97.83 | 48 |

As is evident from the table above, oligonucleotides having a 5'-start site between positions 13475 and 13585 demonstrated modulation of splicing of the Usher transcript. Thus, in certain embodiments active oligonucleotides have a 5'-start site between 13475 and 13585. In certain embodiments active oligonucleotides are complementary to a target sequence from 13475 to 13603 (the 3'-end of ISIS 527135). In certain embodiments active oligonucleotides are complementary to a target sequence from 13475 to 13604 (the 3'-end of a 20-mer having the same 5'-start site as ISIS 527135). In certain embodiments active oligonucleotides are complementary to a target sequence from 13475 to 13617 (the 3'-end of a 30-mer having the same 5'-start site as ISIS 527135).

In certain embodiments, active oligonucleotides have a 5'-start site between 13475 and 13495. In certain embodiments, active oligonucleotides have a 5'-start site between 13475 and 13495. In certain embodiments, active oligonucleotides have a 5'-start site between 13505 and 13540. In certain embodiments, active oligonucleotides have a 5'-start site between 13550 and 13586. In certain embodiments, active oligonucleotides have a 5'-start site between 13560 and 13586. In certain embodiments, active oligonucleotides have a 5'-start site between 13577 and 13584.

In certain embodiments active oligonucleotides are complementary to a target sequence from 13475 to 13415. In certain embodiments active oligonucleotides are complementary to a target sequence from 13475 to 13505. In certain embodiments active oligonucleotides are complementary to a target sequence from 13505 to 13515. In certain embodiments active oligonucleotides are complementary to a target sequence from 13505 to 13560. In certain embodiments active oligonucleotides are complementary to a target sequence from 13550 to 13606. In certain embodiments active oligonucleotides are complementary to a target sequence from 13560 to 13606. In certain embodiments active oligonucleotides are complementary to a target sequence from 13577 to 13604.

Example 3

Antisense Modulation of Usher Transcript

Additional antisense oligonucleotides complementary to Usher were synthesized and tested in HeLa cells transfected with the Ush1c.216a plasmid for their ability to modulate splicing as in Example 2. The antisense oligonucleotides were uniform 2'-MOE/uniform PS and all nucleobases were unmodified (all cytosines 5-meC) as in Example 2. Results are summarized in Table 2, below.

TABLE 2

Modulation of splicing of USH1C pre-mRNA levels by modified oligonucleotides

| ISIS NO | Start Site | Sequence | Target | % cryptic splicing | SEQ ID NO |
|---|---|---|---|---|---|
| 535400 | 138579 | ATATTCTACCTGGTG | USH1C exon 3 (G to A mt) | 53.03 | 49 |
| 535401 | 138580 | CATATTCTACCTGGT | USH1C exon 3 (G to A mt) | 61.03 | 50 |
| 535402 | 138581 | TCATATTCTACCTGG | USH1C exon 3 (G to A mt) | 66.12 | 51 |
| 535403 | 138582 | ATCATATTCTACCTG | USH1C exon 3 (G to A mt) | 41.61 | 52 |
| 535404 | 138583 | GATCATATTCTACCT | USH1C exon 3 (G to A mt) | 22.64 | 53 |
| 535405 | 138584 | TGATCATATTCTACC | USH1C exon 3 (G to A mt) | 27.35 | 54 |
| 535406 | 138585 | CTGATCATATTCTAC | USH1C exon 3 (G to A mt) | 20.08 | 55 |
| 535407 | 138586 | GCTGATCATATTCTA | USH1C exon 3 (G to A mt) | 16.79 | 56 |
| 535408 | 138587 | AGCTGATCATATTCT | USH1C exon 3 (G to A mt) | 72.49 | 57 |
| 535409 | 138588 | ATCATATTCTAC | USH1C exon 3 (G to A mt) | 98.38 | 58 |

As is evident from the table above, oligonucleotides having a 5'-start site between positions 13579 and 13587 demonstrated modulation of splicing of the Usher transcript. Thus, in certain embodiments active oligonucleotides have a 5'-start site between 13579 and 13587. In certain embodiments active oligonucleotides are complementary to a target sequence from 13579 to 13600 (the 3'-end of ISIS 535408). In certain embodiments active oligonucleotides are complementary to a target sequence from 13579 to 13607 (the 3'-end of a 20-mer having the same 5'-start site as ISIS 535408). In certain embodiments active oligonucleotides are complementary to a target sequence from 13475 to 13617 (the 3'-end of a 30-mer having the same 5'-start site as ISIS 535408).

In certain embodiments, active oligonucleotides have a 5'-start site between 13582 and 13586. In certain embodiments, active oligonucleotides have a 5'-start site between 13583 and 13586.

In certain embodiments active oligonucleotides are complementary to a target sequence from 13582 to 13606. In certain embodiments active oligonucleotides are complementary to a target sequence from 13583 to 13606.

Example 4

Antisense Modulation of Usher Transcript (Dose-Response)

Figure 1D:
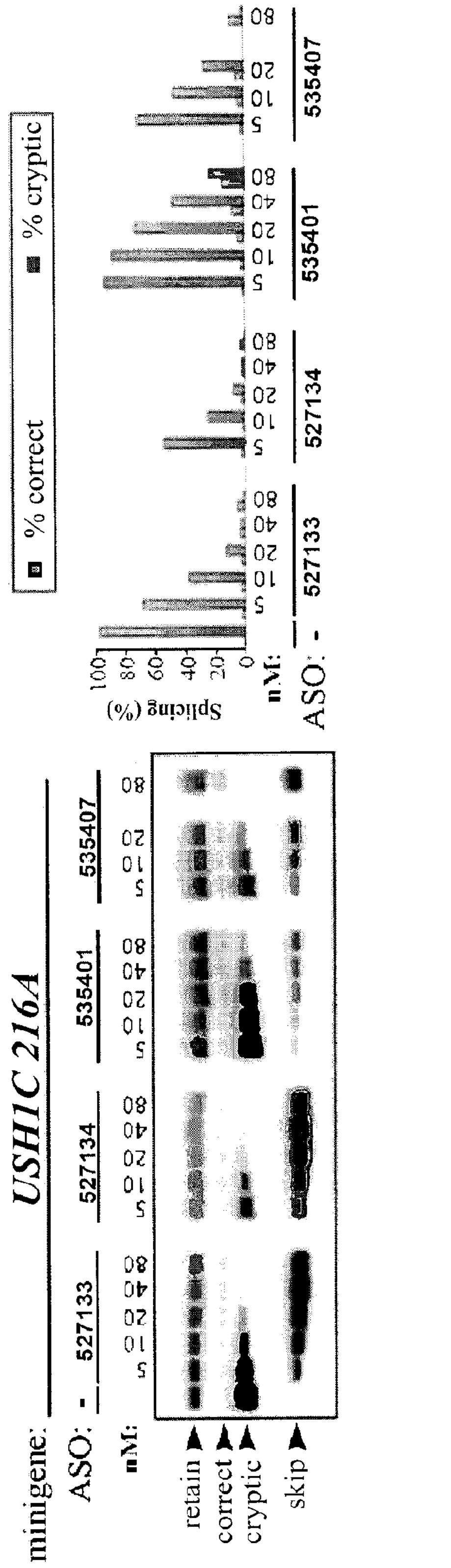
FIG. 1*d* shows RT-PCR analysis of RNA isolated from HeLa cells was transfected with either a WT or mutant (Ush1c.216a) minigene and treated with saline (−) or increasing amounts of Ush1c-specific 2'MOEs (final concentration 5, 10, 20, 40, 80 mM) discussed in Example 4. Cryptic splicing inhibition is quantitated in the histogram as the % cryptic splicing [cryptic/(cryptic+correct+skipped)×100].

Four of the antisense oligonucleotides above were separately tested at varying doses (0 (control), 5 nM, 10 nM, 20 nM, 40 nM, and 80 nM) as described above in Examples 2 and 3. RNA was collected and analyzed by RT-PCR, as above. Results are summarized in FIG. 1*d*. Each antisense oligonucleotide reduced the amount of cryptic spliced transcript and increased the amount of correctly spliced or exon 3-skipped transcript in a dose-dependent manner.

Example 5

In Vitro Dose Response

Figure 5A:
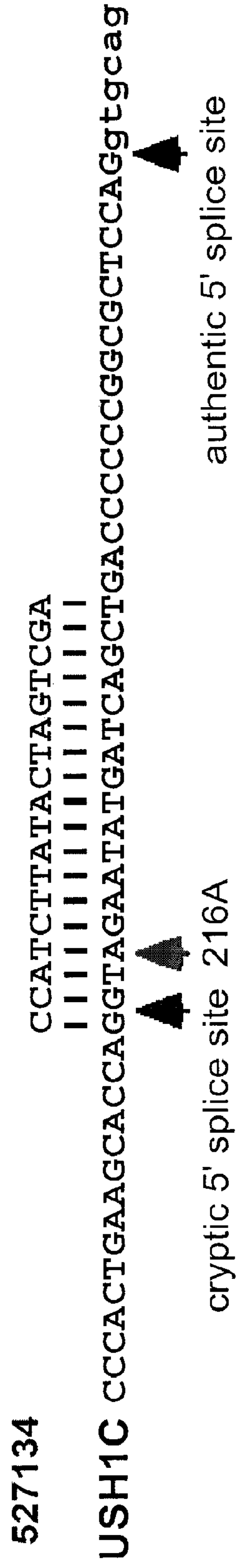
FIG. 5*a* shows a schematic of how Isis No. 527134 (SEQ ID NO: 30) targets the cryptic splice site of the Ush1c gene having the 216A mutation (nucleotides 13568-13624 of SEQ ID NO: 1, SEQ ID NO: 59).
Figure 5B:
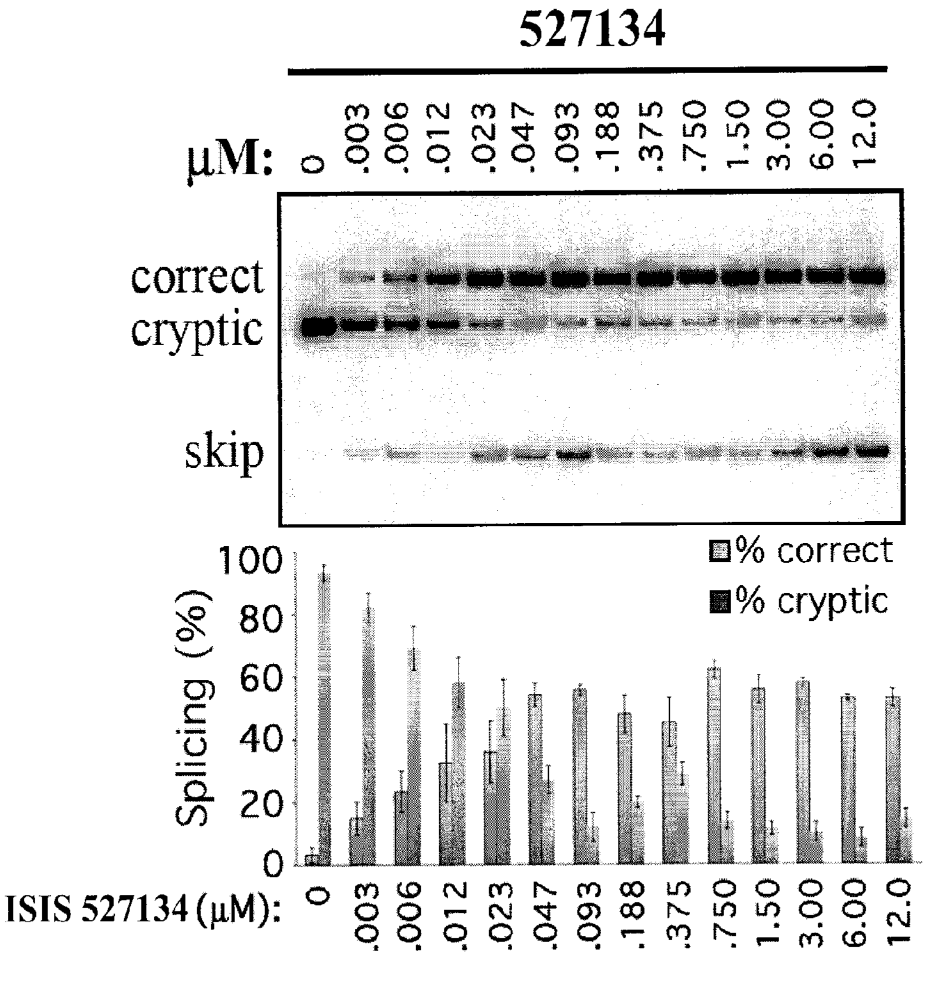
FIG. 5*b* shows RT-PCR analysis of liver cells treated with different concentrations of Isis No. 527134.
Figure 5C:
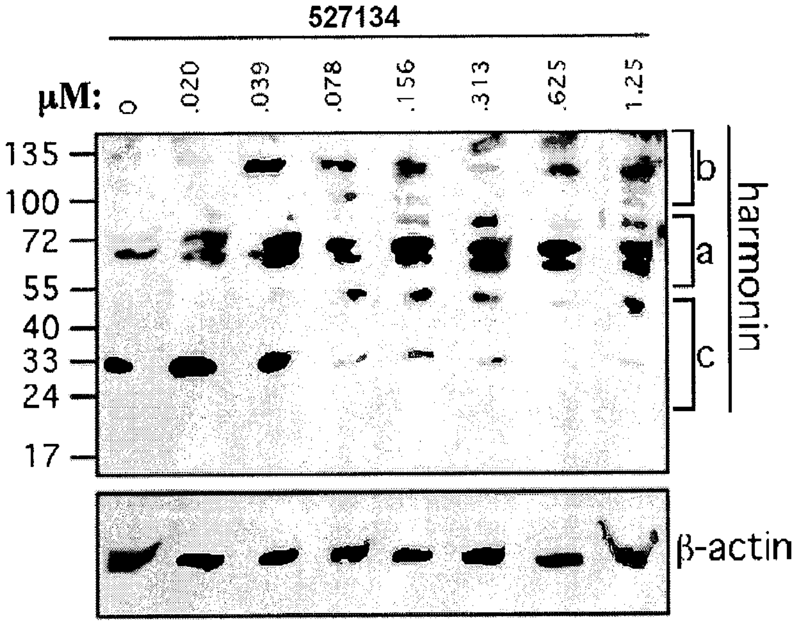
FIG. 5*c* shows Western-Blot analysis of harmonin expression in liver cells treated with different concentrations of Isis No. 527134.

Ush1c.216AA knock-in mouse kidney cell lines were cultured and were treated with increasing concentrations of Isis No. 527134. RNA was isolated and then analyzed by radiolabeled RT-PCR. Additionally, Western-blot analysis of harmonin protein in lysates from cells treated with increasing concentrations of Isis No. 527134 were measured. Results are summarized in FIGS. 5*a-c*. This example shows that antisense compounds blocked cryptic splicing and promoted correct splicing of the endogenous Ush1c.216A gene transcript when transfected into cultured cells derived from a Ush1c.216AA mouse kidney. This example also shows that antisense compounds increased harmonin protein expression when transfected into cultured cells derived from an Ush1c.216AA mouse kidney (see FIG. 5*c*).

Example 6

Figure 7:
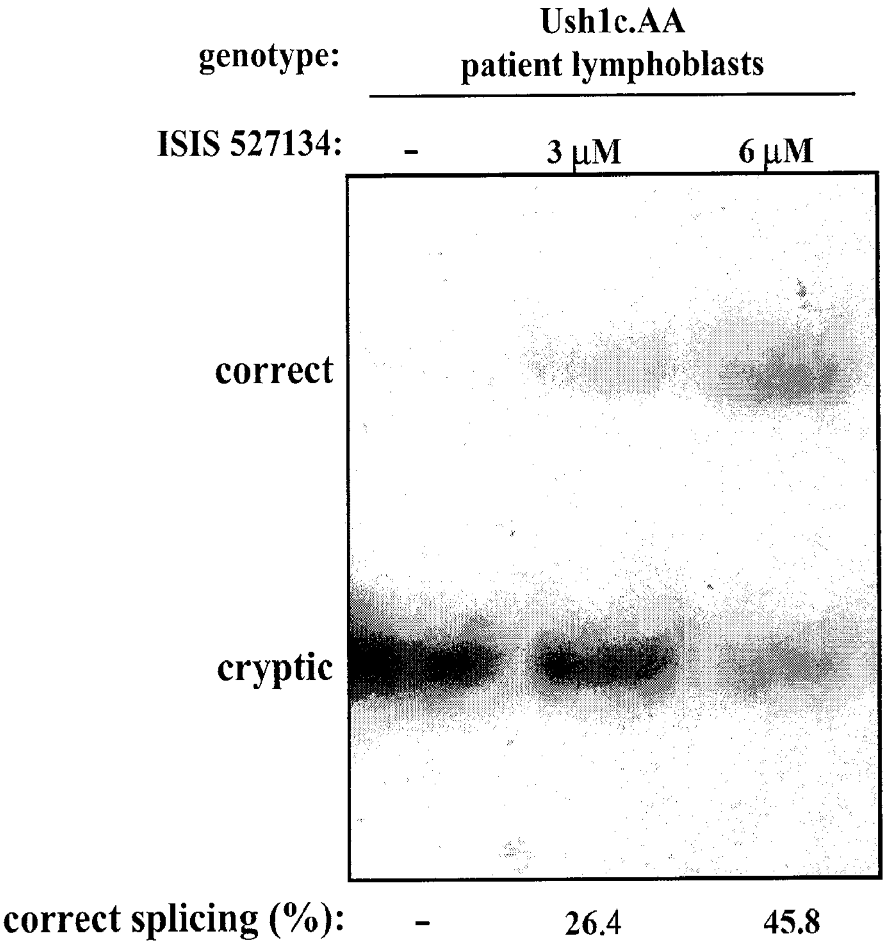
FIG. 7 shows RT-PCR analysis of RNA isolated from cultured lymphoblasts derived from an Ush1c patient and treated with Isis No. 527134.
Figure 8:
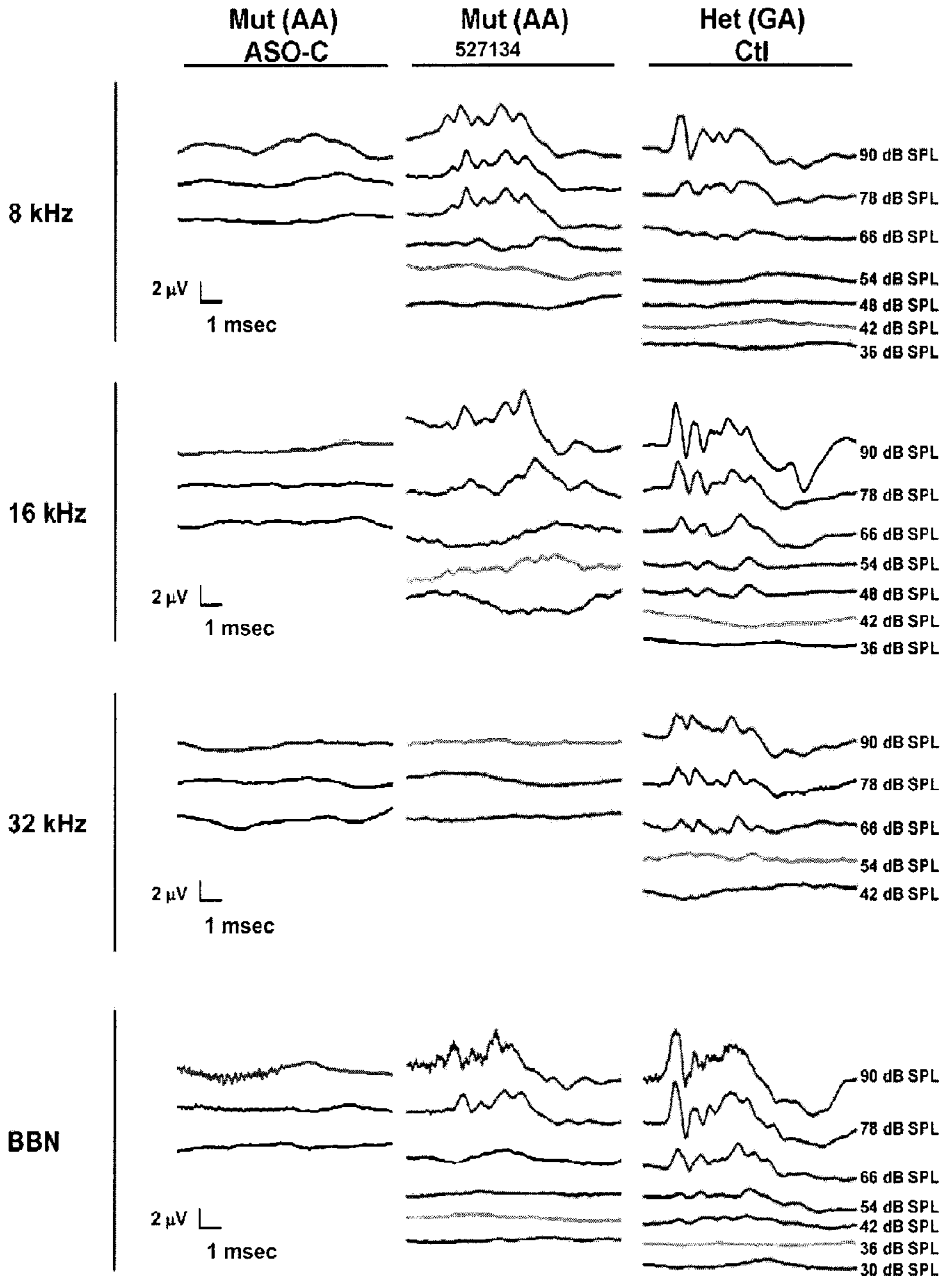
FIG. 8 shows audiograms of broad-band noise and pure-tone stimuli at 8 kHz, 16 kHz, 32 kHz for Ush1c.216AA mutant mice treated with Isis No. 527134, Ush1c.216AA mutant mice treated with a mismatched control, and heterozygous mice.
Figure 9:
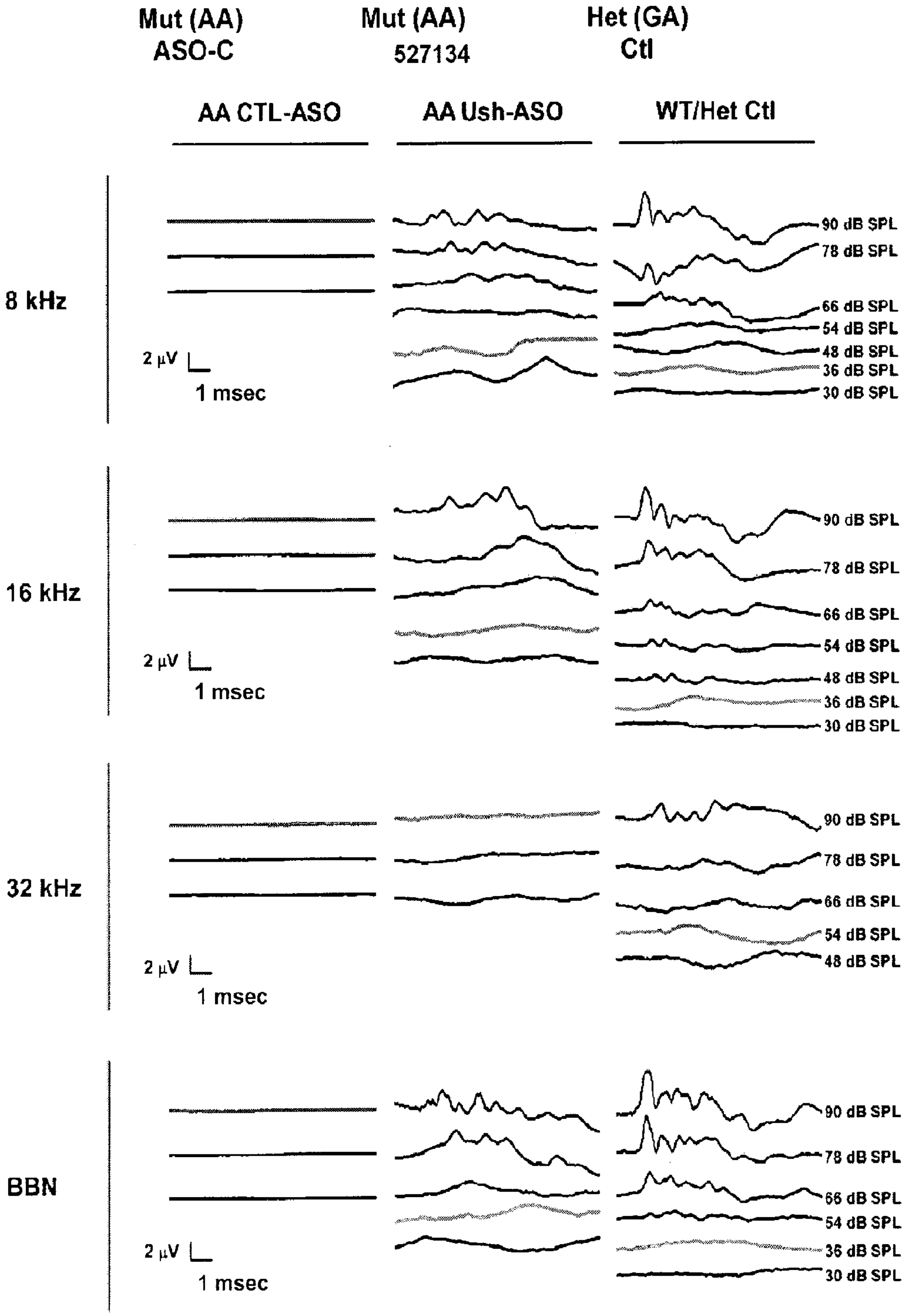
FIG. 9 shows audiograms of broad-band noise and pure-tone stimuli at 8 kHz, 16 kHz, 32 kHz at three months of age for Ush1c.216AA mutant mice treated with Isis No. 527134, Ush1c.216AA mutant mice treated with a mismatched control, and heterozygous mice.

In Vitro Modulation of the Usher Transcript in Ush1c.216AA Patient-Derived Lymphoblasts Cultured Ush1c.216AA patient-derived lymphoblasts were treated for 48 hours with 3 μM or 6 μM of Isis No. 527134 using Lipofectamine™ 2000. Primers specific to human Ush1c exon 3 and exon 4 were used to analyze the percent of correct splicing by RT-PCR. The results of the RT-PCR are shown in Table 3 below and in FIG. 7. This example demonstrates that antisense compounds can correct splicing in patient-derived Ush1c cells.

TABLE 3

Correction of splicing in patient-derived lymphoblasts

| Isis No. | Dose (μM) | % Correct Splicing |
|---|---|---|
| 527134 | 3 | 26.4 |
| 527134 | 6 | 45.8 |

Example 7

In Vivo Modulation of the Usher Transcript

Mice having the 216A mutation to the Ush1c gene have been described. Such mice have congenital hearing loss and retinal degeneration. Four of the above described antisense oligonucleotides (527133, 527134, 535401, and 535407) were administered to such mice to test their ability to modulate splicing in vivo.

Figure 1E:
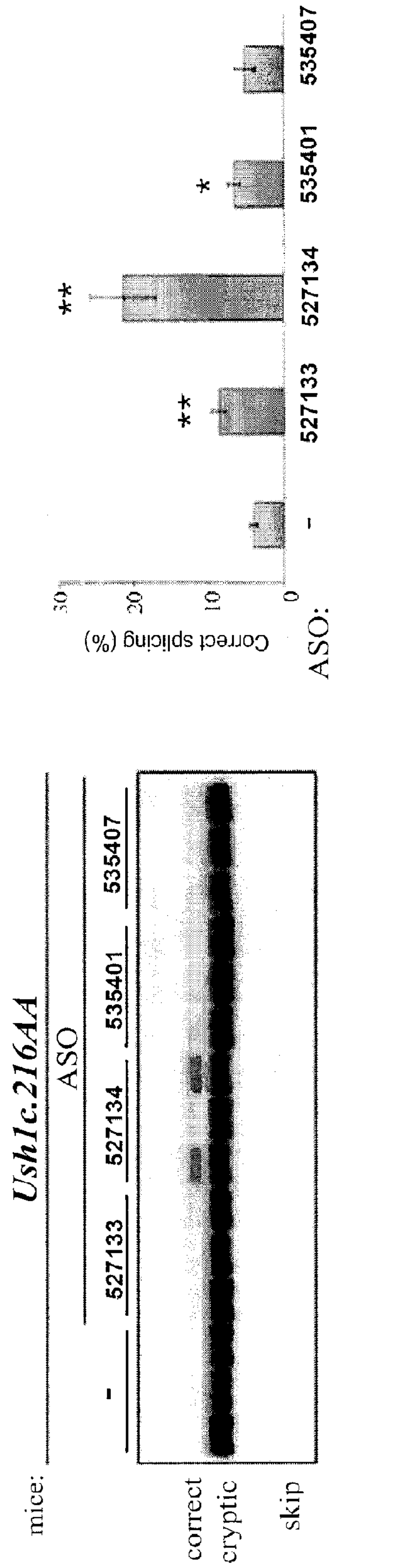
FIG. 1*e* shows RT-PCR analysis of the dose response of Isis No. 527133, 527134, 535401, and 535407 after administration to Ush1c.2166AA mice.

Doses of 50 mg/kg were administered by intraperitoneal injection twice each week for two weeks. Two days after the final injection, the mice were euthanized and RNA was isolated from various tissues. RNA was analyzed by radiolabeled RT-PCR. Splicing modulation was detected in the kidney and in the eye of treated mice. Results of correct kidney splicing are summarized in FIG. 1*e*.

Example 8

Tissue Specific In Vivo Modulation of the Usher Transcript

Mice having the 216A mutation to the Ush1c gene have been described. Such mice have congenital hearing loss and retinal degeneration. Ush1c.216AA mice were injected with Isis No. 527134 or a mismatched control oligonucleotide. Heterozygous Ush1c.216GA or wild-type Ush1c.216GG mice were also injected with Isis No. 527134.

RT-PCR analysis of RNA isolated from the retina of the mice was obtained at 32 days post birth (FIG. 12*a*). An increase in correct splicing was observed in the retina samples from Ush1c.216AA mice injected with Isis No. 527134. Western Blot analysis was also performed on protein isolated from the retina of the mice (FIG. 12*b*). Harmonin, encoded by the targeted Ush1c gene transcript was detected using an Ush1c specific antibody. B-actin was used as a loading control. Results of the Western Blot show that Ush1c.216AA mice injected with Isis No. 527134 had more harmonin protein in the retina than Ush1c.216AA mice injected with a mismatched control (FIG. 12*b*).

Additionally, Ush1c.216AA mice were injected with Isis No. 527134 or a mismatched control oligonucleotide at 5 days after birth. Samples of RNA isolated from the retina of the Ush1c.216AA mice injected with Isis No. 527134 were collected from mice at ages 12, 30, and 120 days. Samples of RNA isolated from the retina of the Ush1c.216AA mice injected with the mismatched control were collected from mice at 30 days of age. RT-PCR analysis was then performed on the samples. The results are shown in FIG. 12*c-d* and in Table 4. This example demonstrates that antisense oligonucleotides correct splicing in the retina.

TABLE 4

Quantitation of correct Ush1c splicing in the retina

| Age | Dose | % Correct | STDEV |
|---|---|---|---|
| 30 | Control | 0 | 0.006934 |
| 12 | 527134 | 1.9 | 1.734585 |
| 30 | 527134 | 0.9 | 1.287369 |
| 120 | 527134 | 0.2 | 0.098783 |

Example 9

In Vivo Modulation of the Usher Transcript—Dose Response

Figure 1F:
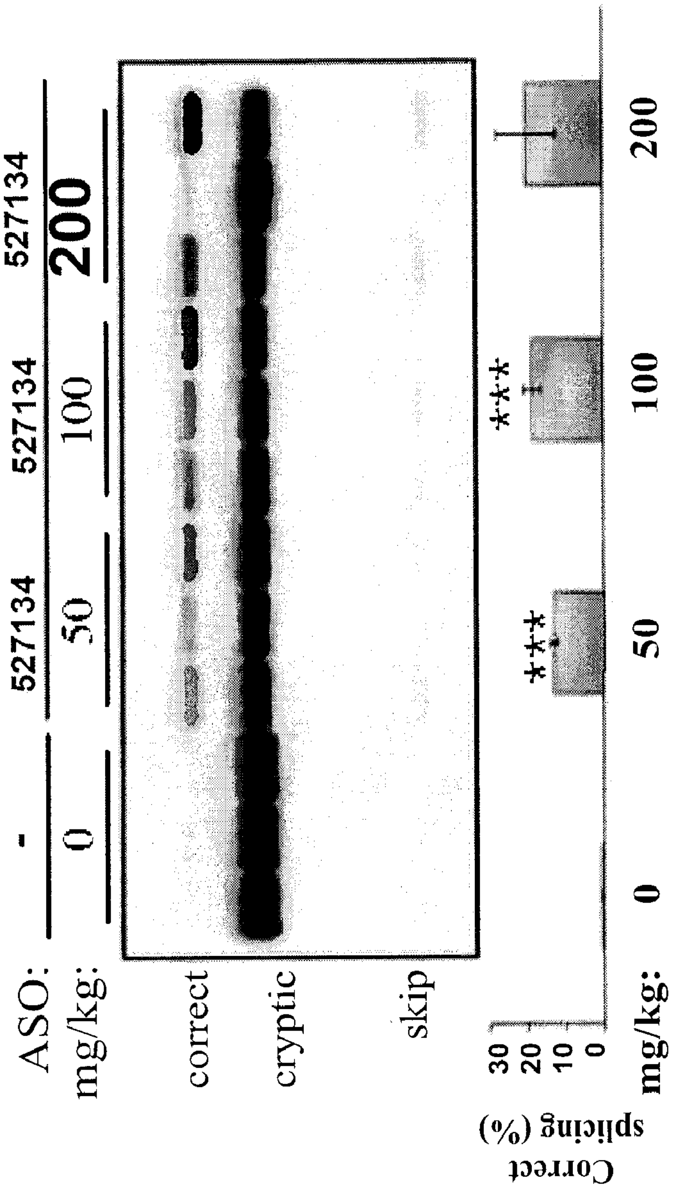
FIG. 1*f* shows RT-PCR analysis of mice kidney after the administration of Isis No. 527134 at different dosages.

Isis No. 527134 was administered via intraperitoneal injection in doses of 0 mg/kg, 50 mg/kg, 100 mg/kg, and 200 mg/kg twice weekly for two weeks to Ush1c.216AA mice. 24 hours after the final intraperitoneal injection, total RNA samples were prepared from the kidney and analyzed using radio labeled RT-PCR. The RT-PCR analysis showed that doses of Isis No. 527134 increased the amount of correct splicing. Results from the RT-PCR analysis are shown in Table 3 below and in FIG. 1*f*.

Figure 1G:
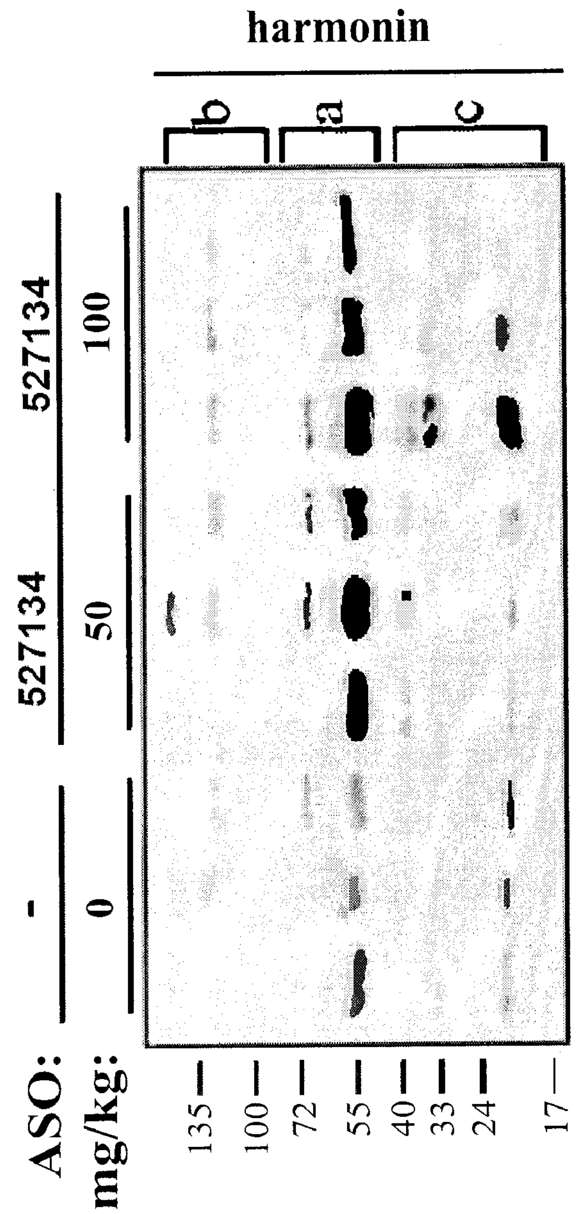
FIG. 1*g* shows Western-Blot analysis of lysates from Ush1c.216AA mice administered Isis No. 527134 at different dosages.

Additionally, harmonin protein levels were measured. Results from the Western-Blot analysis are shown in FIG. 1*g*. Western-Blot analysis of lysates from each of the Ush1c.216AA mice demonstrated that doses of Isis No. 527134 increased harmonin protein expression. This example demonstrates that Isis No. 527134 increases correct splicing of the Usher transcript in a dose-dependent manner.

TABLE 5

| RT-PCR Dose Response Study | | | | |
|---|---|---|---|---|
| Isis No./SEQ ID | Mouse | Dose (mg/kg) | % Correct | Average % Correct |
| 527134/30 | 1 | 0 | 0.4 | 0.5 |
| 527134/30 | 2 | 0 | 0.6 | |
| 527134/30 | 3 | 0 | 0.6 | |
| 527134/30 | 4 | 50 | 14.5 | 13 |
| 527134/30 | 5 | 50 | 11.3 | |
| 527134/30 | 6 | 50 | 13.2 | |
| 527134/30 | 7 | 100 | 16.3 | 18.5 |
| 527134/30 | 8 | 100 | 16.3 | |
| 527134/30 | 9 | 100 | 23 | |
| 527134/30 | 10 | 200 | 27.4 | 20.2 |

TABLE 5-continued

| RT-PCR Dose Response Study | | | | |
|---|---|---|---|---|
| Isis No./SEQ ID | Mouse | Dose (mg/kg) | % Correct | Average % Correct |
| 527134/30 | 11 | 200 | 4.6 | |
| 527134/30 | 12 | 200 | 28.6 | |

Example 10

Figure 2A:
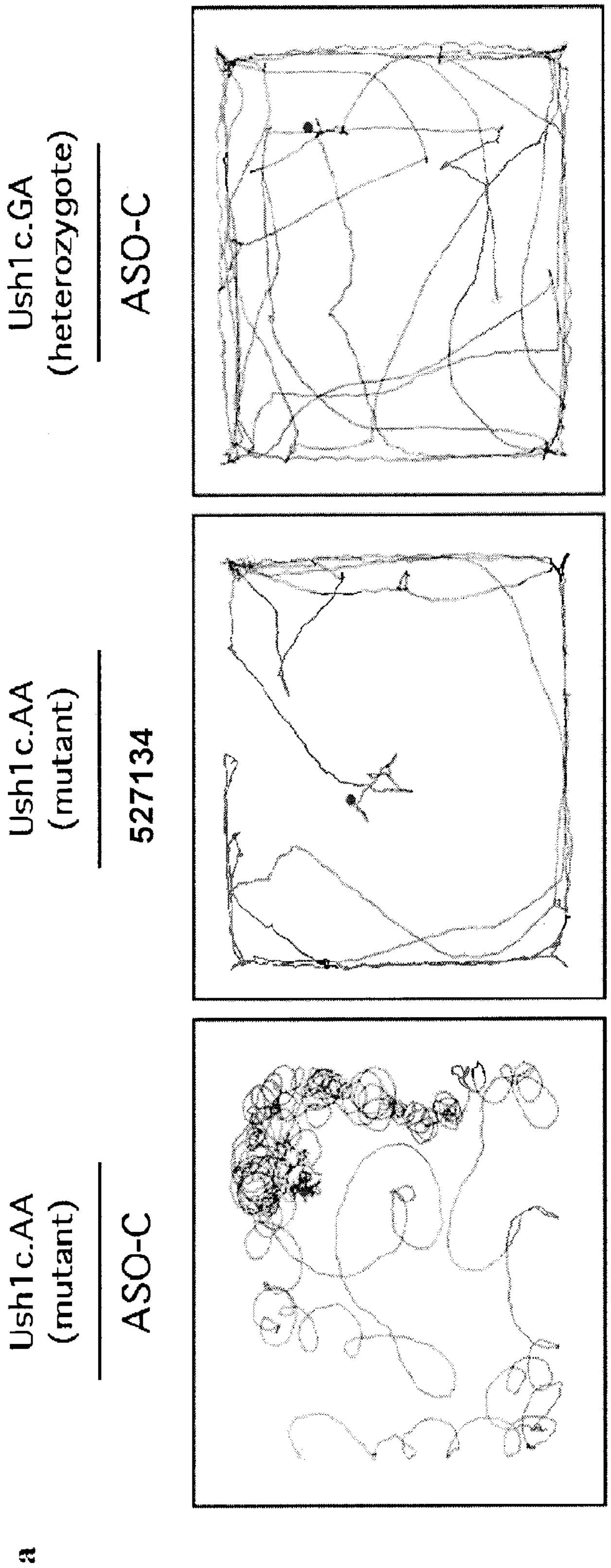
FIG. 2*a* shows the results of Ush1c.2166AA mice treated with a mismatched control, Ush1c.2166AA mice treated with Isis No. 527134, and heterozygous mice in an open-field pathway trace.

Restoration of Vestibular Function in Ush1c.216AA Mice a. Open Field Pathway Trace Neonatal Ush1c.216AA mice aged at 3, 5, 10, or 16 postnatal days (P3, P5, P10, or P16 respectively) were given a single 300 mg/kg intraperitoneal injection of either a mismatched 2'-MOE control antisense compound, or Isis No. 527134. Each mouse was then placed in an open field chamber and its behavior analyzed using ANY-maze behavioral tracking software (Stoelting Co, Wood Dale, Ill.). Untreated mice, or mice treated with a mismatched 2'-MOE compound were observed to display general hyperactivity and circular behavior when observed in an open-field pathway trace, which is characteristic of a severe vestibular effect. In contrast, the behavior and activity of mice treated with Isis No. 527134 was similar to heterozygote (216GA), or wild type (216GG) mice, with no circling, head-tossing, or hyperactivity observed in an open-field pathway trace. The results of the open-field pathway trace are shown in FIG. 2*a*. Additionally, there was no discernible behavioral difference between mice treated at P3, P5, or P10, whereas P16 treated mice exhibited circling behavior similar to untreated mice or mice treated with the a mismatched 2'-MOE compound. Mice treated at P5 with Isis No. 527134 were not observed to exhibit hyperactivity or circling behavior at 8 months of age. This example illustrates that antisense compounds can effectively cure vestibular function associated with Usher when delivered neonatally.

b. Open Field Trace-Quantitation of Rotations

Figure 2B:
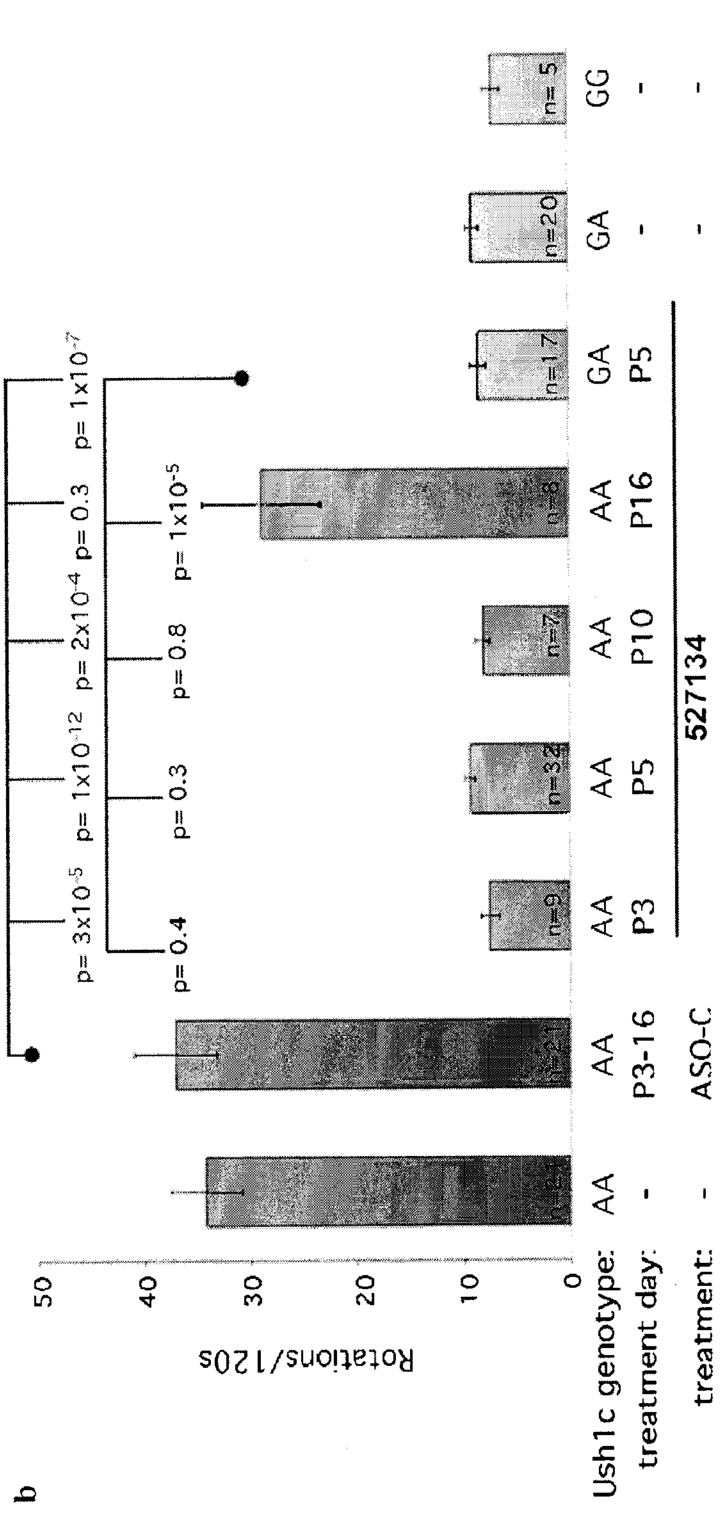
FIG. 2(B) shows results of RT-PCR analysis of splicing in the transfected HeLa cells, discussed in Example 2.

The number of rotations in 120 seconds was measured for each of the mice in the open-field pathway trace (see Example 10a). As illustrated in FIG. 2*b* and in Table 6 below, untreated mice, or mice treated with a mismatch antisense oligonucleotide rotated many times in a 120 second time period. Similarly, mice treated with Isis No. 527134 at 16 days postnatal were also observed to rotate many times within a 120 second time period. Mice treated at P3, P5, or P10 with Isis No. 527134 rotated far fewer times within a 120s period, and the number of rotations observed for mice treated at P3, P5, or P10 with Isis No. 527134 was consistent with the number of rotations observed for heterozygote (216GA) or wild type (216GG) mice. This example illustrates that antisense compounds can effectively cure vestibular function associated with Usher when delivered neonatally.

TABLE 6

| Table-rotations per 120 s-Open-field pathway trace | | | | | | | | | |
|---|---|---|---|---|---|---|---|---|---|
| Treatment Day | Untreated | P3, P5, P16 | P3 | P5 | P10 | P16 | P5 | Untreated | Untreated |
| Compound | None | control | 527134 | 527134 | 527134 | 527134 | 527134 | Untreated | Untreated |
| Genotype | AA | AA | AA | AA | AA | AA | AG | AG | GG |
| Average Rotations per 120 s | 34.2 | 37.0 | 7.6 | 9.4 | 8.1 | 28.9 | 8.5 | 9.1 | 7.2 |

c. Open Field Trace-Quantitation of Rotations 6-Months Post Treatment

Figure 2C:
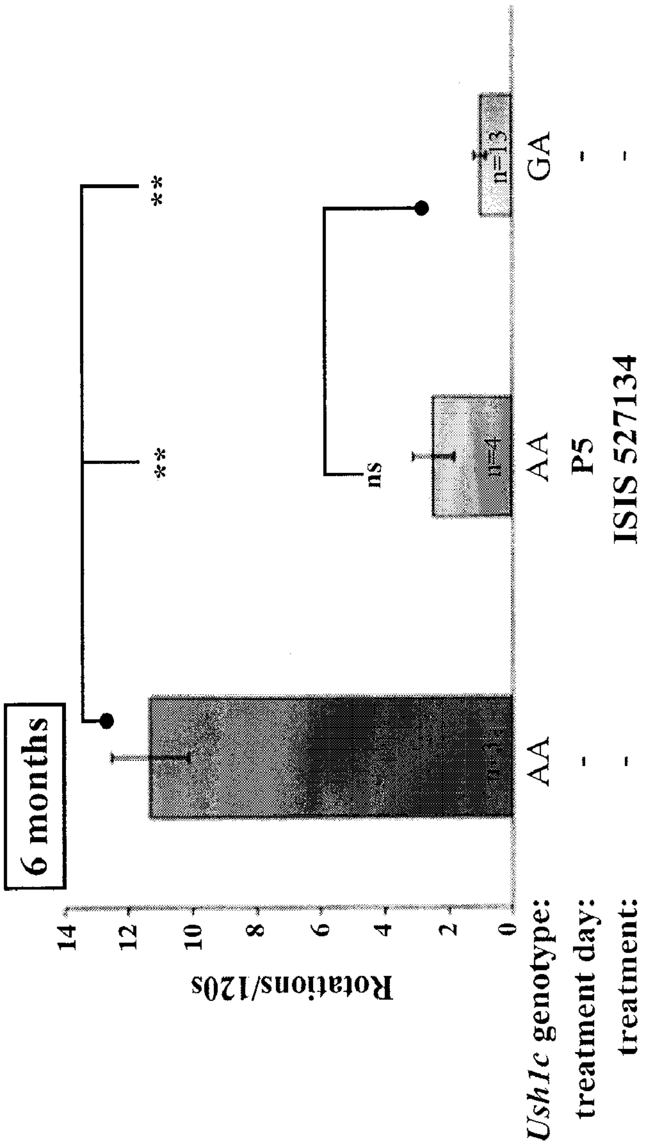
FIG. 2*c* shows the number of rotations of 6 month old Ush1c.2166AA mice treated with a mismatched control, Ush1c.2166AA mice treated with Isis No. 527134, and heterozygous mice in an open-field pathway trace.

Untreated heterozygote (216GA) mice, or Ush1c.216AA mice treated with Isis No. 527134 or a mismatched 2'-MOE compound were observed at 180 days. Ush1c.216AA mice treated with a mismatched control displayed general hyperactivity and circular behavior when observed in an open-field pathway trace, which is characteristic of a severe vestibular effect. In contrast, the behavior and activity of mice treated with Isis No. 527134 was similar to heterozygote (216GA) mice, with no circling, head-tossing, or hyperactivity observed in an open-field pathway trace. The results of the open-field pathway trace of mice at 180 days of age are given in Table 7 below and in FIG. 2*c*. This example demonstrates that antisense compounds can improve vestibular function and that improvements in vestibular function are maintained.

TABLE 7

| Table-rotations per 120 s-Open-field pathway trace | | | | |
|---|---|---|---|---|
| Compound | Genotype | Number of Mice | Average Rotations per 120 s | STDEV |
| None | 216GA | 13 | 1 | 0.7 |
| 527134 | Ush1c.216AA | 4 | 2.5 | 1.29 |
| Control | Ush1c.216AA | 3 | 11.333 | 2.1 |

d. Vestibular Phenotyping in Young and Aged Ush1c.216AA Mice Treated with Isis No. 527134

Three additional independent behavioral tests were used to quantify vestibular function in neonatal Ush1c.216AA mice or heterozygote (216GA) mice given a single 300 mg/kg intraperitoneal injection at 5 days after birth of either a mismatched 2'-MOE control antisense compound or Isis No. 527134. Quantitation of heterozygote (216GA) mouse behavior and Ush1c.216AA mouse behavior was performed on mice that were 2-3 months and 6-9 months old using a swim test, a trunk-curl test, and contact righting test.

Swim scores are based on a scoring system of O-3. A score of 0 indicates that the animal swims, a score of 1 indicates that irregular swimming was observed, a score of 2 indicates immobile floating, and a score of 3 indicates underwater tumbling and an inability to swim. The results of the swim test are given in Table 8 below. As illustrated in Table 8, Ush1c.216AA mice that received a dose of Isis No. 527134 and heterozygote (216GA) mice that received a dose of the mismatched control were observed to swim. Ush1c.216AA mice that received a dose of a mismatched control were observed tumbling underwater and were unable to swim.

The curl test indicates the number of animals in the group that curl towards their trunk when held by their tail and presented with a landing surface. The results of the curl test are given in Table 8. As illustrated in Table 8, Ush1c.216AA mice that received a dose of Isis No. 527134 and heterozygote (216GA) mice that received a dose of the mismatched control did not curl when held by their tail and presented with a landing surface, indicating a lack of vestibular dysfunction. Ush1c.216AA mice that received a dose of a mismatched control were observed curl when held by their tail and presented with a landing surface, indicating vestibular dysfunction.

Righting indicates the time an animal spent to right itself in an enclosed area when inverted. The results of the righting test are given in Table 8. As illustrated in Table 8, Ush1c.216AA mice that received a dose of Isis No. 527134 and heterozygote (216GA) mice that received a dose of the mismatched control were able to right themselves rapidly. Ush1c.216AA mice that received a dose of a mismatched control were observed to take a much longer amount of time to right themselves.

These examples show that antisense oligonucleotides can effectively curb the vestibular dysfunction associated with Usher, and that the lack of vestibular dysfunction is maintained.

TABLE 8

Vestibular Phenotyping in Young and Aged Ush1c.216AA Mice

| Genotype | Treatment | Age (months) | N | Test: Swim Test | Test: Curl (%) | Test: Righting (secs) |
|---|---|---|---|---|---|---|
| Ush1c.216AA | Control | 2-3 | 9 | 3 | 100 | 37.3 ± 6.9 |
| Ush1c.216AA | Control | 6-9 | 6 | 3 | 100 | 18.3 ± 10.2 |
| Ush1c.216AA | 527134 | 2-3 | 9 | 0 | 0 | 1 ± 0.2 |
| Ush1c.216AA | 527134 | 6-9 | 6 | 0 | 0 | 1 ± 0.3 |
| Ush1c.216GA | Control | 2-3 | 6 | 0 | 0 | 12 ± 4.7 |
| Ush1c.216GA | Control | 6-9 | 9 | 0 | 0 | 1 ± 0.3 |

Example 11

Correction of Deafness

Neonatal Ush1c.216AA mice were treated with either Isis No. 527134 or with a mismatched control oligonucleotide. Responses to high amplitude sound were then measured. Mice treated with a mismatched control oligonucleotide exhibited neither an initial startle response, defined as an ear-twitch and rapid head and body movement, nor a subsequent freezing response after the acoustic stimulus.

Figure 3A:
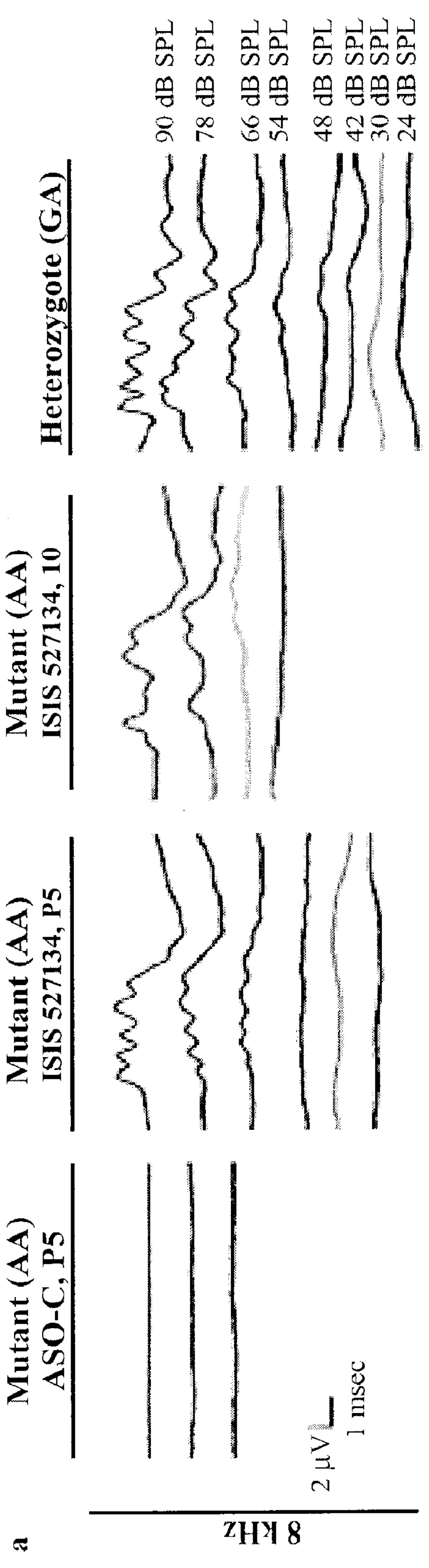
Figure 6:
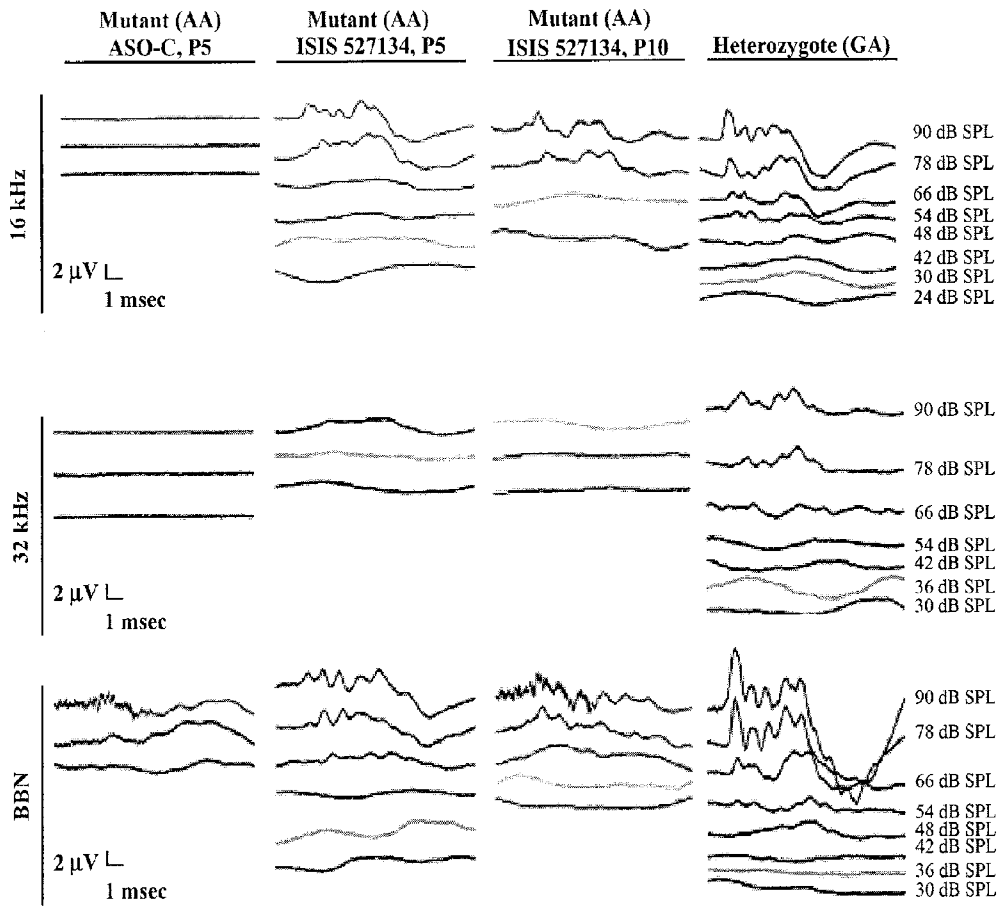
FIG. 6 shows audiograms of broad-band noise and pure-tone stimuli at 8 kHz, 16 kHz, 32 kHz at one month of age for Ush1c.216AA mutant mice treated with Isis No. 527134, Ush1c.216AA mutant mice treated with a mismatched control, and heterozygous mice.

To quantitatively assess hearing function, auditory-evoked brainstem response (ABR) analysis was performed. ABR thresholds to broad-band noise (BBN) and pure-tone stimuli at 8 kHz, 16 kHz, and 32 kHz were compared in 1-month old Ush1c.216AA mutant mice treated with Isis No. 527134 and those of age matched control mice. Two types of control mice were used: (i) treated and untreated wild type (wt, 216GG) and heterozygote (het, 216GA) mice; and (ii) Ush1c.216AA mutants treated with a mismatched control antisense oligonucleotide. Wild type (wt, 216GG) and heterozygote (het, 216GA) mice, whether untreated or treated with antisense oligonucleotides, had the expected thresholds of mice with normal hearing, as seen in FIGS. 3*a*-3*d*, FIG. 6, and Table 9. Like untreated Ush1c.216AA mutants, Ush1c.216AA mutants treated with the mismatched antisense oligonucleotide had an abnormal response or no response to broad-band noise or pure tones at 90 dB sound pressure level (see FIGS. 3*a*-3*d*). In contrast, Ush1c.216AA mutant mice treated between P3 and P5 with a single 300 mg/kg dose of Isis No. 527134 had normal audiograms with the expected 4-5 peaks and near normal thresholds to broad-band noise and pure-tone stimuli at 8 kHz and 16 kHz when compared to wild type (wt, 216GG) and heterozygote (het, 216GA) mice at 1 month, 2 months, and 3 months. These results are illustrated in FIGS. 3*a-d*, FIGS. 6, 8-9 and in Table 9. As illustrated in FIG. 3*b*, FIG. 6, and in Table 9, the treatment effect at one month on thresholds at 32 kHz for Ush1c.216AA mutant mice treated between P3 and P5 with a single 300 mg/kg dose of Isis No. 527134 was lower than Ush1c.216AA mutants treated with a mismatched control. Additionally, the treatment effect on thresholds at 32 kHz for Ush1c.216AA mutant mice treated between P3 and P5 with a single 300 mg/kg dose of Isis No. 527134 were higher when compared to wild type (wt, 216GG) and heterozygote (het, 216GA) mice at 32 kHz.

Figure 10A:
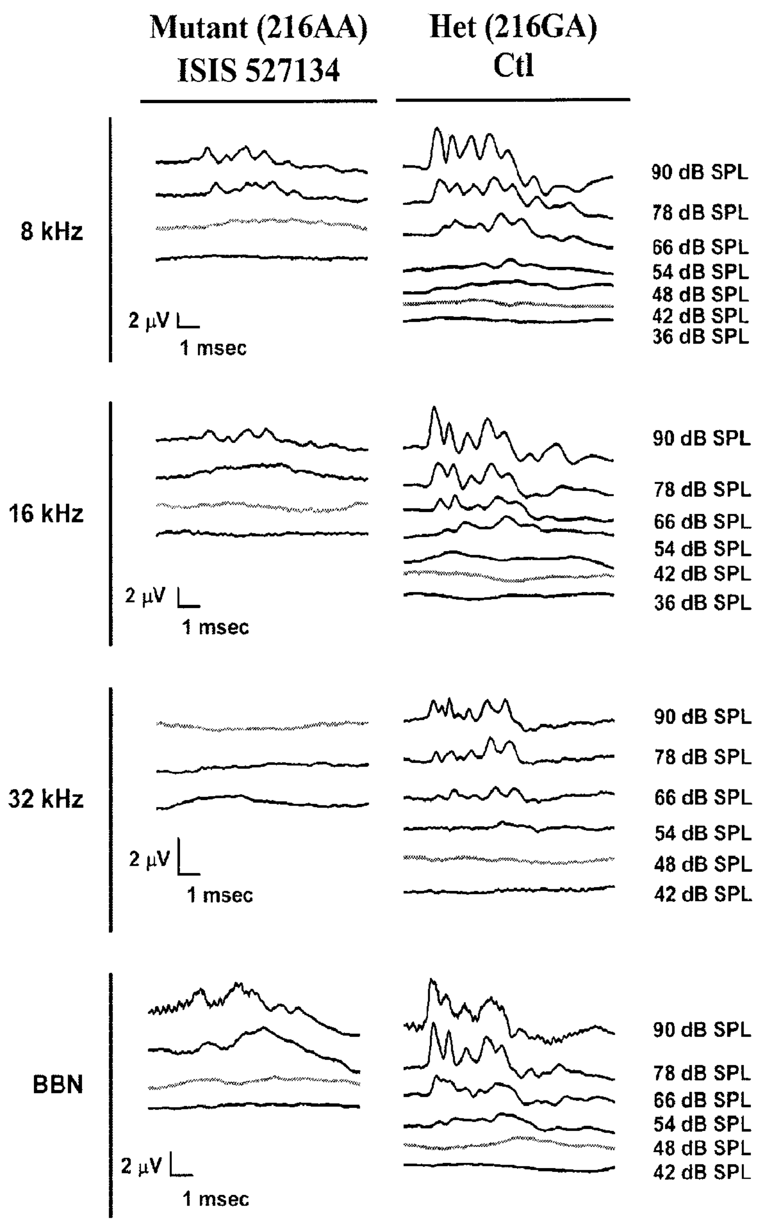
FIG. 10*a* shows audiograms of broad-band noise and pure-tone stimuli at 8 kHz, 16 kHz, 32 kHz at six months of age for Ush1c.216AA mutant mice treated with Isis No. 527134, Ush1c.216AA mutant mice treated with a mismatched control, and heterozygous mice.
Figure 10B:
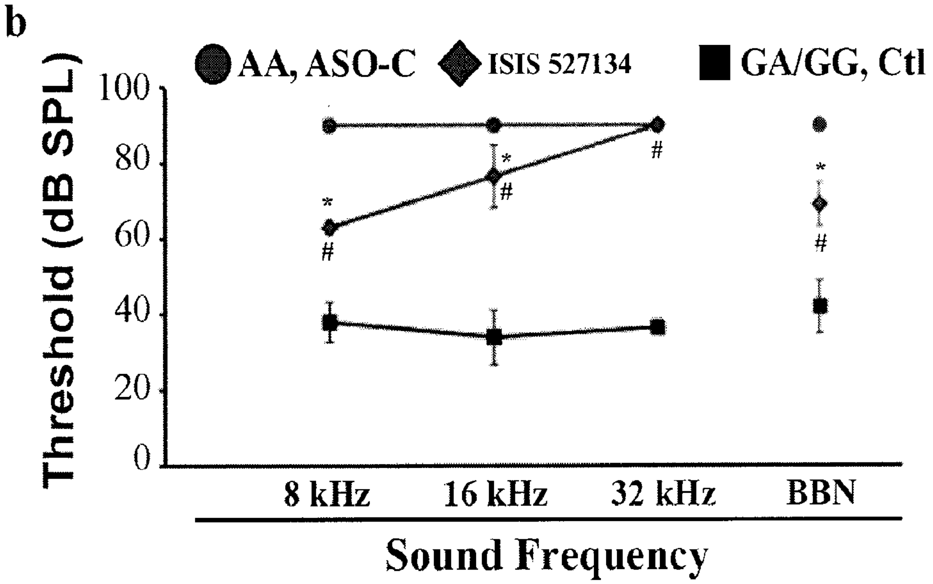
FIG. 10*b* shows the quantification of the audiograms of broad-band noise and pure-tone stimuli at 8 kHz, 16 kHz, 32 kHz at six months of age for Ush1c.216AA mutant mice treated with Isis No. 527134, Ush1c.216AA mutant mice treated with a mismatched control, and heterozygous mice.
Figure 10C:
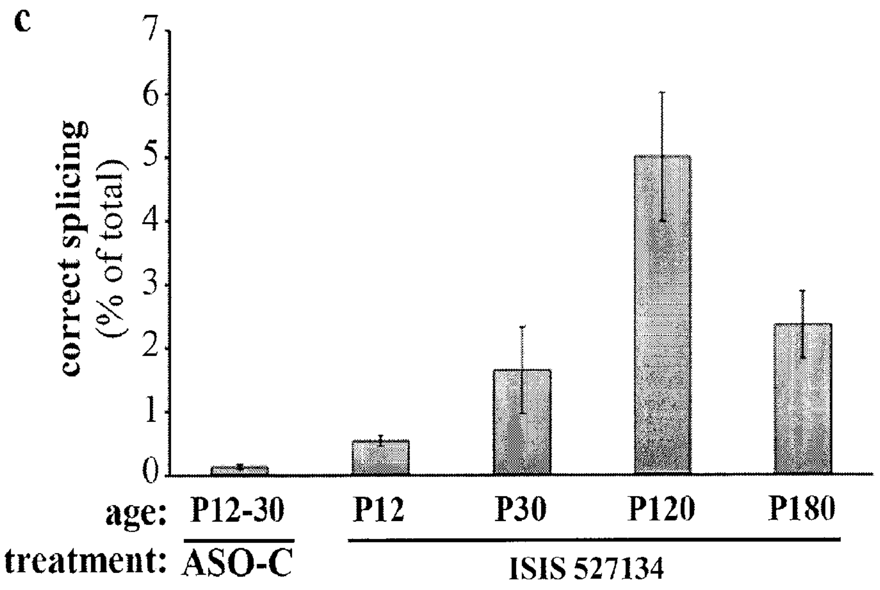
FIG. 10*c* shows the RT-PCR quantification of correct splicing at P12, P30, P120, and P180 in Ush1c.216AA mutant mice treated with Isis No. 527134.

At 6 months of age, Ush1c.216AA mutant mice treated with Isis No. 527134 at P5 still exhibited thresholds that were lower than untreated mutants, but higher than the wild-type and heterozygous control mice. These results are shown in FIGS. 10*a* and 10*b* and in Table 9. Quantitation of RT-PCR experiments measuring the amount of correctly spliced Ush1c transcripts showed that amount of correctly spliced Ush1c RNA at P30 was similar to that at P120 and P180 (FIG. 10*c*). This indicates that the effect of antisense oligonucleotides on splicing is stable and correlates with the observed ABR results. This example illustrates that the mice injected with a single antisense oligonucleotide-treatment early in life can hear at 1, 2, 3 and 6 months of age, indicating a long-term therapeutic correction of deafness.

Additionally, Ush1c.216AA mutant mice treated with a single 300 mg/kg dose of Isis No. 527134 at P10 had more variable responses with higher thresholds to broad-band noise and pure-tone stimuli than those treated between P3 and P5. Ush1c.216AA mutant mice treated with a single 300 mg/kg dose of Isis No. 527134 at P10 also had lower thresholds to broad-band noise and pure-tone stimuli than untreated mutants or mutants treated with a mismatched control antisense oligonucleotide. The results of mice treated at P10 are shown in FIGS. 3*a-b*, FIG. 6, and Table 9.

This example illustrates that treatment of Ush1c.216AA mice with antisense oligonucleotides rescued hearing over a broad range of frequencies.

TABLE 9

Auditory threshold in Ush1c.216AA mice treated with Isis No. 527134 and a mismatched control

| Month | Compound/ SEQ ID | | Frequency: 8 kHz | Frequency: 16 kHz | Frequency: 32 kHz | BBN |
|---|---|---|---|---|---|---|
| 1 | AG or GG | Threshold | 36 | 35 | 35 | 35 |
| | 527134/30 (P5) | (average) | 36 | 35 | 35 | 35 |
| | 527134/30 (P10) | | 72 | 73 | 93 | 78 |
| | Control | | 81 | 86 | 90 | 89 |

TABLE 9-continued

| Auditory threshold in Ush1c.216AA mice treated with Isis No. 527134 and a mismatched control | | | | | |
|---|---|---|---|---|---|
| | | Frequency | | | |
| Month | Compound/ SEQ ID | 8 kHz | 16 kHz | 32 kHz | BBN |
| 2 | AG or GG | 42 | 40 | 50 | 39 |
| | 527134/30 (P5) | 47 | 52 | 90 | 49 |
| | Control | 90 | 90 | 90 | 90 |
| 3 | AG or GG | 34 | 36 | 48 | 38 |
| | 527134/30 (P5) | 48 | 60 | 90 | 48 |
| | Control | 90 | 90 | 90 | 90 |
| 6 | AG or GG | 38 | 34 | 37 | 42 |
| | 527134/30 (P5) | 63 | 77 | 90 | 69 |
| | Control | 90 | 90 | 90 | 90 |

Example 12

Restoration of Splicing, Protein Expression, and Hair Cells in Mice a. Cochlea

Figure 4A:
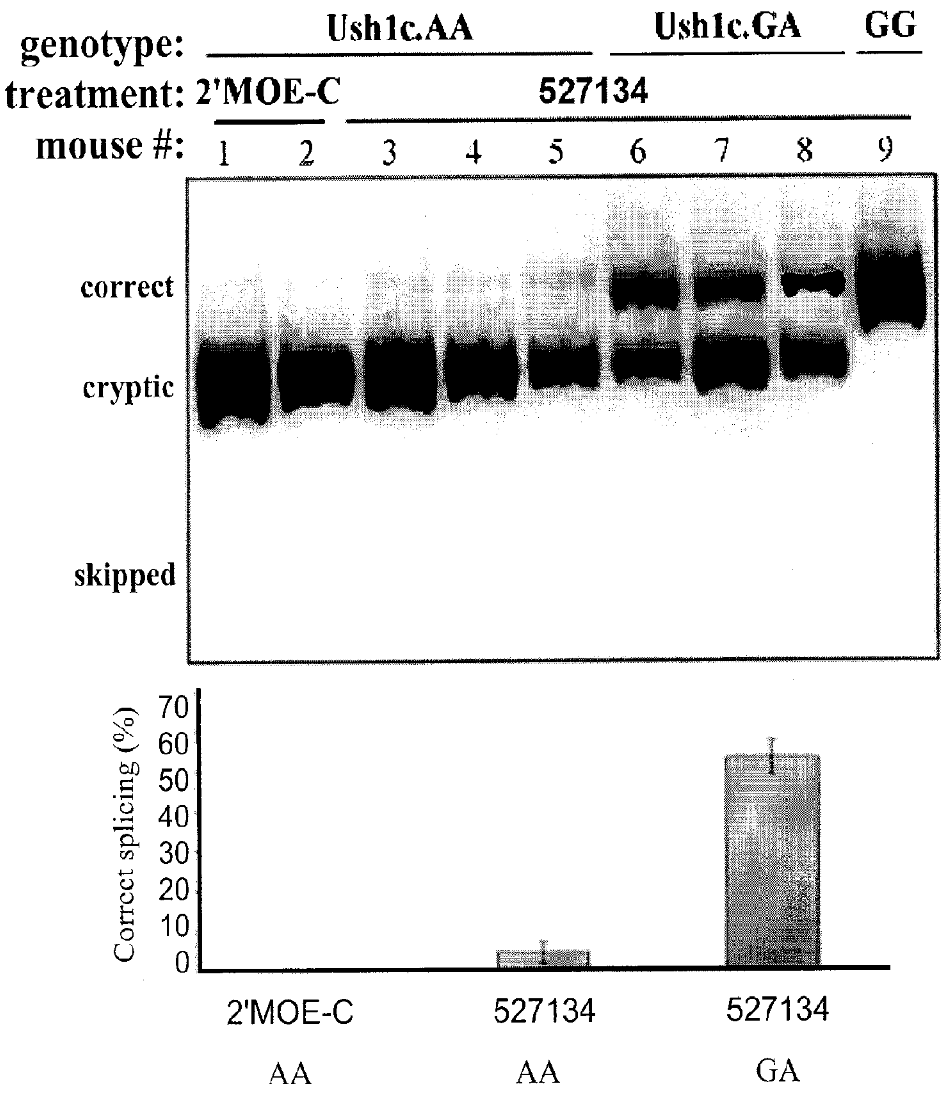
FIG. 4*a* shows RT-PCR analysis of Ush1c.2166AA mice treated with a mismatched control, Ush1c.2166AA mice treated with Isis No. 527134, heterozygous mice treated with Isis No. 527134, and wild-type mice treated with treated with Isis No. 527134.
Figure 4B:
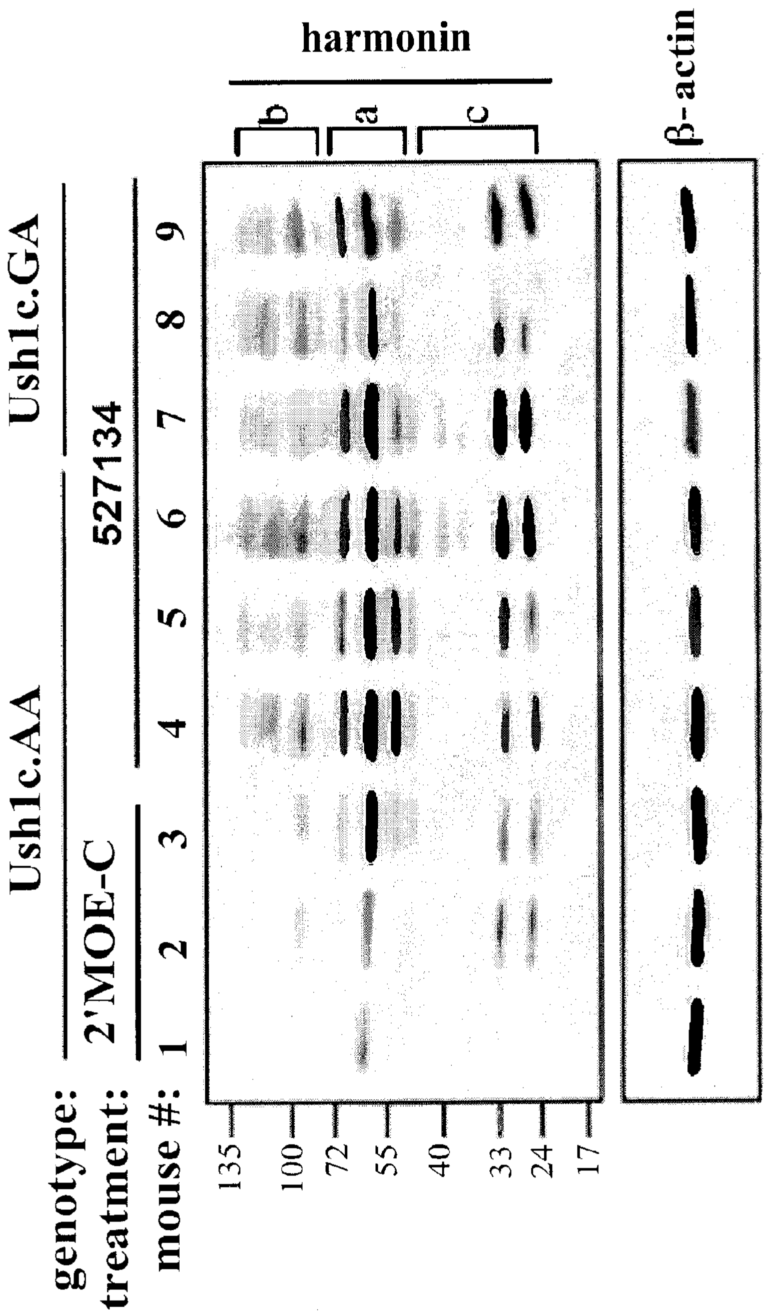
FIG. 4*b* shows a Western-Blot of harmonin abundance in Ush1c.2166AA mice treated with a mismatched control, Ush1c.2166AA mice treated with Isis No. 527134, and heterozygous mice treated with Isis No. 527134.

Cochleae from mice injected at P5 with 300 mg/kg Isis No. 527134 or a mismatched control were harvested at P30 and subjected to RT-PCR and western blot analyses. As shown in Table 10, correct exon 3 splicing was observed in the Ush1c.216AA mice treated with Isis No. 527134. Correct exon 3 splicing was not seen in Ush1c.216AA mice treated with a mismatched control (FIG. 4*a*). Likewise, harmonin protein abundance was higher in cochleae isolated from Ush1c.216AA mice treated with Isis No. 527134 compared to Ush1c.216AA mice treated with a mismatched control. Additionally, harmonin protein abundance in the Ush1c.216AA mice treated with Isis No. 527134 was similar to harmonin protein levels in samples from control 216GA mice (FIG. 4*b*). A low level of harmonin protein was detected in Ush1c.216AA mice that were treated with the mismatched control.

TABLE 10

| Cochlea RNA | | | | |
|---|---|---|---|---|
| Genotype | Treatment | Mouse | % correct splicing | Average % of correct splicing |
| AA | control | 361 | 0.2 | 0.4 |
| | | 366 | 0.5 | |
| | | 367 | 0.5 | |
| | | 368 | 0.8 | |
| | untreated | 261 | 0.1 | |
| | | 257 | 0.1 | |
| | 527134/30 | 350 | 51.7 | 5.6 |
| | | 353 | 14.7 | |
| | | 357 | NA | |
| | | 233 | 6.4 | |
| | | 232 | 0.8 | |
| | | 231 | 0.4 | |
| AG | 527134/30359 | 351 | 47.1 | 50.8 |
| | | 352 | 52.4 | |
| | | 354 | 72.2 | |
| | | 356 | 59.9 | |
| | | 359 | 58.0 | |
| | | 360 | 62.4 | |
| | | 264 | 30.2 | |
| | | 263 | 28.2 | |
| | | 248 | 46.4 | |
| | | 358 | 75.3 | |

TABLE 10-continued

| Cochlea RNA | | | | |
|---|---|---|---|---|
| Genotype | Treatment | Mouse | % correct splicing | Average % of correct splicing |
| | control | 362 | 43.3 | 41.1 |
| | | 363 | 11.8 | |
| | | 369 | 34.4 | |
| | | 370 | 74.9 | |
| GG | | 262 | 99.9 | |

Example 13

Immunohistochemistry Analysis of Whole Cochleae

Figure 4C:
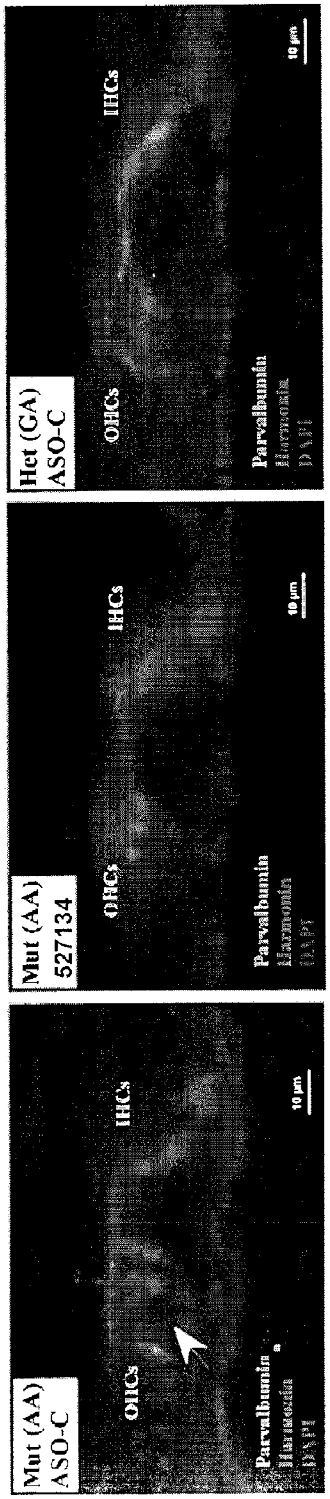
FIGS. 4*c* and 4*d* show immunohistochemistry analysis of whole cochleae in Ush1c.2166AA mice treated with a mismatched control, Ush1c.2166AA mice treated with Isis No. 527134, heterozygous mice treated with a mismatched control, and wild-type mice treated with treated with a mismatched control.
Figure 4D:
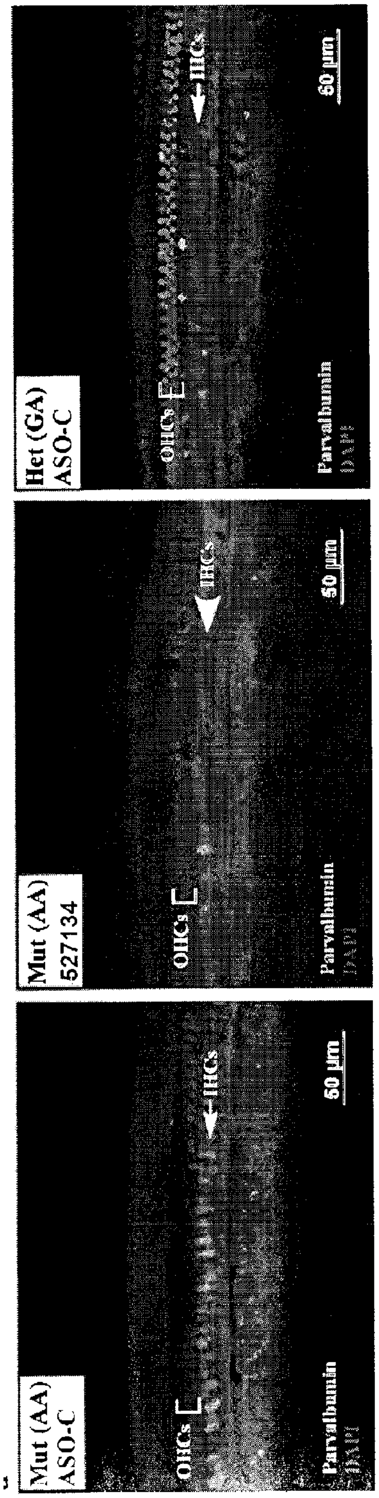

Immunohistochemistry analysis of whole cochleae showed rescue of hair cell morphology with antisense oligonucleotide treatment, consistent with the ABR data in Example 11. Hair cells labeled with anti-parvalbumin antibodies (green) from Ush1c.216AA mice treated with Isis No. 527134 have normal morphology and organized inner and outer rows at the apex-middle turn region similar to control cochleae of 216GA heterozygous animals (FIG. 4*c*). At P30, when hearing development is complete, harmonin (red) can be seen mostly at the apex of the hair cells (FIG. 4*c*). Using a pan-specific antibody, harmonin isoforms were detected in mice given the mismatched control to recognize the truncated protein. Hair cells of the mid-basal region of the cochlea of Ush1c.216AA mice treated with Isis No. 527134 were disorganized relative to the heterozygote 216GA mice but exhibited less evidence of degeneration compared to Ush1c.216AA mutants treated with a mismatched control antisense oligonucleotide, where hair cell loss and degeneration was pronounced. These results are shown in FIG. 4*d*.

Example 14

Stereocilia Morphology in Ush1c.216AA and 216GA Heterozygous Mice

Figure 4E:
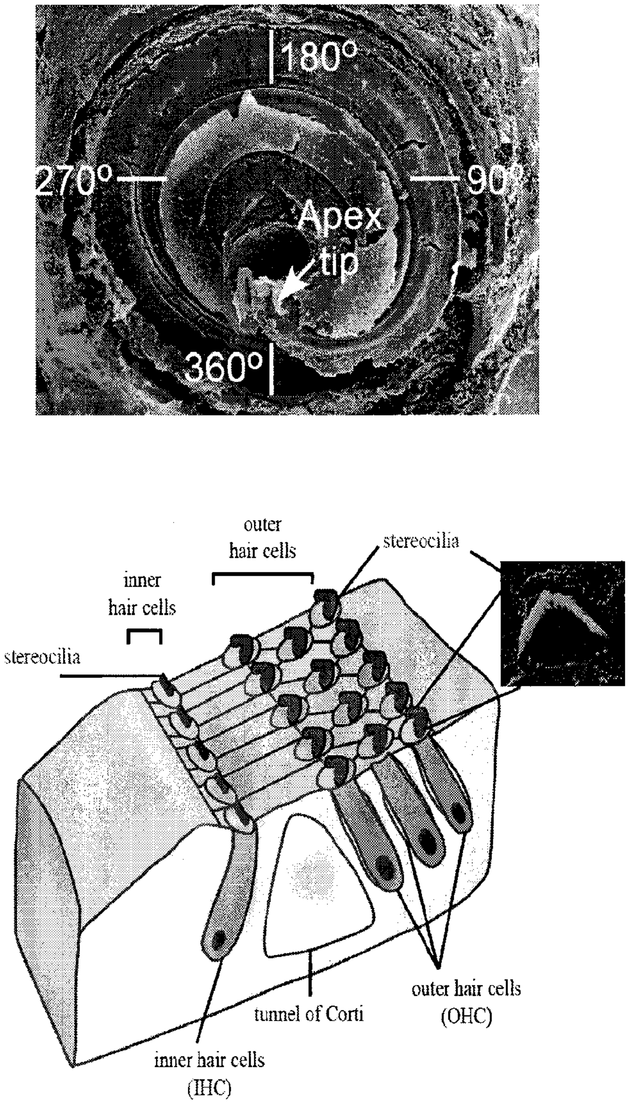
FIG. 4*e* illustrates the stereocilia and a Scanning Electron Microscopy (SEM) image of the stereocilia.
Figure 4F:
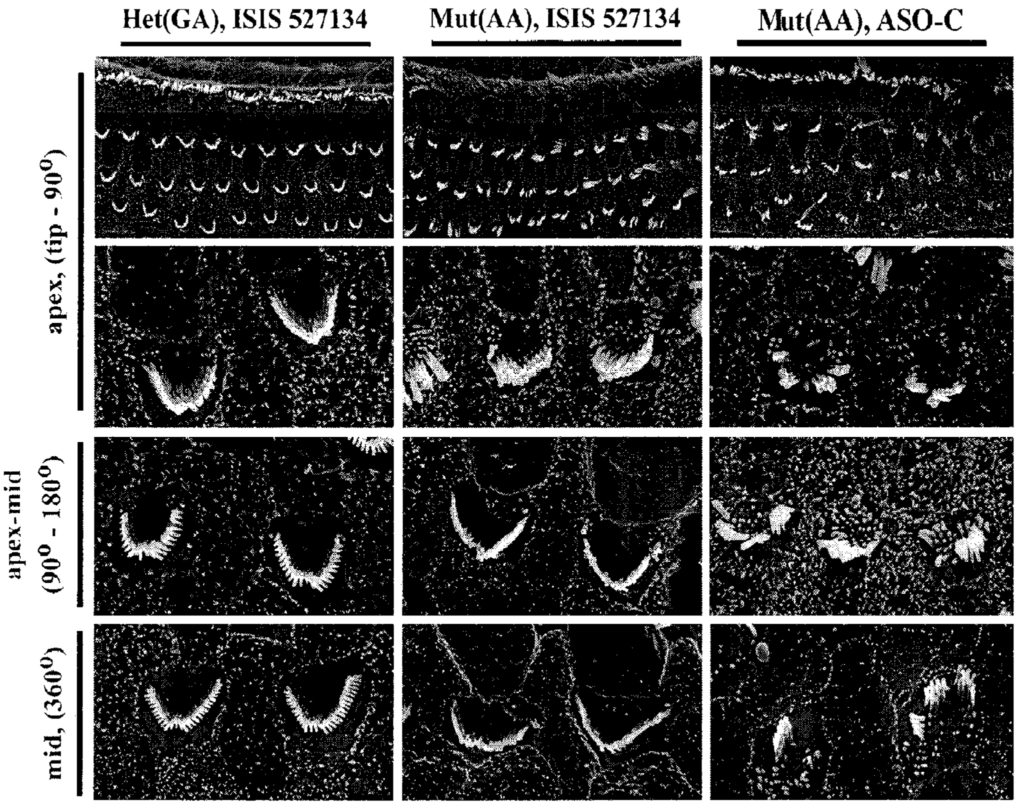
FIG. 4*f* illustrates SEM images of the stereocilia of Ush1c.2166AA mice treated with a mismatched control, Ush1c.2166AA mice treated with Isis No. 527134, and heterozygous mice treated with Isis No. 527134.
Figure 11A:
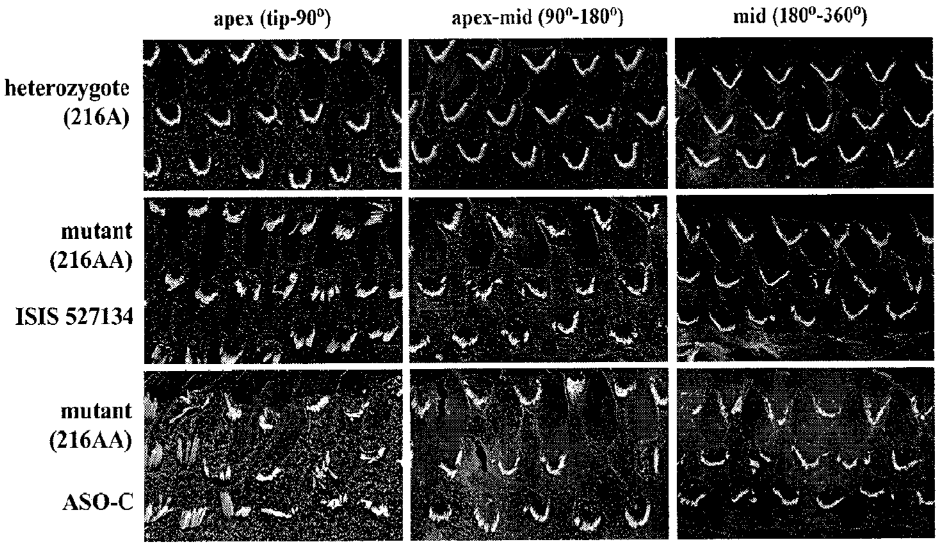
FIG. 11*a* shows SEM images of the apex tip, the middle apex, and the middle turn region of the organ of Corti of Ush1c.216AA mutant mice treated with Isis No. 527134, Ush1c.216AA mutant mice treated with a mismatched control, and heterozygous mice.
Figure 11B:
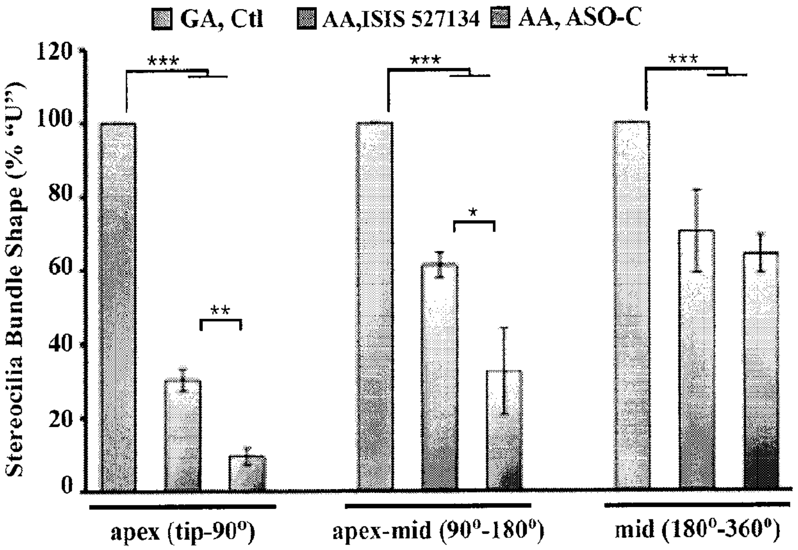
FIG. 11*b* shows the quantitation of SEM images of the apex tip, the middle apex, and the middle turn region of the organ of Corti of Ush1c.216AA mutant mice treated with Isis No. 527134, Ush1c.216AA mutant mice treated with a mismatched control, and heterozygous mice.

Scanning electron microscopy (SEM) was used to analyze the inner ear morphology of P18 mutant Ush1c.216AA mice treated with Isis No. 527134, heterozygous 216GA mice treated with a mismatched control, and mutant Ush1c.216AA mice treated with a mismatched control. SEM analysis of the organ of Corti from the mutant Ush1c.216AA mice treated with Isis No. 527134 showed some correction of the mutant abnormal hair cell bundles with fewer splayed, disorganized and disconnected groups of stereocilia (FIG. 4*f*). To quantify this effect, stereocilia bundles that resembled a characteristic “U” or “W”-shape were counted from blinded images of at least 100 hair cells from each experimental group taken from the apex tip, the middle apex, and the middle turn region of the organ of Corti (FIG. 4*e*, 11*a*). Images from at least 3 animals in each group were evaluated and the percent of total cells that resembled a “U” or “W”-shape were calculated. The mutant Ush1c.216AA mice treated with a mismatched control had significantly less “U”-shaped bundles in the apex tip and middle apex region compared to mutant mice treated with Isis No. 527134 (FIG. 11*a* and FIG. 11*b*). Table 11 below shows the results of the SEM quantitation.

In the middle turn region, the rescue of stereocilia morphology in the Ush1c.216AA mice treated with Isis No. 527134 was not significantly different from Ush1c.216AA mice treated with a mismatched control (FIG. 11*a* and FIG. 11*b*). Heterozygous 216GA mice had significantly more normal shaped bundles than 216AA mice treated with Isis No. 527134 (FIG. 11*a* and FIG. 11*b*). This pattern of stereocilia rescue in the apical to basal direction is consistent with the more robust rescue of hearing at the frequencies detected by hair cells at the apex (8 kHz). This example demonstrates that rescue of hearing in mice can be achieved with partial rescue of stereocilia bundle structure and organization.

TABLE 11

Stereocilia morphology in Ush1c.216AA and 216GA heterozygous mice

| Treatment | Animal | Average Amount of "U" or "W" Stereocilia Bundles Apex | Mid-Apex | Middle-Turn |
|---|---|---|---|---|
| Isis No. 527134 | AA | 30 | 61 | 70 |
| Control | AA | 9 | 32 | 63 |
| Control | GA | 100 | 100 | 100 |

The invention claimed is:

1. A compound comprising a modified oligonucleotide consisting of 15 to 24 linked nucleosides and having a nucleobase sequence comprising a complementary region comprising at least 15 contiguous nucleobases complementary to a target region of equal length within exon 3 or intron 3 of an Usher transcript, wherein the Usher transcript has the nucleobase sequence of SEQ ID NO.: 1, and wherein the complementary region of the modified oligonucleotide is 100% complementary to the target region and comprises 10 contiguous nucleobases of SEQ ID NO: 2, 3, 4, 5, 6, 7, 8, 9, 10, 11, 12, 13, 14, 15, 16, 17, 18, 19, 20, 21, 22, 24, 25, 26, 28, 29, 30, 31, 49, 50, 51, 52, 53, 54, 55, 56, 57, or 58.

2. The compound of claim 1, wherein the nucleobase sequence of the oligonucleotide is 100% complementary to an equal-length region within exon 3 or intron 3 of the Usher transcript, as measured over the entire length of the oligonucleotide.

3. The compound of claim 1, wherein the modified oligonucleotide comprises at least one modified nucleoside.

4. The compound of claim 3, wherein at least one modified nucleoside comprises a modified sugar moiety.

5. The compound of claim 4, wherein at least one modified sugar moiety is a 2'-substituted sugar moiety.

6. The compound of claim 5, wherein the 2'-substitutent of at least one 2'-substituted sugar moiety is selected from among: 2'-OMe, 2'-F, and 2'-MOE.

7. The compound of claim 6, wherein the 2'-substitutent of at least one 2'-substituted sugar moiety is 2'-MOE.

8. The compound of claim 1, wherein the modified oligonucleotide comprises at least 15 modified nucleosides.

9. The compound of claim 8, wherein each modified nucleoside comprises a modified sugar moiety.

10. The compound of claim 9, wherein at least one modified sugar moiety is a 2'-substituted sugar moiety.

11. The compound of claim 10, wherein the 2'-substitutent of at least one 2'-substituted sugar moiety is selected from among: 2'-OMe, 2'-F, and 2'-MOE.

12. The compound of claim 11, wherein the 2'-substitutent of at least one 2'-substituted sugar moiety is 2'-MOE.

13. The compound of claim 1, wherein at least one internucleoside linkage of the modified oligonucleotide is a modified internucleoside linkage and wherein each internucleoside linkage comprises the same modification.

14. The compound of claim 13, wherein each internucleoside linkage is a phosphorothioate internucleoside linkage.

15. The compound of claim 1, wherein the modified oligonucleotide has a nucleobase sequence selected from among SEQ ID NOs. 30, 19, 20, 21, 22, 24, 25, 26, 28, or 29.

* * * * *